US007875605B2

(12) United States Patent
Ramakrishna et al.

(10) Patent No.: US 7,875,605 B2
(45) Date of Patent: Jan. 25, 2011

(54) N-ARYLSULFONYL-3-SUBSTITUTED INDOLES HAVING SEROTONIN RECEPTOR AFFINITY, PROCESS FOR THEIR PREPARATION AND PHARMACEUTICAL COMPOSITION CONTAINING THEM

(75) Inventors: Venkata Satya Nirogi Ramakrishna, Adhra Pradesh (IN); Vikas Shreekrishna Shirsath, Adhra Pradesh (IN); Rama Sastri Kambhampati, Adhra Pradesh (IN); Venkata Satya Veerabhadra Vadlamudi Rao, Adhra Pradesh (IN); Venkateswarlu Jasti, Adhra Pradesh (IN)

(73) Assignee: Suven Life Sciences Limited (IN)

( * ) Notice: Subject to any disclaimer, the term of this patent is extended or adjusted under 35 U.S.C. 154(b) by 1285 days.

(21) Appl. No.: 10/536,618

(22) PCT Filed: Jun. 5, 2003

(86) PCT No.: PCT/IN03/00209

§ 371 (c)(1),
(2), (4) Date: Apr. 11, 2006

(87) PCT Pub. No.: WO2004/048330

PCT Pub. Date: Jun. 10, 2004

(65) Prior Publication Data

US 2006/0223890 A1    Oct. 5, 2006

(30) Foreign Application Priority Data

Nov. 28, 2002    (IN)    .......................... 884/MAS/2002

(51) Int. Cl.
*A61K 31/5513* (2006.01)
*A61K 31/497* (2006.01)
*C07D 403/06* (2006.01)
*C07D 223/00* (2006.01)

(52) U.S. Cl. ........................... 514/211.08; 514/252.13; 540/484; 544/373

(58) Field of Classification Search ............ 514/211.08, 514/252.13, 252.18; 540/484; 544/373
See application file for complete search history.

(56) References Cited

U.S. PATENT DOCUMENTS

| 4,839,377 A | 6/1989 | Bays et al. |
| 4,855,314 A | 8/1989 | Oxford et al. |
| 5,298,491 A | 3/1994 | Chauveau et al. |
| 6,255,306 B1 | 7/2001 | Macor |

FOREIGN PATENT DOCUMENTS

| CN | 1345724 A | 4/2002 |
| EP | 303506 A2 | 2/1989 |
| EP | 313397 A1 | 4/1989 |
| EP | 354777 A2 | 2/1990 |
| EP | 438230 A2 | 7/1991 |
| EP | 457701 A1 | 11/1991 |
| EP | 497512 A2 | 8/1992 |
| GB | 1305458 A | 1/1973 |
| GB | 2035310 A | 6/1980 |
| JP | 05043544 A | 2/1993 |
| JP | 2000344744 A | 12/2000 |
| WO | 9118897 | 12/1991 |
| WO | WO-9213856 A | 8/1992 |
| WO | 9300086 | 1/1993 |
| WO | 9323396 | 11/1993 |
| WO | 9406769 | 3/1994 |
| WO | WO-9603400 A | 2/1996 |
| WO | WO-0247687 A | 6/2002 |
| WO | WO-02058702 A | 8/2002 |

OTHER PUBLICATIONS

Sudha R. Vippagunta et al., Crystalline Solids; Advanced Drug Delivery Reviews; vol. 48, issue 1, May 16, 2001, pp. 3-26.*
Le Borgne, M. et al, "New selective nonsteroidal . . . ", Bioorganic & Medicinal Chemistry Letters, 1999, 333-336, vol. 9, No. 3, Elsevier Science Ltd, GB.
Nagarathnam, D., et al, "A Facile Synthesis of 3-Substituted Indoles", J. Heterocyclic Chem., 1992, 953-958, vol. 29, Univ. of Illinois at Chicago, Chicago, IL.
Marchand, P. et al, "3(azotylmethyl)1H-indoles as . . . ", Pharmacy and Pharmacology Commun, 1998, 211-218, vol. 4, No. 4, CAPLUS Online, Royal Pharm. Society of Great Britain, GB.
Ketcha, D.M. et al, "A Convenient Synthesis of 3-Acylindoles . . . ", The Journal of Organic Chemistry, 1985, 5451-5457, vol. 50, No. 26, American Chemical Society, NH.
Seebach, D. et al, "Design and Synthesis of gamma-Dipeptide Derivatives . . . ", Angew. Chem. Int., 2003, 776-778, vol. 42, No. 7, Wiley-VCH Verlag GmbH 7 Co. KGaA, Weinheim.
Zhang, P. et al, "Regiospecific Bromination of 3-Methylindoles . . . ", Tetrahedron Letters, 1995, 3103-3106, vol. 36, No. 18, Elsevier Science Ltd, GB.
Nagarathnam, D., et al, Synth. Commun., 1993, 2011-2017, vol. 23, No. 14, Beilstein Online Registry No. 6339193, Frankfurt, DE.
Buttery, Cheryl D., et al., Chem. Soc. Perkin Trans., 1993, 1425-1432, vol. 13, Beilstein Online Registry No. 6149229, Frankfurt, DE.
Sato, M., Tetrahedron Lett., 1990, 4697-4698, vol. 31, No. 33, Beilstein Online Registry No. 4193743, Frankfurt, DE.
Boggs, Jason, "Preparation of an electrophilic . . . ", Journal of the Arkansas Academy of Science, 2000, 33-37, vol. 54, CAPLUS Online, AR, USA.

(Continued)

*Primary Examiner*—James O Wilson
*Assistant Examiner*—Ebenezer Sackey
(74) *Attorney, Agent, or Firm*—Iphorgan Ltd.

(57) ABSTRACT

N-arylsulfonyl-3-substituted indole compounds, derivatives, analogs, tautomeric forms, stereoisomers, geometric forms, N-oxides, polymorphs and pharmaceutically acceptable salts.

9 Claims, No Drawings

OTHER PUBLICATIONS

Benedetti, F., J. Chem. Soc. Chem. Commun., 1996, 1417-1418, vol. 12, Beilstein Online Registry No. 7538920, Frankfurt, DE.

Mouaddib, A., Synth. Commun,, 2000, 549-556, vol. 4, Beilstein Online Registry No. 8491943, Frankfurt, DE.

Babu, S.D., Can. J. Chem., 1989, 1071-1076, vol. 67, Beilstein Online Registry No. 4488731, Frankfurt, DE.

Malleron, J-L. et al, "New Indole Derivatives as Potent and Selective . . . ", Journal of Medicinal Chemistry, 1993, 1194-1202, vol. 36, vol. 36, No. 9, Cedex, France.

Mutulis, Felikss et al, "Reductive Amination Products Containing . . . ", Bioorganic & Medicinal Chemistry Letters, 2002, 1035-1038, vol. 12, No. 7, Elsevier Science Ltd., GB.

Russel M G N et al, "N-Arylsulfonylindole derivatives as . . . ", Journal of Medicinal Chemistry, 2001, 3881-3895, vol. 44, No. 23, American Chemical Society, Washington, US.

Degraw, J.I. et al., Journal of Medicinal Chemistry, 1966, 140-142, 9, Beilstein Online Registry No. 1592954, Frankfurt, DE.

Love, B.E., Syn. Lett., 1998, 1123-1125, Beilstein Online Registry No. 885083, Frankfurt, DE.

International Search Report issued in counterpart PCT Appln No. PCT/IN2003/000209.

Written Opinion issued in counterpart PCT Appl No. PCT/IN2003/000209.

International Preliminary Report on Patentability issued in counterpart PCT Appln No. PCT/IN2003/000209.

Shen, Y., et al., "Molecular Cloning and Expression of a 5-Hydroxytryptamine7 Serotonin Receptor Subtype", J. Biol. Chem., (1993) pp. 18200-18204, vol. 268.

Saxena, P.R., et al., "Cardiovascular Effects of Serotonin Agonists and Antagonists", Journal of Cardiovascular Pharmacology, (1990), 15 (Supp 7): S17-S34, Raven Press, Ltd.

Glennon, R., et al., "Serotonin Receptors: Clinical Implications", Neuroscience and Behavioral Reviews, (1990), pp. 35-47, vol. 14, Pergamon Press.

Hoyer, D., et al., "VII. International Union of Pharmacology Classification of Receptors for 5-Hydroxytrypatamine (Serotonin)", Pharmacol Rev., (1994), pp. 157-203, vol. 46, The American Society for Pharmacology and Experimental Therapeutics.

Monsma, F., et al., "Cloning and Expression of Novel Serotonin Receptor with High Affinity for Tricyclic Psychotropic Drugs", Mol. Pharmacol., (1993), pp. 320-327, vol. 43, The American Society for Pharmacology and Experimental Therapeutics.

Ruat, M., et al., "A Novel Rat Serotonin (5-HT6) Receptor: Molecular Cloning, Localization and Stimulation of camp accumulation", Biochem. Biophys. Res. Com., (1993), pp. 268-276, vol. 193, Academic Press, Inc.

Roth, B., et al., "Binding of Typical and Atypical Antipsychotic Agents to 5-Hydroxytryptamine-6 and 5-Hydroxytryptamine-7 Receptors", J. Pharm. Exp. Therapeut., (1994), pp. 1403-1410, vol. 268, The American Society for Pharmacology and Experimental Therapeutics.

Sleight, A., et al., "The 5-Hydroxytryptamine6 Receptor: Localisation and Function", Exp. Opin. Ther. Patents, (1998), pp. 1217-1224, vol. 8, Ashley Publications Ltd.

Bourson, A., et al., "Involvement of 5-HT6 Receptors in Nigrostriatal Function in Rodents", Brit. J. Pharmacol., (1998), pp. 1562-1566, vol. 125, Stockton Press.

Boess, F., et al., "The 5-Hydroxytryptamine6 Receptor-Selective Radioligand [3H]Ro 63-0563 Labels 5-Hydroxytryptamine Receptor Binding Sites in Rat and Porcine Striatum", Mol. Pharmacol., (1998), pp. 577-583, vol. 54. The American Society for Pharmacology and Experimental Therapeutics.

Sleight, A., et al., "Characterization of Ro 04-6790 and Ro 63-0563: Potent and Selective Antagonists at Human and Rat 5-HT6 Receptors", Brit. J. Pharmacol., (1998), pp. 556-562, vol. 124, Stockton Press.

Yoshioka, M., et al., "Central Distribution and Function of 5-HT6 Receptor Subtype in the Rat Brain", Life Sciences, (1998), pp. 1473-1477, vol. 62, Elsevier Science Inc.

Schoeffter, P., et al., "SDZ 216-525, a Selective and Potent 5-HT1A Receptor Antagonist", European Journal of Pharmacology, 1993, pp. 251-257, vol. 244, Elsevier Science.

Hoyer, D., et al., "Molecular Pharmacology of 5-HT1 and 5-HT2 Recognition Sites in Rat and Pig Brain Membranes . . . ", Eur. Jrnl. Pharmacol., (1985), pp. 13-23, vol. 118, Elsevier.

Grossman, C.J., et al., "Development of a Radioligand Binding Assay for 5HT4 Receptors in Guinea Pig and Rat Brain", Brit., Jrnl. Pharmacol., (1993), pp. 618-624, vol. 109, Macmillan Press.

Rees, S., et al, "Cloning and Characterisation of the Human 5-HT5A Serotonin Receptor", FEBS Letters, (1994), pp. 242-246, vol. 355, Federation of European Biochemical Societies.

Lummis, S.C.R., et al., "Characterization of 5HT3 Receptors in Intact N1E-115 Neuroblastoma Cells", Eur. Jrnl. Pharmacol., (1990), pp. 223-227, vol. 189, Elsevier.

Hoyer, D. and Neijt, H.C., "Identification of Serotonin 5-HT3 Recognition Sites in Membranes of N1E-115 Neuroblastoma Cells by Radioligand Binding", Mol. Pharmacol., (1988), pp. 303-309, vol. 33, The American Society for Pharmacology and Experimental Therapeutics.

Schoeffter, P., and Hoyer, D., "How Selective is GR 43175? Interactions with Functional 5-HT1A, 5-HT1B, 5-HT1C and 5-HT1D Receptors", Naunyn-Schmiedeberg's Arch. Pharmac., (1989), pp. 135-138, vol. 340, Springer-Verlag.

Waeber, C., et al., "Molecular Pharmacology of 5-HT1D Recognition Sites: Radioligand Binding Studies in Human, Pig and Calf Brain Membranes", Naunyn-Schmiedeberg's Arch. Pharmacol., (1988), pp. 595-601, vol. 337, Springer-Verlag.

Leysen, J.E., et al., "[3H]Ketanserin (R 41 468), A Selective 3H-Ligand for Serotonin2 Receptor Binding Sites", Mol. Pharmacol., (1982), pp. 301-314, vol. 21, The American Society for Pharmacology and Experimental Therapeutics.

Martin, G.R. and Humphrey, P.P.A., "Classification Review: Receptors for 5-HT: Current Perspectives on Classification and Nomenclature", Neuropharmacol., (1994), pp. 261-273, vol. 33(3/4), Elseier Science Ltd.

Pazos, A., et al., "The Binding of Serontonergic Ligands to the Porcine Choroid Plexus: Characterization of a new Type of Serotonin Recohnition Site", Eur. Jrnl. Pharmacol., (1985), pp. 539-546, vol. 106, Elsevier.

* cited by examiner

N-ARYLSULFONYL-3-SUBSTITUTED INDOLES HAVING SEROTONIN RECEPTOR AFFINITY, PROCESS FOR THEIR PREPARATION AND PHARMACEUTICAL COMPOSITION CONTAINING THEM

This application is a §371 National Stage of PCT International Application No. PCT/IN2003/000209, filed Jun. 5, 2003, claiming priority of Indian Patent Application No. 884/MAS/2002 filed Nov. 28, 2002, the contents of which are hereby incorporated by reference.

FIELD OF INVENTION

Particularly, the present invention relates to Novel N-arylsulfonyl-3-substituted indoles of the general formula (I), their derivatives, their analogs, their tautomeric forms, their stereoisomers, their geometric forms, their N-oxides, their polymorphs, their pharmaceutically acceptable salts, their pharmaceutically acceptable solvates, pharmaceutically acceptable compositions containing them and use of these compounds in medicine, medicaments containing them and their use as diagnostic agents.

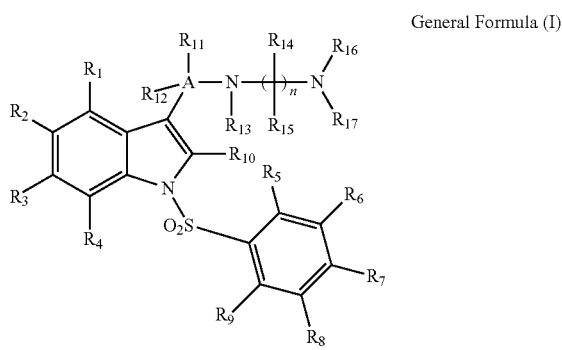

General Formula (I)

The present invention also relates to the process for preparing the compounds of general formula (I), their derivatives, their analogs, their tautomeric forms, their stereoisomers, their geometric forms, their N-oxides, their polymorphs, their pharmaceutically acceptable salts, their pharmaceutically acceptable solvates, the novel intermediates involved therein and pharmaceutically acceptable compositions containing them.

The compounds of the general formula (I) of this invention are 5-HT (Serotonin) ligands e.g. agonists or antagonists. Thus, compounds of general formula (I) of this invention are useful for treating diseases wherein modulation of 5-HT (Serotonin) activity is desired. Specifically, the compounds of this invention are useful in the treatment and/or prophylaxis of psychosis, paraphrenia, psychotic depression, mania, schizophrenia, schizophreniform disorders, anxiety, migraine headache, depression, drug addiction, convulsive disorders, personality disorders, hypertension, autism, post-traumatic stress syndrome, alcoholism, panic attacks, obsessive-compulsive disorders and sleep disorders. The compounds of general formula (I) of this invention are also useful to treat psychotic, affective, vegetative and psychomotor symptoms of schizophrenia and the extrapyramidal motor side effects of other antipsychotic drugs.

The compounds of general formula (I) of this invention are also useful to treat neurodegenerative disorders like Alzheimer's disease, Parkinsonism and Huntington's chorea and chemotherapy-induced vomiting. The compounds of general formula (I) of this invention are also useful in modulation of eating behavior and thus are useful in reducing the morbidity and mortality associated with excess weight.

BACKGROUND OF THE INVENTION

Many diseases of the central nervous system are influenced by the adrenergic, the dopaminergic and the serotenergic neurotransmitter systems. Serotonin has been implicated in a number of diseases and conditions, which originate in the central nervous system. These include diseases and conditions related to sleeping, eating, perceiving pain, controlling body temperature, controlling blood pressure, depression, anxiety, schizophrenia and other bodily states. (References: Fuller, R. W., Drugs Acting on Serotonergic Neuronal Systems, Biology of Serotonergic Transmission, John Wiley & Sons Ltd. (1982), 221-247; Boullin D. J., Serotonin in Mental abnormalities (1978), 1, 316; Barchas J. et. al., Serotonin and Behavior (1973)). Serotonin also plays an important role in the peripheral systems, such as the gastrointestinal system, where it has been found to mediate a variety of contractile, secretory and electrophysiologic effects.

Due to the broad distribution of serotonin within the body, there is lot of interest and use, in the drugs that affect serotonergic systems. Particularly, preferred are the compounds which have receptor specific agonism and/or antagonism for the treatment of a wide range of disorders, including anxiety, depression, hypertension, migraine, obesity, compulsive disorders, schizophrenia, autism, neurodegenerative disorders like Alzheimer's disease, Parkinsonism and Huntington's chorea and chemotherapy-induced vomiting (References: Gershon M. D. et. al., The peripheral actions of 5-Hydroxytryptamine (1989), 246; Saxena P. R. et. al., Journal of Cardiovascular Pharmacology (1990), supplement 7, 15).

The major classes of serotonin receptors ($5-HT_{1-7}$) contain fourteen to eighteen separate receptors that have been formally classified (References: Glennon et al, Neuroscience and Behavioral Reviews (1990), 14, 35 and Hoyer D. et al, Pharmacol. Rev. (1994), 46, 157-203). Recently discovered information regarding sub-type identity, distribution, structure and function suggests that it is possible to identify novel, sub-type specific agents having improved therapeutic profiles with lesser side effects. The $5-HT_6$ receptor was identified in 1993 (References: Monsma et al, Mol. Pharmacol. (1993), 43, 320-327 and Ruat M. et al, Biochem. Biophys. Res. Com. (1993), 193, 269-276). Several antidepressants and atypical antipsychotics bind to the $5-HT_6$ receptor with high affinity and this binding may be a factor in their profile of activities (References: Roth et al, J. Pharm. Exp. Therapeut. (1994), 268, 1403-1410; Sleight et al, Exp. Opin. Ther. Patents (1998), 8, 1217-1224; Bourson et al, Brit. J. Pharmacol. (1998), 125, 1562-1566; Boess et al, Mol. Pharmacol., 1998, 54, 577-583; Sleight et al, Brit. J. Pharmacol. (1998), 124, 556-562). In addition, $5-HT_6$ receptor has been linked to generalized stress and anxiety states (Reference: Yoshioka et al, Life Sciences (1998), 17/18, 1473-1477). Together these studies and observations suggest that compounds that antagonize the $5-HT_6$ receptor will be useful in treating various disorders of the central nervous system.

U.S. Pat. Nos. 4,839,377 and 4,855,314 refer to 5-substituted 3-aminoalkyl indoles. The compounds are said to be useful for the treatment of migraine.

British Patent 2,035,310 refers to 3-aminoalkyl-1H-indole-5-thioamides and carboxamides. The compounds are said to be useful in treating hypertension, Raymond's disease and migraine.

European Patent Publication 303,506 refers to 3-polyhydropyridyl-5-substituted-1H-indoles. The compounds are said to have 5-HT$_1$ receptor agonists and vasoconstrictor activity and to be useful in treating migraine. European Patent Publication 354,777 refers to N-piperidinylindolylethyl-alkane sulfonamide derivatives. The compounds are said to be 5-HT$_1$ receptor agonists and have vasoconstrictor activity and are useful in treating cephalic pain.

European Patent Publication 438,230, refers to indole-substituted five-membered heteroaromatic compounds. The compounds are said to have "5-HT$_1$-like" receptor agonist activity and to be useful in the treatment of migraine and other disorders for which a selective agonist of these receptors is indicated.

European Patent Publication 313,397 refers to 5-heterocyclic indole derivatives. The compounds are said to have exceptional properties for the treatment and prophylaxis of migraine, cluster headache and headache associated with vascular disorders. These compounds are also said to have exceptional "5-HT$_1$-like" receptor agonism.

International Patent Publication WO 91/18897, refers to 5-heterocyclic indole derivatives. The compounds are said to have exceptional properties for the treatment and prophylaxis of migraine, cluster headache, and headache associated with vascular disorders. These compounds are also said to have exceptional "5-HT$_1$-like" receptor agonism.

European Patent Publication 457,701 refers to aryloxy amine derivatives as having high affinity for 5-HT$_{1D}$ serotonin receptors. These compounds are said to be useful for treating diseases related to serotonin receptor dysfunction, for example, migraine.

European Patent Publication 497,512 A2, refers to a class of imidazole, triazole and tetrazole derivatives which are selective agonists for "5-HT$_1$-like" receptors. These compounds are said to be useful for treating migraine and associated disorders.

International Patent Publication WO 93/00086, describes a series of tetrahydrocarbazole derivatives, as 5-HT$_1$ receptor agonists, useful for the treatment of migraine and related conditions.

International Patent Publication WO 93/23396, refers to fused imidazole and triazole derivatives as 5-HT$_1$ receptor agonists, for the treatment of migraine and other disorders.

Schoeffter P. et al. refer to methyl 4-{4-[4-(1,1,3-trioxo-2H-1,2-benzoisothiazol-2-yl)butyl]-1-piperazinyl}1H-indole-3-carboxylate as a selective antagonist for the 5-HT$_{1A}$ receptor in their paper "SDZ216-525, a selective and potent 5-HT$_{1A}$ receptor antagonist" European Journal of Pharmacology, 244, 251-257 (1993).

International Patent Publication WO 94/06769, refers to 2-substituted-4-piperazine-benzothiophene derivatives that are serotonin 5-HT$_{1A}$ and 5-HT$_{1D}$ receptor agents useful in the treatment of anxiety, depression, migraine, stroke, angina and hypertension.

SUMMARY OF THE INVENTION

The present invention relates to novel substituted N-arylsulfonyl-3-substituted indoles of the general formula (I),

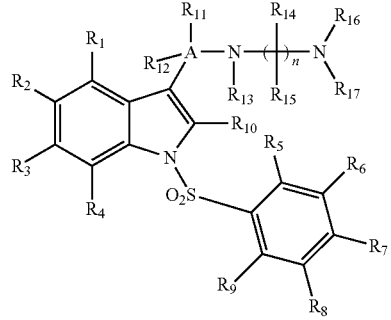

General Formula (I)

their derivatives, their analogs, their tautomeric forms, their stereoisomers, their geometric forms, their N-oxides, their polymorphs, their pharmaceutically acceptable salts and their pharmaceutically acceptable solvates, wherein A may be —CH$_2$—, —C=O or —SO$_2$—; R$_{11}$ and R$_{12}$, refer to substitutions on the carbon whenever A is CH$_2$; R$_1$, R$_2$, R$_3$, R$_4$, R$_5$, R$_6$, R$_7$, R$_8$, R$_9$, R$_{10}$, R$_{11}$, R$_{12}$, R$_{14}$ and R$_{15}$ may be same or different and each independently represent hydrogen, halogen, oxo, thio, perhaloalkyl, hydroxy, amino, nitro, cyano, formyl, amidino, guanidino, substituted or unsubstituted groups selected from linear or branched (C$_1$-C$_{12}$)alkyl, (C$_2$-C$_{12}$)alkenyl, (C$_2$-C$_{12}$)alkynyl, (C$_3$-C$_7$)cycloalkyl, (C$_3$-C$_7$)cycloalkenyl, bicycloalkyl, bicycloalkenyl, (C$_1$-C$_{12}$)alkoxy, cyclo(C$_3$-C$_7$) alkoxy,aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like R$_1$ and R$_2$ or R$_2$ and R$_3$ or R$_3$ and R$_4$ or R$_5$ and R$_6$ or R$_6$ and R$_7$ or R$_7$ and R$_8$ or R$_8$ and R$_9$ together with carbon atoms to which they are attached may form a five or a six membered ring, optionally containing one or more double bonds and optionally containing one or more heteroatoms selected from "Oxygen", "Nitrogen", "Sulfur" or "Selenium" and combinations of double bond and heteroatoms; or R$_{11}$ and R$_{12}$ together with the carbon atoms to which they are attached may form a three to six membered ring, optionally containing one or more double bonds and optionally containing one or more heteroatoms selected from "Oxygen", "Nitrogen", "Sulfur" or "Selenium" and combinations of double bond and heteroatoms; R$_{13}$, R$_{16}$ and R$_{17}$ may be same or different and each independently represents Hydrogen, substituted or unsubstituted groups selected from linear or branched (C$_1$-C$_{12}$)alkyl, (C$_2$-C$_{12}$)alkenyl, (C$_2$-C$_{12}$)alkynyl, (C$_3$-C$_7$)cycloalkyl, (C$_3$-C$_7$)cycloalkenyl, bicycloalkyl, bicycloalkenyl, aryl, aralkyl, heteroaryl, heterocyclylalkyl; optionally R$_{13}$ along with either R$_{16}$ or R$_{17}$ and the two nitrogen atoms may form a 5, 6 7-membered heterocyclic ring, which may be further substituted with $R_{14}$ and $R_{15}$, and may have either one, two or three double bonds;

"n" is an integer ranging from 1 to 4, wherein the carbon chains which "n" represents may be either linear or branched.

Partial list of such compounds of general formula (I) are following:

1-Benzenesulfonyl-3-(4-methylpiperazin-1-ylmethyl)-5-nitro-1H-indole;
1-(4-Methylbenzenesulfonyl)-3-(4-methylpiperazin-1-ylmethyl)-5-nitro-1H-indole;
1-(4-Bromobenzenesulfonyl)-3-(4-methylpiperazin-1-ylmethyl)-5-nitro-1H-indole;
1-(4-Fluorobenzenesulfonyl)-3-(4-methylpiperazin-1-ylmethyl)-5-nitro-1H-indole;
1-(4-Methoxybenzenesulfonyl)-3-(4-methylpiperazin-1-ylmethyl)-5-nitro-1H-indole;
1-(4-Isopropylbenzenesulfonyl)-3-(4-methylpiperazin-1-ylmethyl)-5-nitro-1H-indole;
1-(2-Bromobenzenesulfonyl)-3-(4-methylpiperazin-1-ylmethyl)-5-nitro-1H-indole;
1-(2-Bromobenzenesulfonyl)-3-(4-methylpiperazin-1-ylmethyl)-5-nitro-1H-indole hydrochloride salt;
1-(2-Bromo-4-methoxybenzenesulfonyl)-3-(4methylpiperazin-1-ylmethyl)-5-nitro-1H-indole;
4,5,6-Trichloro-1-benzenesulfonyl-3-(4methylpiperazin-1-ylmethyl)-1H-indole;
4,5,6-Trichloro-1-(4-methylbenzenesulfonyl)-3-(4-methylpiperazin-1-ylmethyl)-1H-indole;
1-(4-Bromobenzenesulfonyl)-4,5,6-trichloro-3-(4-methylpiperazin-1-ylmethyl)-1H-indole;
4,5,6-Trichloro-1-(4-isopropylbenzenesulfonyl)-3-(4-methylpiperazin-1-ylmethyl)-1H-indole;
1-(2-Bromobenzenesulfonyl)-4,5,6-trichloro-3-(4-methylpiperazin-1-ylmethyl)-1H-indole;
1-(2-Bromo-4-methoxybenzenesulfonyl)-4,5,6-trichloro-3-(4-methylpiperazin-1-ylmethyl)-1H-indole;
1-Benzenesulfonyl-5-methoxy-3-(4-methylpiperazin-1-ylmethyl)-1H-indole;
1-(4-Methylbenzenesulfonyl)-5-methoxy-3-(4-methylpiperazin-1-ylmethyl)-1H-indole;
1-(4-Bromobenzenesulfonyl)-5-methoxy-3-(4-methylpiperazin-1-ylmethyl)-1H-indole;
1-(4-Isopropylbenzenesulfonyl)-5-methoxy-3-(4-methylpiperazin-1-ylmethyl)-1H-indole;
1-(2-Bromobenzenesulfonyl)-5-methoxy-3-(4-methylpiperazin-1-ylmethyl)-1H-indole;
1-(2-Bromo-4-methoxybenzenesulfonyl)-5-methoxy-3-(4-methylpiperazin-1-ylmethyl)-1H-indole;
1-(2-Bromo-4-methoxybenzenesulfonyl)-5-methoxy-3-(4-methylpiperazin-1-ylmethyl)-1H-indole hydrochloride salt;
1-(4-methoxybenzenesulfonyl)-5-methoxy-3-(4-methylpiperazin-1-ylmethyl)-1H-indole;
1-(4-Fluorobenzenesulfonyl)-5-methoxy-3-(4-methylpiperazin-1-ylmethyl)-1H-indole;
5-Bromo-1-(4-fluorobenzenesulfonyl)-3-(4-methylpiperazin-1-ylmethyl)-1H-indole;
5-Bromo-1-(4-fluorobenzenesulfonyl)-3-(4-methylpiperazin-1-ylmethyl)-1H-indole hydrochloride salt;
5-Bromo-1-(4-fluorobenzenesulfonyl)-3-(4-methylpiperazin-1-ylmethyl)-1H-indole maleate salt;
5-Bromo-1-(4-fluorobenzenesulfonyl)-3-(4-methylpiperazin-1-ylmethyl)-1H-indole citrate salt;
5-Bromo-1-(4-methoxybenzenesulfonyl)-3-(4-methylpiperazin-1-ylmethyl)-1H-indole;
5-Bromo-1-(benzenesulfonyl)-3-(4-methylpiperazin-1-ylmethyl)-1H-indole;
5-Bromo-1-(4-methylbenzenesulfonyl)-3-(4-methylpiperazin-1-ylmethyl)-1H-indole;
5-Bromo-1-(4-bromobenzenesulfonyl)-3-(4-methylpiperazin-1-ylmethyl)-1H-indole;
5-Bromo-1-(4-isopropylbenzenesulfonyl)-3-(4-methylpiperazin-1-ylmethyl)-1-H-indole;
5-Bromo-1-(2-bromobenzenesulfonyl)-3-(4-methylpiperazin-1-ylmethyl)-1-H-indole;
5-Bromo-1-(2-bromobenzenesulfonyl)-3-(4-methylpiperazin-1-ylmethyl)-1H-indole hydrochloride salt;
5-Bromo-1-(2-bromo-4-methoxybenzenesulfonyl)-3-(4-methylpiperazin-1-ylmethyl)-1H-indole;
4-Bromo-1-(4-fluorobenzenesulfonyl)-3-(4-methylpiperazin-1-ylmethyl)-1H-indole;
4-Bromo-1-(4-methoxybenzenesulfonyl)-3-(4methylpiperazin-1-ylmethyl)-1H-indole;
4-Bromo-1-(4-isopropylbenzenesulfonyl)-3-(4-methylpiperazin-1-ylmethyl)-1H-indole;
(1-Benzenesulfonyl-1H-indol-3-yl)-(4-methylpiperazin-1-yl)methanone;
[1-(4-Methylbenzenesulfonyl)-1H-indol-3-yl]-(4-methylpiperazin-1-yl)methanone;
[1-(4-Isopropylbenzenesulfonyl)-1H-indol-3-yl]-(4-methylpiperazin-1-yl)methanone;
[1-(2-Bromobenzenesulfonyl)-1H-indol-3-yl]-(4-methylpiperazin-1-yl)methanone;
[1-(2-Bromo-4-methoxybenzenesulfonyl)-1H-indol-3-yl]-(4-methylpiperazin-1-yl)methanone;
(1-Benzenesulfonyl-5-nitro-1H-indol-3-yl)-(4-methylpiperazin-1-yl)methanone;
[1-(4-Methylbenzenesulfonyl)-5-nitro-1H-indol-3-yl]-(4-methylpiperazin-1-yl)methanone;
[1-(4-Fluorobenzenesulfonyl)-5-nitro-1H-indol-3-yl]-(4-methylpiperazin-1-yl)methanone;
[1-(4-Bromobenzenesulfonyl)-5-nitro-1H-indol-3-yl]-(4-methylpiperazin-1-yl)methanone;
[1-(4-Isopropylbenzenesulfonyl)-5-nitro-1H-indol-3-yl]-(4-methylpiperazin-1-yl)methanone;
[1-(2-Bromobenzenesulfonyl)-5-nitro-1H-indol-3-yl]-(4-methylpiperazin-1-yl)methanone;
[1-(4-Methoxybenzenesulfonyl)-5-nitro-1H-indol-3-yl]-(4-methylpiperazin-1-yl)methanone;
[1-(2-Bromo-4-methoxybenzenesulfonyl)-5-nitro-1H-indol-3-yl]-(4-methylpiperazin-1-yl)methanone;
1-Benzenesulfonyl-3-(4-methylpiperazin-1-ylmethyl)-1H-indole;
1-(4-Methylbenzenesulfonyl)-3-(4-methylpiperazin-1-ylmethyl)-1H-indole;
1-(4-Fluorobenzenesulfonyl)-3-(4-methylpiperazin-1-ylmethyl)-1H-indole;
1-(4-Bromobenzenesulfonyl)-3-(4-methylpiperazin-1-ylmethyl)-1H-indole;
1-(4-Isopropylbenzenesulfonyl)-3-(4-methylpiperazin-1-ylmethyl)-1H-indole;
1-(2-Bromobenzenesulfonyl)-3-(4-methylpiperazin-1-ylmethyl)-1H-indole;
1-(2-Bromobenzenesulfonyl)-3-(4-methylpiperazin-1-ylmethyl)-1H-indole hydrochloride salt;
1-(2-Bromo-4-methoxybenzenesulfonyl)-3-(4-methylpiperazin-1-ylmethyl)-1H-indole;
1-(2-Bromo-4-methoxybenzenesulfonyl)-3-(4-methylpiperazin-1-ylmethyl)-1H-indole hydrochloride salt;

1-(4-methoxybenzenesulfonyl)-3-(4-methylpiperazin-1-yl-methyl)-1H-indole;
1-(2-Bromo-4-methoxybenzenesulfonyl)-5-chloro-2-methyl-3-(4-methylpiperazin-1-ylmethyl)-1H-indole;
5-Chloro-1-(4-fluorobenzenesulfonyl)-2-methyl-3-(4-methylpiperazin-1-ylmethyl)-1H-indole;
1-(4-Bromobenzenesulfonyl)-5chloro-2-methyl-3-(4-methylpiperazin-1-ylmethyl)-1H-indole;
5-Chloro-1-(4-Isopropylbenzenesulfonyl)-2-methyl-3-(4methylpiperazin-1-ylmethyl)-1H-indole;
1-Benzenesulfonyl-5-chloro-2-phenyl-3-(4-methylpiperazin-1-ylmethyl)-1H-indole;
5-Chloro-1-(4-methylbenzenesulfonyl)-2-phenyl-3-(4-methylpiperazin-1-ylmethyl)-1H-indole;
1-(Benzenesulfonyl)-5-fluoro-2-phenyl-3-(4-methylpiperazin-1-ylmethyl)-1H-indole;
5-Fluoro-1-(4-methylbenzenesulfonyl)-2-phenyl-3-(4-methylpiperazin-1-ylmethyl)-1H-indole;
1-(4-Bromobenzenesulfonyl)-5-chloro-2-phenyl-3-(4-methylpiperazin-1-ylmethyl)-1H-indole;
1-(2-Bromobenzenesulfonyl)-5-cyano-3-(4-methylpiperazin-1-ylmethyl)-1H-indole;
5-Cyano-1-(4-methoxybenzenesulfonyl)-3-(4-methylpiperazin-1-ylmethyl)-1H-indole;
5-Cyano-1-(4-fluorobenzenesulfonyl)-3-(4-methylpiperazin-1-ylmethyl)-1H-indole;
1-(4-Bromobenzenesulfonyl)-5-cyano-3-(4-methylpiperazin-1-ylmethyl)-1H-indole;
5-Cyano-1-(4-Isopropylbenzenesulfonyl)-3-(4-methylpiperazin-1-ylmethyl)-1H-indole;
N-(1-(4-Fluorobenzenesulfonyl)-1H-indol-3-yl)methyl-N,N',N'-trimethylethylene-1,2-diamine;
N-(1-(4-Fluorobenzenesulfonyl)-1H-indol-3-yl)methyl-N,N',N'-trimethylethylene-1,2-diamine hydrochloride salt;
N-(1-(4-Bromobenzenesulfonyl)-5-bromo-1H-indol-3-yl)methyl-N,N',N'-trimethylethylene-1,2-diamine;
N-(1-(4-Bromobenzenesulfonyl)-5-bromo-1H-indol-3-yl)methyl-N,N',N'-trimethylethylene-1,2-diamine hydrochloride salt;
N-(5-Bromo-1-(4-methoxybenzenesulfonyl)-1H-indol-3-yl)methyl-N,N',N'-trimethylethylene-1,2-diamine;
N-(1-(4-Methoxybenzenesulfonyl)-5-nitro-1H-indol-3-yl)methyl-N,N',N'-trimethylethylene-1,2-diamine;
N-(1-(4-Methoxybenzenesulfonyl)-5-nitro-1H-indol-3-yl)methyl-N,N',N'-trimethylethylene-1,2-diamine hydrochloride salt;
N-(1-(2-Bromobenzenesulfonyl)-5-bromo-1H-indol-3-yl)methyl-N,N',N'-trimethylethylene-1,2-diamine;
1-(2-Bromobenzenesulfonyl)-3-(4-(3-chlorobenzene-1-yl)piperazin-1-ylmethyl)-1H-indole;
1-(4-Methoxybenzenesulfonyl)-3-(4-(2-methoxybenzene-1-yl)piperazin-1-ylmethyl)-1H-indole;
1-(2-Bromo-4-methoxybenzenesulfonyl)-3-(4-(2-methoxybenzene-1-yl)piperazin-1-ylmethyl)-1H-indole;
1-(4-Isopropylbenzenesulfonyl)-3-(4-(2-methoxybenzene-1-yl)piperazin-1-ylmethyl)-1H-indole;
5-Bromo-1-(4-fluorobenzenesulfonyl)-3-(4-(2-methoxybenzene-1-yl)piperazin-1-ylmethyl)-1H-indole;
5-Bromo-1-(4-methoxybenzenesulfonyl)-3-(4-(2-methoxybenzene-1-yl)piperazin-1-ylmethyl)-1H-indole;
5-Bromo-1-(4-isopropylbenzenesulfonyl)-3-(4-(2-methoxybenzene-1-yl)piperazin-1-ylmethyl)-1H-indole;
1-(4-Fluorobenzenesulfonyl)-5-methoxy-3-(4-(2-methoxybenzene-1-yl)piperazin-1-ylmethyl)-1H-indole;
1-(4-Fluorobenzenesulfonyl)-5-methoxy-3-(4-(2-methoxybenzene-1-yl)piperazin-1-ylmethyl)-1H-indole hydrochloride salt;
1-(4-Methoxybenzenesulfonyl)-5-methoxy-3-(4-(2-methoxybenzene-1-yl)piperazin-1-ylmethyl)-1H-indole;
1-(4-Isopropylbenzenesulfonyl)-5-methoxy-3-(4-(2-methoxybenzene-1-yl)piperazin-1-ylmethyl)-1H-indole;
1-(4-Fluorobenzenesulfonyl)-3-(4-(pyridin-2-yl)piperazin-1-ylmethyl)-1H-indole;
1-(4-Methoxybenzenesulfonyl)-3-(4-(pyridin-2-yl)piperazin-1-ylmethyl)-1H-indole;
1-(4-Isopropylbenzenesulfonyl)-3-(4-(pyridin-2-yl)piperazin-1-ylmethyl)-1H-indole;
1-(2-Bromobenzenesulfonyl)-3-(4-(pyridin-2-yl)piperazin-1-ylmethyl)-1H-indole;
1-(2-Bromo-4-methoxybenzenesulfonyl)-3-(4-(pyridin-2-yl)piperazin-1-ylmethyl)-1H-indole;
5-Bromo-1-(4-fluorobenzenesulfonyl)-3-(4-(pyridin-2-yl)piperazin-1-ylmethyl)-1H-indole;
5-Bromo-1-(4-methoxybenzenesulfonyl)-3-(4-(pyridin-2-yl)piperazin-1-ylmethyl)-1H-indole;
5-Bromo-1-(4-isopropylbenzenesulfonyl)-3-(4-(pyridin-2-yl)piperazin-1-ylmethyl)-1H-indole;
1-(4-Fluorobenzenesulfonyl)-5-methoxy-3-(4-(pyridin-2-yl)piperazin-1-ylmethyl)-1H-indole;
1-(4-Methoxybenzenesulfonyl)-5-methoxy-3-(4-(pyridin-2-yl)piperazin-1-ylmethyl)-1H-indole;
1-(4-Isopropylbenzenesulfonyl)-5-methoxy-3-(4-(pyridin-2-yl)piperazin-1-ylmethyl)-1H-indole;
1-(4-Isopropylbenzenesulfonyl)-5-methoxy-3-(4-(benzyl)piperazin-1-ylmethyl)-1H-indole;
1-(4-Methoxybenzenesulfonyl)-5-methoxy-3-(4-(benzyl)piperazin-1-ylmethyl)-1H-indole;
1-(4-Isopropylbenzenesulfonyl)-3-(4-(benzyl)piperazin-1-ylmethyl)-1H-indole;
1-(4-Methoxybenzenesulfonyl)-3-(4-(benzyl)piperazin-1-ylmethyl)-1H-indole;
1-(2-Bromo-4-methoxybenzenesulfonyl)-3-(4-(benzyl)piperazin-1-ylmethyl)-1H-indole;
1-(Benzenesulfonyl)-3-(4-(benzyl)piperazin-1-ylmethyl)-1H-indole;
1-(4-Methoxybenzenesulfonyl)-3-2-[1,4]Diazepan-1-ylmethyl-1H-indole;
(R,S) 1-(1-Benzenesulfonylindol-3-yl)-1-(4-methylpiperazin-1-yl)ethane;
(R) 1-(1-Benzenesulfonylindol-3yl)-1-(4-methylpiperazin-1-yl)ethane;
(S) 1-(1-Benzenesulfonylindol-3-yl)-1-(4-methylpiperazin-1-yl)ethane;
(R,S) 1-[1-(4-Methylbenzenesulfonyl)indol-3-yl]-1-(4-methylpiperazin-1-yl)ethane;
(R) 1-[1-(4-Methylbenzenesulfonyl)indol-3-yl]-1-(4-methylpiperazin-1-yl)ethane;
(S) 1-[1-(4-Methylbenzenesulfonyl)indol-3-yl]-1-(4-methylpiperazin-1-yl)ethane;
(R,S) 1-[1-(4-Methoxylbenzenesulfonyl)indol-3-yl]-1-(4-methylpiperazin-1-yl)ethane; (R) 1-[1-(4-Methoxylbenzenesulfonyl)indol-3-yl]-1-(4-methylpiperazin-1-yl)ethane;
(S) 1-[1-(4-Methoxybenzenesulfonyl)indol-3-yl]-1-(4-methylpiperazin-1-yl)ethane;
(R,S) 1-[1-(4-Isopropylbenzenesulfonyl)indol-3-yl]-1-(4-methylpiperazin-1-yl)ethane; (R) 1-[1-(4-Isopropylbenzenesulfonyl)indol-3-yl]-1-(4-methylpiperazin-1-yl)ethane;
(S) 1-[1-(4-Isopropylbenzenesulfonyl)indol-3-yl]-1-(4-methylpiperazin-1-yl)ethane;
1-(4-Fluorobenzenesulfonyl)-1H-indole-3-carboxylic acid N-(N',N'-dimethylaminoethyl)-N-methylamide;
1-(4-Methoxybenzenesulfonyl)-1H-indole-3-carboxylic acid N-(N', N'-dimethylaminoethyl)-N-methylamide;

1-(4-Isopropylbenzenesulfonyl)-1H-indole-3-carboxylic acid N-(N',N'-dimethylaminoethyl)-N-methylamide;
(R,S) α-[1-(4-Methoxybenzenesulfonyl)-1H-indol-3-yl]-α-(4-methylpiperazin-1-yl)acetonitrile;
(R) α-[1-(4-Methoxybenzenesulfonyl)-1H-indol-3-yl]-α-(4-methylpiperazin-1-yl)acetonitrile;
(S) α-[1-(4-Methoxybenzenesulfonyl)-1H-indol-3-yl]-α-(4-methylpiperazin-1-yl)acetonitrile;
(R,S) α-[1-(Benzenesulfonyl)-1H-indol-3-yl]-α-(4-methylpiperazin-1-yl)acetonitrile;
(R) α-[1-(Benzenesulfonyl)-1H-indol-3-yl]-α-(4-methylpiperazin-1-yl)acetonitrile;
(S) α-[1-(Benzenesulfonyl)-1H-indol-3-yl]-α-(4-methylpiperazin-1-yl)acetonitrile;
(R,S) α-[1-(4-Isopropylbenzenesulfonyl)-1H-indol-3-yl]-α-(4-methylpiperazin-1-yl)-acetonitrile;
(R) α-[1-(4-Isopropylbenzenesulfonyl)-1H-indol-3-yl]-α-(4-methylpiperazin-1-yl)-acetonitrile;
(S) α-[1-(4-Isopropylbenzenesulfonyl)-1H-indol-3-yl]-α-(4-methylpiperazin-1-yl)-acetonitrile;
1-(Benzenesulfonyl)-3-(4-(benzyloxycarbonyl)-piperazin-1-ylmethyl)-1H-indole;
1-(Benzenesulfonyl)-3-(4H-piperazin-1-ylmethyl)-1H-indole;
1-(4-Methoxybenzenesulfonyl)-3-(4H-piperazin-1-ylmethyl)-1H-indole
1-(4-Isopropylbenzenesulfonyl)-3-(4H-piperazin-1-ylmethyl)-1H-indole
1-(2-Bromo-4-methoxybenzenesulfonyl)-3-(4H-piperazin-1-ylmethyl)-1H-indole
5-Bromo-1-(benzenesulfonyl)-3-(4H-piperazin-1-ylmethyl)-1H-indole;
5-Bromo-1-(4-methoxybenzenesulfonyl)-3-(4H-piperazin-1-ylmethyl)-1H-indole
5-Bromo-1-(4-isopropylbenzenesulfonyl)-3-(4H-piperazin-1-ylmethyl)-1H-indole
5-Bromo-1-(2-bromo-4-methoxybenzenesulfonyl)-3-(4H-piperazin-1-ylmethyl)-1H-indole
1-[[1-(4-Isopropylbenzenesulfonyl)-indol-3-yl]methyl][1,4]diazepane
1-[[1-(2-Bromo-4-methoxybenzenesulfonyl)-indol-3-yl]methyl][1,4]diazepane
1-[[1-(4-methylbenzenesulfonyl)-indol-3-yl]methyl][1,4]diazepane
1-[[5-Bromo-1-(4-Methoxybenzenesulfonyl)-indol-3-yl]methyl][1,4]diazepane
1-[[5-Bromo-1-(4-Isopropylbenzenesulfonyl)-indol-3-yl]methyl][1,4]diazepane
1-[[5-Bromo-1-(2-Bromo-4-methoxybenzenesulfonyl)-indol-3-yl]methyl][1,4]diazepane
1-[[5-Bromo-1-(4-methylbenzenesulfonyl)-indol-3-yl]methyl][1,4]diazepane and their isomers, polymers, pharmaceutically acceptable salts and solvates.

The present invention also envisages some useful bio-active metabolites of the compounds of general formula (I).

The present invention also provides novel intermediates involved in the preparation of compounds of formula (I). These include compound represented by general formulae (II) and (IV).

The compounds of general formula (I) of this invention are useful in the treatment and/or prophylaxis of a condition wherein modulation of 5-HT activity is desired.

The present invention provides for use of the compounds of general formula (I) according to above, for the manufacture of the medicaments for the potential use in the treatment and/or prophylaxis of certain CNS disorders such as, anxiety, depression, convulsive disorders, obsessive-compulsive disorders, migraine headache, cognitive memory disorders e.g. Alzheimer's disease and age-related cognitive decline, ADHD (Attention Deficient Disorder/Hyperactivity Syndrome), personality disorders, psychosis, paraphrenia, psychotic depression, mania, schizophrenia, schizophreniform disorders, withdrawal from drug abuse such as cocaine, ethanol, nicotine and benzodiazepines, panic attacks, sleep disorders (including disturbances of Circadian rhythm) and also disorders associated with spinal trauma and/or head injury such as hydrocephalus. Compounds of the invention are further expected to be of use in the treatment of mild cognitive impairment and other neurodegenerative disorders like Alzheimer's disease, Parkinsonism and Huntington's chorea.

The compounds of the invention are also expected to be of use in the treatment of certain GI (Gastrointestinal) disorders such as IBS (Irritable bowel syndrome) or chemotherapy induces emesis.

The compounds of the invention are also expected to be of use in the modulation of eating behavior, these compounds can also be used to reduce morbidity and mortality associated with the excess weight.

The present invention provides a method for the treatment of a human or a animal subject suffering from certain CNS disorders such as, anxiety, depression, convulsive disorders, obsessive-compulsive disorders, migraine headache, cognitive memory disorders e.g. Alzheimer's disease and age-related cognitive decline, ADHD (Attention Deficient Disorder/Hyperactivity Syndrome), personality disorders, psychosis, paraphrenia, psychotic depression, mania, schizophrenia, schizophreniform disorders, withdrawal from drug abuse such as cocaine, ethanol, nicotine and benzodiazepines, panic attacks, sleep disorders (including disturbances of Circadian rhythm) and also disorders associated with spinal trauma and/or head injury such as hydrocephalus. Compounds of the invention are further expected to be of use in the treatment of mild cognitive impairment and other neurodegenerative disorders like Alzheimer's disease, Parkinsonism and Huntington's chorea.

The present invention also provides a method for modulating 5-HT receptor function.

The present invention also includes a radiolabelled compounds of general formula (I) as a diagnostic tool for modulating 5-HT receptor function. Preferable radiolabelled tags include $^2H$, $^3H$, $^{13}C$, $^{14}C$, $^{125}I$, $^{15}N$, $^{31}P$, S.

An effective amount of a compound of general formula (I) or its salt is used for producing medicaments of the present invention, along with conventional pharmaceutical auxiliaries, carriers and additives.

The present invention also relates to a pharmaceutical composition for treating and/or prophylaxis of disorders, a condition wherein modulation of 5-HT is desired in a mammal, preferably a human, comprising:

a. a pharmaceutically acceptable carrier b. a compound of general formula (I) as defined above, c. a 5-HT re-uptake inhibitor, or a pharmaceutically acceptable salt thereof;

wherein the amounts of each active compound (a compound of general formula I and a 5-HT re-uptake inhibitor), is such that the combination is effective in treating such a condition.

The present invention also relates to a method of treatment and/or prophylaxis of disorders, a condition wherein modulation of 5-HT is desired in a mammal, preferably a human, comprising:

a. a pharmaceutically acceptable carrier b. a compound of general formula (I) as defined above, c. a 5-HT re-uptake inhibitor, or a pharmaceutically acceptable salt thereof;

wherein the amounts of each active compound (a compound of general formula (I) and a 5-HT re-uptake inhibitor), is such that the combination is effective in treating such a condition.

The present invention also relates to a process for the preparation of the above said novel compounds, their derivatives, their analogues, their tautomeric forms, their stereoisomers, their geometric forms, their N-oxides, their polymorphs, their pharmaceutically acceptable salts, their pharmaceutically acceptable solvates, and pharmaceutical compositions containing them.

The present invention also relates to novel intermediates involved in the preparation of the compounds of general formula (I) and the process/es for their preparation.

DETAILED DESCRIPTION OF THE INVENTION

The present invention relates to novel substituted N-arylsulfonyl-3substituted indoles of the general formula (I),

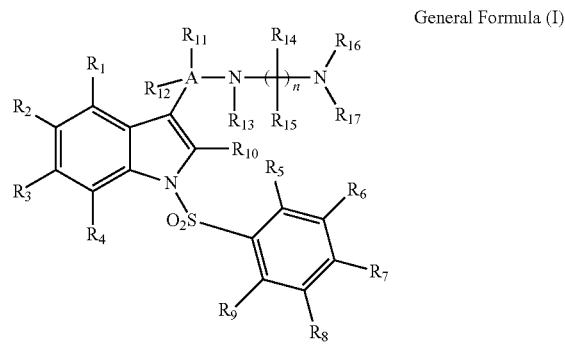

General Formula (I)

their derivatives, their analogs, their tautomeric forms, their stereoisomers, their geometric forms, their N-oxides, their polymorphs, their pharmaceutically acceptable salts and their pharmaceutically acceptable solvates, wherein A may be —$CH_2$—, —C=O or —$SO_2$—; $R_{11}$ and $R_{12}$, refer to substitutions on the carbon whenever A is $CH_2$; $R_1$, $R_2$, $R_3$, $R_4$, $R_5$, $R_6$, $R_7$, $R_8$, $R_9$, $R_{10}$, $R_{11}$, $R_{12}$, $R_{14}$ and $R_{15}$ may be same or different and each independently represent hydrogen, halogen, oxo, thio, perhaloalkyl, hydroxy, amino, nitro, cyano, formyl, amidino, guanidino, substituted or unsubstituted groups selected from linear or branched ($C_1$-$C_{12}$)alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$)alkoxy, cyclo($C_3$-$C_7$) alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino; aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ or $R_8$ and $R_9$ together with carbon atoms to which they are attached may form a five or a six membered ring, optionally containing one or more double bonds and optionally containing one or more heteroatoms selected from "Oxygen", "nitrogen", "Sulfur" or "Selenium" and combinations of double bond and heteroatoms; or $R_{11}$ and $R_{12}$ together with the carbon atoms to which they are attached may form a three to six membered ring, optionally containing one or more double bonds and optionally containing one or more heteroatoms selected from "Oxygen", "Nitrogen", "Sulfur" or "Selenium" and combinations of double bond and heteroatoms; $R_{13}$, $R_{16}$ and $R_{17}$ may be same or different and each independently represents Hydrogen, substituted or unsubstituted groups selected from linear or branched ($C_1$-$C_{12}$)alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, aryl, aralkyl, heteroaryl, heterocyclylalkyl; optionally $R_{13}$ along with either $R_{16}$ or $R_{17}$ and the two nitrogen atoms may form a 5, 6 7-membered heterocyclic ring, which may be further substituted with $R_{14}$ and $R_{15}$, and may have either one, two or three double bonds;

"n" is an integer ranging from 1 to 4, wherein the carbon chains which "n" represents may be either linear or branched.

Suitable groups represented by $R_1$, $R_2$, $R_3$, $R_4$, $R_5$, $R_6$, $R_7$, $R_8$, $R_9$, $R_{10}$, $R_{11}$, $R_{12}$, $R_{14}$ and $R_{15}$ wherever applicable may be selected from halogen atom such as fluorine, chlorine, bromine or iodine; perhaloalkyl particularly perhalo($C_1$-$C_6$) alkyl such as fluoromethyl, difluoromethyl, trifluoromethyl, trifluoroethyl, fluoroethyl, difluoroethyl and the like; substituted or unsubstituted ($C_1$-$C_{12}$)alkyl group, especially, linear or branched ($C_1$-$C_8$)alkyl group, such as methyl, ethyl, n-propyl, iso-propyl, n-butyl, iso-butyl, t-butyl, n-pentyl, iso-pentyl, hexyl, iso-hexyl, heptyl, octyl and the like; substituted or unsubstituted ($C_2$-$C_{12}$)alkenyl group such as ethylene, n-propylene pentenyl, hexenyl, heptynyl, heptadienyl and the like; ($C_2$-$C_{12}$)alkynyl substituted or unsubstituted ($C_2$-$C_{12}$)alkynyl group such as acetylene and the like; cyclo($C_3$-$C_7$)alkyl group such as cyclopropyl, cyclobutyl, cyclopentyl, cyclohexyl, cycloheptyl, the cycloalkyl group may be substituted; cyclo($C_3$-$C_7$)alkenyl group such as cyclopentenyl, cyclohexenyl, cycloheptynyl, cycloheptadienyl, cycloheptatrienyl and the like, the cycloalkenyl group may be substituted; ($C_1$-$C_{12}$) alkoxy, especially, ($C_1$-$C_6$)alkoxy group such as methoxy, ethoxy, propyloxy, butyloxy, iso-propyloxy and the like, which may be substituted; cyclo($C_3$-$C_7$) alkoxy group such as cyclopropyloxy, cyclobutyloxy, cyclopentyloxy, cyclohexyloxy, cycloheptyloxy and the like, the cycloalkoxy group may be substituted; aryl group such as phenyl or naphthyl, the aryl group may be substituted; aralkyl group such as benzyl, phenethyl, $C_6H_5CH_2CH_2CH_2$, naphthylmethyl and the like, the aralkyl group may be substituted and the substituted aralkyl is a group such as $CH_3C_6H_4CH_2$, $Hal$-$C_6H_4CH_2$, $CH_3OC_6H_4CH_2$, $CH_3OC_6H_4CH_2CH_2$ and the like; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, imidazolyl, oxadiazolyl, tetrazolyl, benzopyranyl, benzofuranyl and the like, the heteroaryl group may be substituted; heterocyclo($C_1$-$C_6$) alkyl, such as pyrrolidinylalkyl, piperidinylalkyl, morpholinylalkyl, thiomorpholinylalkyl, oxazolinylalkyl and the like, the heterocyclo($C_1$-$C_6$)alkyl group may be substituted; heteroaralkyl group such as furanylmethyl, pyridinylmethyl, oxazolylmethyl, oxazolylethyl and the like, the heteroaralkyl group may be substituted; heteroaryloxy, heteroaralkoxy, heterocycloalkoxy, wherein heteroaryl, heteroaralkyl, heterocycloalkyl and heterocyclylalkyl moieties are as defined earlier and may be substituted; acyl groups such as acetyl, propionyl or benzoyl, the acyl group may be substituted; acyloxy group such as $CH_3COO$, $CH_3CH_2COO$, $C_6H_5COO$ and the like which may optionally be substituted, acylamino group such as $CH_3CONH$, $CH_3CH_2CONH$, $C_3H_7CONH$, $C_6H_5CONH$ which may be substituted, $(C_1-C_6)$monoalkylamino group such as $CH_3NH$, $C_2H_5NH$, $C_3H_7NH$, $C_6H_{13}NH$ and the like, which may be substituted, $(C_1-C_6)$dialkylamino group such as $N(CH_3)_2$, $CH_3(C_2H_5)N$ and the like, which may be substituted; arylamino group such as $C_6H_5NH$, $CH_3(C_6H_5)N$, $C_6H_4(CH_3)NH$, $NH-C_6H_4$-Hal and the like, which may be substituted; arylalkylamino group such as $C_6H_5CH_2NH$, $C_6H_5CH_2CH_2NH$, $C_6H_5CH_2NCH_3$ and the like, which may be substituted; hydroxy$(C_1-C_6)$alkyl which may be substituted, amino$(C_1-C_6)$alkyl which may be substituted; mono $(C_1-C_6)$alkylamino$(C_1-C_6)$alkyl, di$(C_1-C_6)$alkylamino$(C_1-C_6)$alkyl group which may be substituted, alkoxyalkyl group such as methoxymethyl, ethoxymethyl, methoxyethyl, ethoxyethyl and the like, which may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; $(C_1-C_6)$alkylthio, thio$(C_1-C_6)$alkyl which may be substituted, alkoxycarbonylamino group such as $C_2H_5OCONH$, $CH_3OCONH$ and the like which may be substituted; aryloxycarbonylamino group as $C_6H_5OCONH$, $C_6H_5OCONCH_3$, $C_6H_5OCONC_2H_5$, $C_6H_4CH_3OCONH$, $C_6H_4(OCH_3)OCONH$ and the like which may be substituted; aralkoxycarbonylamino group such $C_6H_5CH_2OCONH$, $C_6H_5CH_2CH_2OCONH$, $C_6H_5CH_2OCON(CH_3)$, $C_6H_5CH_2OCON(C_2H_5)$, $C_6H_4CH_3CH_2OCONH$, $C_6H_4OCH_3CH_2OCONH$ and the like, which may be substituted; aminocarbonylamino group; $(C_1-C_6)$alkylaminocarbonylamino group, di$(C_1-C_6)$alkylaminocarbonylamino group; $(C_1-C_6)$alkylamidino group, $(C_1-C_6)$alkylguanidino, di$(C_1-C_6)$alkylguanidino groups, hydrazino and hydroxylamino groups; carboxylic acid or its derivatives such as amides, like $CONH_2$, alkylaminocarbonyl like $CH_3NHCO$, $(CH_3)_2NCO$, $C_2H_5NHCO$, $(C_2H_5)_2NCO$, arylaminocarbonyl like $PhNHCO$, $NapthylNHCO$ and the like, aralkylaminocarbonyl such as $PhCH_2NHCO$, $PhCH_2CH_2NHCO$ and the like, heteroarylaminocarbonyl and heteroaralkylamino carbonyl groups where the heteroaryl groups are as defined earlier, heterocyclylaminocarbonyl where the heterocyclyl group is as defined earlier, carboxylic acid derivatives such as esters, wherein the ester moieties are alkoxycarbonyl groups such as unsubstituted or substituted phenoxycarbonyl, naphthyloxycarbonyl and the like; aralkoxycarbonyl group such as benzyloxycarbonyl, phenethyloxycarbonyl, naphthylmethoxycarbonyl and the like, heteroaryloxycarbonyl, heteroaralkoxycarbonyl, wherein the heteroaryl group is as defined earlier, heterocycloxycarbonyl where heterocycle is as defined earlier and these carboxylic acid derivatives may be substituted; sulfonic acid or its derivatives such as $SO_2NH_2$, $SO_2NHCH_3$, $SO_2N(CH_3)_2$, $SO_2NHCF_3$, $SO_2NHCO(C_1-C_6)$alkyl, $SO_2NHCOaryl$ where the aryl group is as defined earlier and the sulfonic acid derivatives may be substituted; phosphoric acid and its derivatives as $P(O)(OH)_2$, $P(O)(OC_1-C_6$-alkyl$)_2$, $P(O)(O$-aryl$)_2$ and the like.

Suitable cyclic structures formed by the two adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ or $R_8$ and $R_9$ or $R_{11}$ and $R_{12}$ or $R_{14}$ and $R_{15}$ together with the carbon atoms to which they are attached contain 5 to 6 ring atoms which may optionally contain one or more heteroatoms selected from oxygen, nitrogen or sulfur and optionally contain one or more double bonds and optionally contain combination of double bond and hetero atoms as described earlier. The cyclic structures may be optionally substituted phenyl, naphthyl, pyridyl, furanyl, thienyl, pyrrolyl, imidazolyl, pyrimidinyl, pyrazinyl and the like. Suitable substituents on the cyclic structure formed by $R_1$ and $R_2$ or $R_2$ and $R_3$ or $R_3$ and $R_4$ or $R_5$ and $R_6$ or $R_6$ and $R_7$ or $R_7$ and $R_8$ or $R_8$ and $R_9$ or $R_{11}$ and $R_{12}$ together with the adjacent carbon atoms to which they are attached include oxo, hydroxy, halogen atom such as chlorine, bromine and iodine; nitro, cyano, amino, formyl, $(C_1-C_3)$alkyl, $(C_1-C_3)$alkoxy, thioalkyl, alkylthio, phenyl or benzyl groups.

$R_{13}$, $R_{16}$ and $R_{17}$ preferably represents hydrogen, substituted or unsubstituted linear or branched $(C_1-C_{12})$alkyl like methyl, ethyl, n-propyl, iso-propyl, n-butyl, iso-butyl, pentyl, hexyl, octyl and the like; aryl group such as phenyl or naphthyl, the aryl group may be substituted; cyclo$(C_3-C_7)$alkyl group such as cyclopropyl, cyclobutyl, cyclopentyl, cyclohexyl, cycloheptyl, the cycloalkyl group may be substituted; the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; $(C_3-C_7)$ cycloheteroalkyl with heteratoms like "Oxygen", "Nitrogen", "Sulfur" or "Selenium" optionally containing one or two double or triple bonds. Suitable hetero cyclic rings formed between $R_{13}$, and either of $R_{16}$ or $R_{17}$ be selected from imidazolyl, pyrimidinyl, pyrazinyl, piperazinyl, diazolinyl and the like, the heterocyclyl group may be substituted; heteroaryl group such as pyridyl, imidazolyl, tetrazolyl and the like, the heteroaryl group may be substituted; heterocyclo $(C_1-C_6)$alkyl, such as pyrrolidinealkyl, piperidinealkyl, morpholinealkyl, thiomorpholinealkyl, oxazolinealkyl and the like, the heterocyclo$(C_1-C_6)$alkyl group may be substituted; heteroaralkyl group such as furanmethyl, pyridinemethyl, oxazolemethyl, oxazolethyl and the like, the heteroaralkyl group may be substituted; heteroaryloxy, heteroaralkoxy, heterocycloalkoxy, wherein heteroaryl, heteroaralkyl, heterocycloalkyl and heterocyclylalkyl moieties are as defined earlier and may be further substituted.

In the case of the compounds of general formula (I) having an asymmetric carbon atom the present invention relates to the D-form, the L-form and D,L-mixtures and in the case of a number of asymmetric carbon atoms, the diastereomeric forms and the invention extends to each of these stereoisomeric forms and to mixtures thereof including racemates. Those compounds of general formula (I) which have an asymmetric carbon and as a rule are obtained as racemates can be separated one from the other by the usual methods, or any given isomer may, be obtained by stereospecific or asymmetric synthesis. However, it is also possible to employ an optically active compound from the start, a correspondingly optically active or diastereomeric compound then being obtained as the final compound.

In the case of the compounds of general formula (I), where tautomerism may exist, the present invention relates to all of the possible tautomeric forms and the possible mixture thereof.

In the case of the compounds of general formula (I) containing geometric isomerism the present invention relates to all of these geometric isomers.

Suitable pharmaceutically acceptable acid addition salts of compounds of the general formula (I) can be prepared of the aforementioned base compounds of this invention are those which form non-toxic acid addition salts, includes, salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benezenesulfonate, p-tolunesulfonate, palmoate and oxalate. Pharmaceutically acceptable salts forming part of this invention are intended to define few examples but not limited to the above list.

Suitable pharmaceutically acceptable base addition salts of compounds of the general formula (I) can be prepared of the aforementioned acid compounds of this invention are those which form non-toxic base addition salts, includes, salts containing pharmaceutically acceptable cations, such as Lithium, sodium, potassium, calcium and magnesium, salts of organic bases such as lysine, arginine, guanidine, diethanolamine, choline, tromethamine and the like; ammonium or substituted ammonium salts. Pharmaceutically acceptable salts forming part of this invention are intended to define few examples but not limited to the above list.

In addition, pharmaceutically acceptable salts of the compound of formula (I) can be obtained by converting derivatives which have tertiary amino groups into the corresponding quarternary ammonium salts in the methods known in the literature by using quarternizing agents. Possible quarternizing agents are, for example, alkyl halides such as methyl iodide, ethyl bromide and n-propyl chloride, including arylalkyl halides such as benzyl chloride or 2-phenylethyl bromide. Pharmaceutically acceptable salts forming part of this invention are intended to define few examples but not limited to the above list.

In the following description and reaction schemes $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, A and n are as defined previously and R is as defined elsewhere in the specification.

Compounds of general formula (I) can be prepared by any of the methods described below:

The present invention also provides processes for preparing compounds of general formula (I) as defined above, their derivatives, their analogs, their tautomeric forms, their stereoisomers, their geometric forms, their N-oxides, their polymorphs, their pharmaceutically acceptable salts, their pharmaceutically acceptable solvates and novel intermediates involved therein, which are as described below:

Scheme-1:

Compounds of general formula (I) wherein $A=-CR_{11}R_{12}-$, may be prepared by reacting a compound of formula (II) given below,

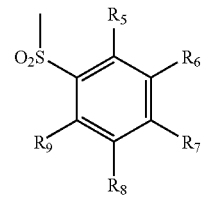

where $R_1$, $R_2$, $R_3$, $R_4$, $R_{10}$, $R_{11}$ and $R_{12}$ are as defined in relation to formula (I), further $R_{10}$ could be protected form thereof; R represents either of a suitable N-protecting group such as acetyl, triflouroacetyl, benzyl, trityl, t-butyloxycarbonyl (t-BOC) or a group such as,

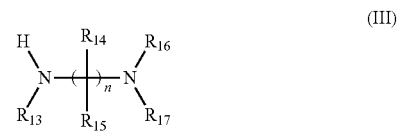

where $R_5$, $R_6$, $R_7$, $R_8$ and $R_9$ are as defined earlier, X is halogen, for example, a chloro, bromo or iodo; with a compound of formula (III) or its acid addition salt,

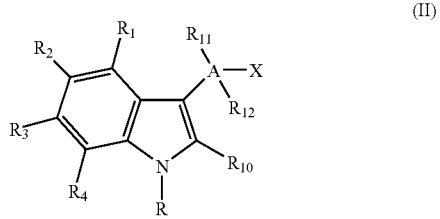

where $R_{13}$, $R_{14}$, $R_{15}$, $R_{16}$ and $R_{17}$ are as defined in relation to compound of formula (I) or precursor thereof; and thereafter if necessary:

i) converting a compound of the formula (I) into another compound of the formula (I); and/or
ii) removing any protecting groups; and/or
iii) forming a pharmaceutically acceptable salt or prodrug thereof.

Preferably the substituents selected for the compounds of formulae (II) and (III) are either inert to the reaction conditions or the sensitive groups are protected using suitable protecting groups. Whenever R is a suitable protecting group, an additional step as described in Scheme 2 is required to prepare compounds of formula (I).

The above reaction is preferably carried out in a solvent such as THF, acetone, DMF, xylene, toluene, methanol, ethanol, propanol and the like and preferably using either acetone or DMF. The inert atmosphere may be maintained by using inert gases such as $N_2$, Ar or He. The reaction mixture is generally heated to an elevated temperature or reflux temperature of the solvent, until the reaction is complete. A wide variety of acid-acceptor agents can be used in this condensation. However, preferred basic agents are sodium carbonate, sodium bicarbonate, potassium carbonate, sodium acetate, sodium alkoxides and the like, with a preferred basic agent being $K_2CO_3$. Reaction times of about 30 minutes to 72 hours are common. At the end of reaction, the volatile components are removed under reduced pressure. The reaction mixture can be optionally acidified before work-up. The product can be isolated by precipitation, washed, dried and further purified by standard methods such as recrystallization, column chromatography etc.

Optional steps (i), (ii) and (iii) can be carried out using conventional methods. These will depend upon the precise nature of the substituents on the indole in each case. Examples of suitable reactions are illustrated hereinafter.

Compounds represented by the general formula (II) are prepared by the method described elsewhere in the specification. Compounds of formula (III) are commercially available, or they may be prepared by conventional methods or by modification, using known processes, of commercially available compounds of formula (III).

Scheme-2:

Alternatively, compounds of formula (I) may be prepared by reacting a compound of formula (IV) given below,

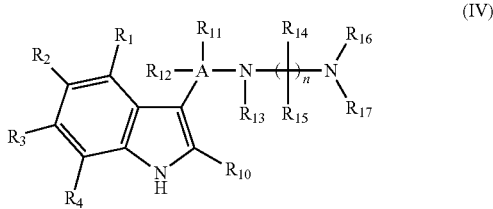

(IV)

wherein A, $R_1$, $R_2$, $R_3$, $R_4$, $R_{10}$, $R_{11}$, $R_{12}$, $R_{13}$, $R_{14}$, $R_{15}$, $R_{16}$ and $R_{17}$ are as defined in relation to formula (I), further $R_{10}$ could be protected form thereof; with a compound of formula (V),

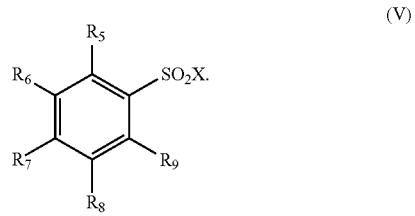

(V)

where $R_5$, $R_6$, $R_7$, $R_8$ and $R_9$, are as defined in relation to formula (I) and X is a halogeno, preferably chloro or bromo; and thereafter if desired or necessary carrying out steps (i), (ii) and/or (lii) as described above.

Preferably the substituents selected for the compounds of formula (IV) and (V) are either not affected by the reaction conditions or else the sensitive groups are protected using suitable protecting groups.

Compounds of formula (IV) and (V) are suitably reacted together in an inert organic solvent which includes, aromatic hydrocarbons such as toluene, o-, m-, p-xylene; halogenated hydrocarbons such as methylene chloride, chloroform, and chlorobenzene; ethers such as diethylether, diisopropyl ether, tert-butyl methyl ether, dioxane, anisole, and tetrahydrofuran; nitrites such as acetonitrile and propionitrile; ketones such as acetone, methyl ethyl ketone, diethyl ketone and tert-butyl methyl ketone; alcohols such as methanol, ethanol, n-propranol, n-butanol, tert-butanol and also DMF (N.N-dimethylformamide), DMSO (N.N-dimethyl sulfoxide) and water. The preferred list of solvents includes DMSO, DMF, acetonitrile and THF. Mixtures of these in varying ratios can also be used. Suitable bases are, generally, inorganic compounds such as alkali metal hydroxides and alkaline earth metal hydroxides, such as lithium hydroxide, sodium hydroxide, potassium hydroxide and calcium hydroxide; alkali metal oxides and alkaline earth metal oxides, lithium oxide, sodium oxide, magnesium oxide and calcium oxide; alkali metal hydrides and alkaline earth metal hydrides such as lithium hydride, sodium hydride, potassium hydride and calcium hydride; alkali metal amides and alkaline earth metal amides such as lithium amide, sodium amide, potassium amide and calcium amide; alkali metal carbonates and alkaline earth metal carbonates such as lithium carbonate and calcium carbonate; and also alkali metal hydrogen carbonates and alkaline earth metal hydrogen carbonates such as sodium hydrogen carbonate; organometallic compounds, particularly alkali-metal alkyls such as methyl lithium, butyl lithium, phenyl lithium; alkyl magnesium halides such as methyl magnesium chloride and alkali metal alkoxides and alkaline earth metal alkoxides such as sodium methoxide, sodium ethoxide, potassium ethoxide, potassium tert-butoxide and di-methoxymagnesium, further more organic bases e.g. triethylamine, triisopropylamine, and N-methylpiperidine, pyridine. Sodium hydroxide, Sodium methoxide, Sodium ethoxide, potassium hydroxide potassium carbonate and tri-ethylamine are especially preferred. Suitably the reaction may be effected in the presence of phase transfer catalyst such as tetra-n-butylammonium hydrogen sulphate and the like. The inert atmosphere may be maintained by using inert gases such as $N_2$, Ar or He. Reaction times may vary from 1 to 24 hrs, preferably from 2 to 6 hours, whereafter, if desired, the resulting compound is continued into a salt thereof.

Compounds of formula (V) are commercially available, or they may be prepared by conventional methods or by modification, using known processes, of commercially available compounds of formula (V).

Scheme-3:

Compounds of general formula (I) may be prepared by reacting a compound of formula (VI) given below,

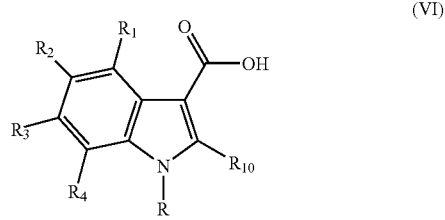

(VI)

Where $R_1$, $R_2$, $R_3$, $R_4$, and $R_{10}$ are as defined in relation to formula (I), further $R_{10}$ could be protected form thereof; R represents either of a suitable N-protecting group such as acetyl, triflouroacetyl, or a group such as,

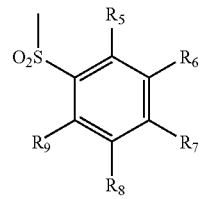

where $R_5$, $R_6$, $R_7$, $R_8$ and $R_9$ are as defined earlier, X is a halogeno, for example a chloro, bromo or iodo; with a compound of formula (III) or its acid addition salt,

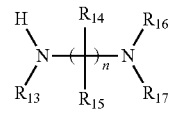

(III)

where $R_{13}$, $R_{14}$, $R_{15}$, $R_{16}$ and $R_{17}$ are as defined in relation to compound of formula (I) or precursor thereof; by standard peptide coupling for example using bis(2-oxo-3-oxazolidinyl) phosphoric chloride (BOP-Cl) and thereafter if desired or necessary carrying out steps (i), (ii) and/or (lii) as described above.

Scheme-4:

In this method N,N'-thionyl-diimidazole is first prepared by reacting imidazole with thionyl chloride. The former is then reacted with the compound of formula (VI) N-(substituted indolyl)alkanoic acid and the resulting N-(substituted indolyl-alkanoyl)imidazole is reacted with N-substituted amine compound of formula (III). If desired the N,N'-thionyl-diimidazole and N-(substituted indolyl-alkanoyl)imidazole intermediates can be isolated prior to the next reaction in the succeeding step, but it is advantageous to carry out the entire sequence of steps upto formation of N-(substituted indolyl-alkanoyl)-4-substituted-amine in essentially one operation, that is by reacting each intermediate without isolation with the next succeeding reactant using the same solvent medium for the entire sequence of reactions. Suitable solvents are organic solvents inert under the conditions of the reactions, for example tetrahydrofuran, diethylether, dibutylether and the like. The reactions are preferably conducted at a temperature in the range from about −10° C. to about 50° C.

Amide intermediates can be reduced to the desired compound of formula (I), wherein A=-CH$_2$—, by the use of reducing agents capable of converting the amido functionality to an amino moiety. Such agents are, for example, lithium aluminum hydride or other complex aluminum hydrides. The reducing reactions are, performed in diethyl ether or tetrahydrofuran, or in a stable diborane complex such as borantetrahydrofuran or borane-dimethylsulphide or others (J. Org. Chem. 1982, 47, 1389) used in an appropriate solvent (e.g. tetrahydrofuran). Many other useful reducing agents are known to those skilled in the art (March J., Advanced Organic Chemistry, Wiley Interscience Ed., 1992, 1212).

Scheme-5:

Compounds of general formula (I) may be prepared by reacting a compound of formula (VII) given below,

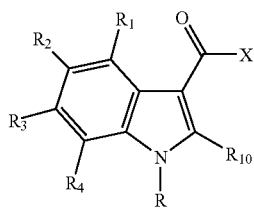

(VII)

wherein $R_1$, $R_2$, $R_3$, $R_4$ and $R_{10}$ are as defined in relation to formula (I), X is a halogeno, for example a chloro, bromo or iodo; while R represents either of a suitable N-protecting group such as acetyl, triflouroacetyl, benzyl, trityl, t-butyloxycarbonyl (t-BOC) or a group such as,

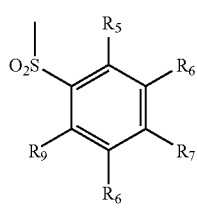

where $R_5$, $R_6$, $R_7$, $R_8$ and $R_9$ are as defined earlier, with a compound of formula (III) or its acid addition salt,

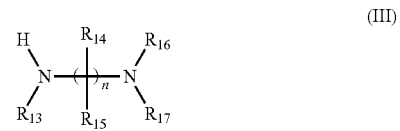

(III)

where $R_{13}$, $R_{14}$, $R_{15}$, $R_{16}$ and $R_{17}$ are as defined in relation to compound of formula (I) or precursor thereof; in suitable anhydrous solvent; and thereafter if desired or necessary carrying out steps (i), (ii) and/or (lii) as described above.

The reaction is preferably carried out at a temperature in the range from about −5° C. to about 65° C., in the presence of acid acceptor in an organic solvent inert under the conditions of the reactions, for example tetrahydrofuran, diethylether, ethylene chloride and the like. The purpose of acid acceptor is to take up the hydrogen halide which is split out during the course of the reaction and includes sodium carbonate, sodium bicarbonate, potassium carbonate, sodium acetate, sodium alkoxides and the like. The acid acceptor can also be in the form of an excess quantity of substituted amine.

Scheme-6:

Compounds of general formula (I) may be prepared by reacting a compound of formula (VIII) or its salt,

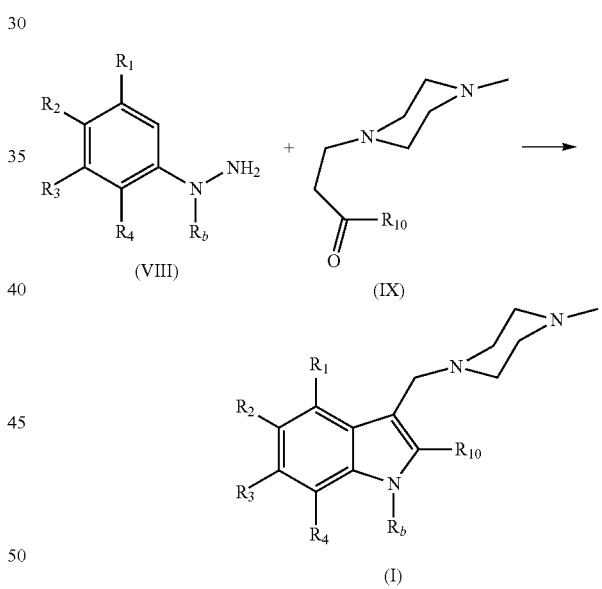

with the ketone amine compound of formula (IX), and thereafter if desired or necessary carrying out steps (i), (ii) and/or (lii) as described above.

The process comprises of reacting the phenyl hydrazine compound of formula (VIII) or its salt with the ketone amine compound of formula (IX) in presence of suitable solvent and an acid catalyst. The reaction may be carried out at temperature ranging between 60° C. to the reflux temperature of the solvent/s used, for about half-hour to 4 hours. Optionally, water formed in the reaction may be removed using the techniques known in the art. The reaction may be conducted in an inert atmosphere.

Suitable acid catalysts include mineral acids as well as organic acids, characterized in that glacial acetic acid, perchloric acid, trifluoroacetic acid, trichloroacetic acid, monochloroacetic acid, benzenesulfonic acid, hydrochloric acid, hydrobromic acid, sulfuric acid, phosphoric acid, orthophosphoric acid, polyphosphoric acid and the like. Optionally Lewis acids such as aluminum chloride, titanium tetrachloride, zinc chloride etc. can be used as a catalyst in some cases. Suitable mechanism for removing water from a reaction mixture includes those described in the literature and known to a skilled artisan. Dehydrating agents such as sulfuric acid, molecular sieves, or removing water by azeotropic distillation are examples of techniques described in the prior art. Suitable solvents for the phenyl hydrazine of formula (VIII) or its salt include ethers, alcohols, nitroalkanes, acetonitrile, dimethylsulfoxide, dimethyl formamide, and hexamethylphosphoramide. While suitable solvents for the ketone amine of formula (IX) includes inert solvents, such as, hydrocarbons, chlorinated hydrocarbons or acyclic ethers and the mixtures thereof.

Scheme-7:

Compounds of general formula (I) where A=-CHCN— and derivatives thereof may be prepared by reacting a compound of formula (X) given below,

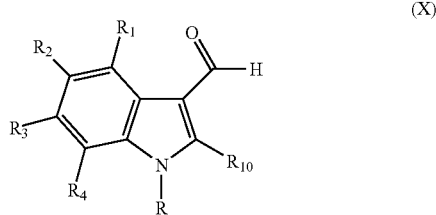

wherein $R_1$, $R_2$, $R_3$, $R_4$ and $R_{10}$ are as defined in relation to formula (I), while R represents a group such as,

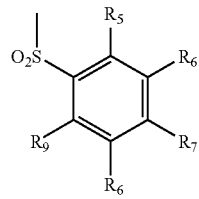

where $R_5$, $R_6$, $R_7$, $R_8$ and $R_9$ are as defined earlier, is added to aqueous solution of sodium bisulfite and reacted with a compound of formula (III) or its acid addition salt,

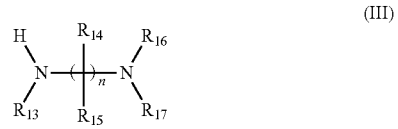

where $R_{13}$, $R_{14}$, $R_{15}$, $R_{16}$ and $R_{17}$ are as defined in relation to compound of formula (I) or precursor thereof; in the presence of sodium cyanide, in suitable aqueous solvent; and thereafter if desired or necessary carrying out steps (i), (ii) and/or (lii) as described above.

Scheme-8:

Alternatively, the compounds of formula (I) where A=-CH$_2$—, can be obtained by carrying out reduction of the compounds of formula (I) where A=-CO— using the known procedures.

During any of the above synthetic sequences it may be necessary and/or desirable to protect sensitive or reactive groups on any of the molecules concerned. This may be achieved by means of conventional protecting groups, such as those described in Protective Groups in Organic Chemistry, Ed J. F. W. McOmie, Plenum Press, 1973, and T. W. Greene & P. G. M. Wuts, Protective Groups in Organic Synthesis, John Wiley & Sons, 1991. For example, suitable protecting groups for the piperazine group include BOC, COCCl$_3$, COCF$_3$. The protecting groups may be removed according to the standard procedures.

N-substituted piperazines, can be prepared by acylation or alkylation of the appropriate NH-piperazine compound according to the standard procedures.

The protecting groups may be removed at a convenient subsequent stage using methods known from the art The compounds of the present invention may contain one or more asymmetric centers and therefore exist as stereoisomers. The stereoisomers of the compounds of the present invention may be prepared by one or more ways presented below:

i) One or more of the reagents may be used in their optically active form.

ii) Optically pure catalyst or chiral ligands along with metal catalyst may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).

iii) The mixture of stereoisomers may be resolved by conventional methods such as forming a diastereomeric salts with chiral acids or chiral amines, or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).

iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. Examples given above for chiral acids and bass are only examples and in no circumstances limit the scope of the invention for other chiral reagents.

The pharmaceutically acceptable salts forming a part of this invention may be prepared by treating the compound of formula (I) with 1-6 equivalents of a base such as lithium, ammonia, substituted ammonia, sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used. Organic bases such lysine, arginine, methyl benzylamine, ethanolamine, diethanolamine, tromethamine, choline, guanidine and their derivatives may be used. Acid addition salts, wherever applicable may be prepared by treatment with acids such as tartaric acid, mandelic acid, fumaric acid, maleic acid, lactic acid, salicyclic acid, citric acid, ascorbic acid, benzene sulfonic acid, p-toluene sulfonic acid, hydroxynaphthoic acid, methane sulfonic acid, malic acid, acetic acid, benzoic acid, succinic acid, palmitic acid, oxalic acid, hydrochloric acid, hydrobromic acid, sulfuric acid, nitric acid and the like in solvents such as water, alcohols, ethers, ethyl acetate, dioxane, DMF or a lower alkyl ketone such as acetone, or the mixtures thereof.

Different polymorphs of the compounds defined in this invention of general formula (I) may be prepared by crystallization of compounds of general formula (I) under different conditions such as different solvents or solvent mixtures in varying proportions for recrystallization, various ways of crystallization such as slow cooling, fast cooling or a very fast cooling or a gradual cooling during crystallization. Different polymorphs may also be obtained by heating the compound, melting the compound and solidification by gradual or fast cooling, heating or melting under vacuum or under inert atmosphere and cooling under either vacuum or inert atmosphere. The various polymorphs may be identified by either one or more of the following techniques such as differential scanning calorimeter, powder X-ray diffraction, IR spectroscopy, solid probe NMR spectroscopy and thermal microscopy.

According to a feature of the present invention, there are novel intermediates of formula represented by general formula (II) and (IV), which are useful in the preparation of compounds of formula (I).

Novel intermediates of general formula (II) are represented as given below,

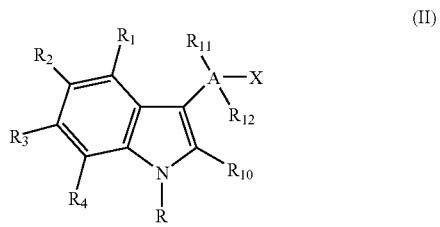

(II)

where $R_1$, $R_2$, $R_3$, $R_4$, $R_{10}$, $R_{11}$ and $R_{12}$, may be same or different and each independently represent hydrogen, halogen, oxo, thio, perhaloalkyl, hydroxy, amino, nitro, cyano, formyl, amidino, guanidino, substituted or unsubstituted groups selected from linear or branched $(C_1$-$C_{12})$alkyl, $(C_2$-$C_{12})$alkenyl, $(C_2$-$C_{12})$alkynyl, $(C_3$-$C_7)$cycloalkyl, $(C_3$-$C_7)$cycloalkenyl, bicycloalkyl, bicycloalkenyl, $(C_1$-$C_{12})$alkoxy, cyclo$(C_3$-$C_7)$alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ together with carbon atoms to which they are attached may form a five or a six membered ring, optionally containing one or more double bonds and optionally containing one or more heteroatoms selected from "Oxygen", "Nitrogen", "Sulfur" or "Selenium" and combinations of double bond and heteroatoms; or $R_{11}$ and $R_{12}$ together with the carbon atoms to which they are attached may form a three to six membered ring, optionally containing one or more double bonds and optionally containing one or more heteroatoms selected from "oxygen", "Nitrogen", "Sulfur" or "Selenium" and combinations of double bond and heteroatoms; further $R_1$, $R_2$, $R_3$, $R_4$, $R_{11}$, and $R_{12}$ could be a protected form thereof, especially for groups such as amino and its derivatives hydroxyl, carboxylic acid and its derivatives, sulfonic adds and its derivatives, phosphoric acid and its derivatives and the like;

R represents either of hydrogen or a suitable N-protecting group such as acetyl, triflouroacetyl, benzyl, trityl, t-butyloxycarbonyl (t-BOC) or a group such as,

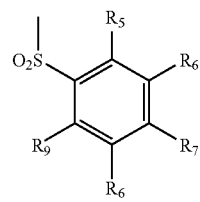

and X is halogen, for example a chloro, bromo or iodo.

The present invention also provides a process for preparing the novel intermediate represented by the general formula (II) from another novel compound of general formula (XI).

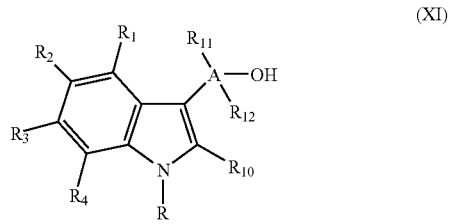

(XI)

where $R_1$, $R_2$, $R_3$, $R_4$, $R_{10}$, $R_{11}$ and $R_{12}$, are as defined in relation with the compounds of general formula (II), by halogenation using halogenating reagent like thionyl chloride according to the methods known in the art.

The compounds of general formula (XI) can be prepared by first protecting indole nitrogen preferably with aryl sulfonyl group and then carrying out reduction using sodium borohydride as described elsewhere in the specification.

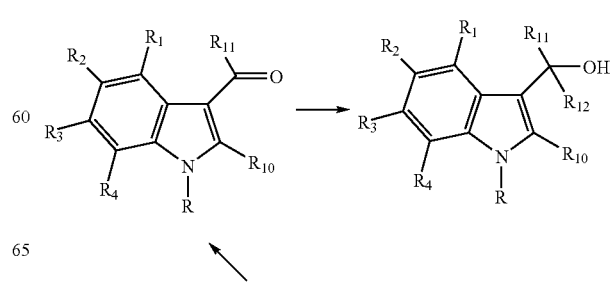

-continued

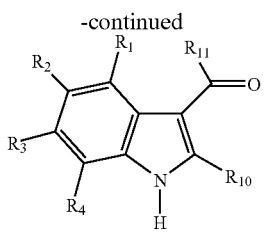

Novel intermediate of general formula (IV) are represented as given below,

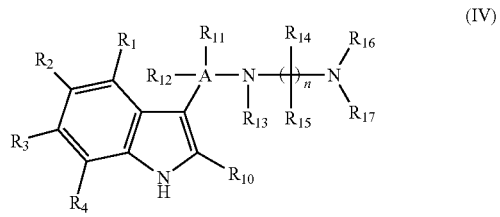

(IV)

wherein A may be —CH$_2$—, —C=O or —SO$_2$—; $R_{11}$ and $R_{12}$, refer to substitutions on the carbon whenever A is CH$_2$; $R_1$, $R_2$, $R_3$, $R_4$, $R_{10}$, $R_{11}$, $R_{12}$, $R_{14}$ and $R_{15}$ may be same or different and each independently represent hydrogen, halogen, oxo, thio, perhaloalkyl, hydroxy, amino, nitro, cyano, formyl, amidino, guanidino, substituted or unsubstituted groups selected from linear or branched (C$_1$-C$_{12}$) alkyl, (C$_2$-C$_{12}$)alkenyl, (C$_2$-C$_{12}$)alkynyl, (C$_3$-C$_7$)cycloalkyl, (C$_3$-C$_7$)cycloalkenyl, bicycloalkyl, bicycloalkenyl, (C$_1$-C$_{12}$)alkoxy, cyclo(C$_3$-C$_7$)alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_5$ and $R_6$ or $R_6$ and $R_7$ or $R_7$ and $R_8$ or $R_8$ and $R_9$ together with carbon atoms to which they are attached may form a five or a six membered ring, optionally containing one or more double bonds and optionally containing one or more heteroatoms selected from "Oxygen", "Nitrogen", "Sulfur" or "Selenium" and combinations of double bond and heteroatoms; or $R_{11}$ and $R_{12}$ together with the carbon atoms to which they are attached may form a three to six membered ring, optionally containing one or more double bonds and optionally containing one or more heteroatoms selected from "Oxygen", "Nitrogen", "Sulfur" or "Selenium" and combinations of double bond and heteroatoms; further $R_1$, $R_2$, $R_3$, $R_4$, $R_{11}$, $R_{12}$, $R_{14}$ and $R_{15}$ could be a protected form thereof, especially for groups such as amino and its derivatives, hydroxyl, carboxylic acid and its derivatives, sulfonic acids and its derivatives, phosphoric acid and its derivatives and the like;

$R_{13}$, $R_{16}$ and $R_{17}$ may be same or different and each independently represents Hydrogen, substituted or unsubstituted groups selected from linear or branched (C$_1$-C$_{12}$)alkyl, (C$_2$-C$_{12}$)alkenyl, (C$_2$C$_{12}$)alkynyl, (C$_3$-C$_7$)cycloalkyl, (C$_3$-C$_7$)cycloalkenyl, bicycloalkyl, bicycloalkenyl, aryl, aralkyl, heteroaryl, heterocyclylalkyl; optionally $R_{13}$ along with either $R_{16}$ or $R_{17}$ and the two nitrogen atoms may form a 5, 6 or 7-membered heterocyclic ring, which may be further substituted with $R_{14}$ and $R_{15}$, and may have either one, two or three double bonds;

"in" is an integer ranging from 1 to 4, wherein the carbon chains which "n" represents may be either linear or branched.

The present invention also provides a process for preparing the novel intermediate represented by the general formula (IV).

When A=CH$_2$ in the compounds of formula (IV), such compounds may be suitably prepared by according to the method described in Scheme 1, by reacting the compound of formula (II) wherein R is H or toluenesulfonyl group, with the compound of formula (III).

Compounds of formula (II), wherein R=H can be obtained from corresponding compounds of formula (II) wherein R=p-toluenesulfonyl group, benzyl and the like. These are also N-protecting groups which could be removed according to the known methods.

Alternatively, compounds of formula (IV), wherein R is particularly hydrogen can be prepared from other compounds of formula (IV), wherein R is preferably an alkanoyl radical having 2-4 carbon atoms, wherein $R_1$, $R_2$, $R_3$, $R_4$, $R_{10}$, $R_{11}$, $R_{12}$, $R_{13}$, $R_{14}$, $R_{15}$, $R_{16}$, and $R_{17}$ are as defined in relation to formula (I), in a suitable solvent such as methanol or ethanol, with a basic agent, preferably an amine, ammonia or an alkali metal hydroxide, whereafter, if desired, the resulting compound is converted into a salt thereof. Conversion of hydroxyl groups to leaving groups is a conventional procedure for those skilled in the art.

When A=-CH(CN)—, the compounds of formula (IV), may be prepared by carrying out reaction described in Scheme 7 on substituted indole derivative (R=H) under similar conditions.

When A=-CH(CH$_3$)— or —C(CH$_3$)$_2$— the compounds of formula (IV), may be prepared from the corresponding examples by removing tosyl group from the compounds of formula (I). Thus, other derivatives of novel intermediates (IV) and further compounds of formula (I) can be obtained.

In an another method compounds of formula (IV) where A=-CH$_2$— may be prepared by reacting a compound of formula (XII)

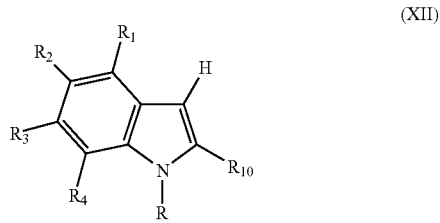

(XII)

where $R_1$, $R_2$, $R_3$, $R_4$ and $R_{10}$ are as defined in relation to formula (I), $R_{10}$ could also be protected form thereof; R is hydrogen, with a compound of formula (III) given below and formaldehyde,

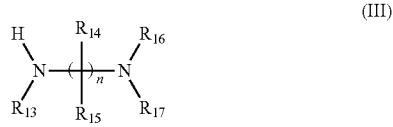

(III)

wherein $R_{13}$, $R_{14}$, $R_{15}$, $R_{16}$ and $R_{17}$ are as defined earlier.

The above reaction is preferably carried out at a temperature of 50° C. to 150° C., the formaldehyde can be in the form of as aqueous solution i.e. 40% formalin solution, or a polymeric form of formaldehyde such as paraformaldehyde or trioxymethylene. When such polymeric forms are used, a molar excess of mineral acid, for example hydrochloric acid, is added to regenerate the free aldehyde from the polymer. The reaction is preferably carried in an organic solvent inert to the conditions of the reaction, such as methanol, ethanol or 3-methylbutanol and the like or a mixture thereof, and preferably using either acetone or DMF. The inert atmosphere may be maintained by using inert gases such as $N_2$, Ar or He. The reaction may be affected in the presence of a base such as $K_2CO_3$, $Na_2CO_3$, NaH or mixtures thereof. The reaction temperature may range from 20° C. to 150° C. based on the choice of solvent and preferably at a temperature in the range from 30° C. to 100° C. The duration of the reaction may range from 1 to 24 hours, preferably from 2 to 6 hours.

Another aspect of the present invention comprises of a pharmaceutical composition, containing at least one of the compounds of the general formula (I), their derivatives, their analogs, their tautomeric forms, their stereoisomers, their geometric forms, their N-oxides, their polymorphs, their pharmaceutically acceptable salts, their pharmaceutically acceptable solvates thereof as an active ingredient, together with pharmaceutically employed carriers, auxiliaries and the like.

The pharmaceutical compositions of the present invention may be formulated in a conventional manner using one or more pharmaceutically acceptable carriers. Thus, the active compounds of the invention may be formulated for oral, buccal, intranasal, parental (e.g., intravenous, intramuscular or subcutaneous) or rectal administration or a form suitable for administration by inhalation or insufflation.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose,. microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer, or from a capsule using a inhaler or insufflator. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule it preferably should be in the form of powder. Capsules and cartridges (made, for example, from gelatin) for use in an inhaler or insufflator may be formulated containing a powder mix of a compound of the invention and a suitable powder base such as lactose or starch.

A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

The affinities of the compound of this invention for the various serotonin receptors are evaluated using standard radioligand binding assays and are described here in these specification.

Biological Activity Assay Methods:

Assay: $5HT_{1A}$:

Materials and Methods:

Receptor Source: Human recombinant expressed in HEK-293 cells

Radioligand: [3H]-8-OH-DPAT (221 Ci/mmol)
Final ligand concentration—[0.5 nM]
Reference Compound: 8-OH-DPAT
Positive Control: 8-OH-DPAT
Incubation Conditions: Reactions are carried out in 50 mM TRIS-HCl (pH 7.4) containing 10 mM $MgSO_4$, 0.5 mM EDTA and 0.1% Ascorbic acid at room temperature for 1 hour. The reaction is terminated by rapid vacuum filtration onto glass fiber filters. Radioactivity trapped onto the filters is determined and compared to control values in order to ascertain any interactions of test compound with the $5HT_{1A}$ binding site.

Literature Reference:
Hoyer D., Engel G., et al. Molecular Pharmacology of $5HT_1$ and $5-HT_2$ Recognition Sites in Rat and Pig Brain Membranes: Radioligand Binding Studies with [$^3$H]-5HT, [$^3$H]-8-OH-DPAT, [$^{125}$I]-Iodocyanopindolol, [$^3$H]-Mesulergine and [$^3$H]-Ketanserin. Eur. Jml. Pharmacol. 118: 13-23 (1985) with modifications.
Schoeffter P. and Hoyer D. How Selective is GR 43175? Interactions with Functional $5-HT_{1A}$, $5HT_{1B}$, $5-HT_{1C}$, and $5-HT_{1D}$ Receptors. Naunyn-Schmiedeberg's Arch. Pharmac. 340: 135-138 (1989) with modifications.

Assay: $5HT_{1B}$
Materials and Methods:
Receptor Source: Rat striatal membranes
Radioligand: [$^{125}$I]Iodocyanopindolol (2200 Ci/mmol)
Final ligand concentration—[0.15 nM]
Non-specific Determinant:Serotonin—[10 µM]
Reference Compound: Serotonin
Positive Control: Serotonin
Incubation Conditions: Reactions are carried out in 50 mM TRIS-HCl (pH 7.4) containing 60 µM (-) isoproterenol at 37° C. for 60 minutes. The reaction is terminated by rapid vacuum filtration onto glass fiber filters. Radioactivity trapped onto the filters is determined and compared to control values in order to ascertain any interactions of test compound with the $5HT_{1B}$ binding site.

Literature Reference:
Hoyer D., Engel G., et al. Molecular Pharmacology of $5HT_1$ and $5-HT_2$ Recognition Sites in Rat and Pig Brain Membranes: Radioligand Binding Studies with [$^3$H]-5HT, [$^3$H]-8-OH-DPAT, [$^{125}$I]-Iodocyanopindolol, [$^3$H]-Mesulergine and [$^3$H]-Ketanserin. Eur. Jml. Pharmacol. 118: 13-23 (1985) with modifications.
Schoeffter P. and Hoyer D. How selective is GR 43175? Interactions with Functional $5-HT_{1A}$, $5HT_{1B}$, $5-HT_{1C}$, and $5HT_1$ Receptors. Naunyn-Schmiedeberg's Arch. Pharmac. 340: 135-138 (1989) with modifications.

Assay: $5HT_{1D}$
Materials and Methods:
Receptor Source: Human cortex
Radioligand: [$^3$H] 5-Carboxamidotryptamine (20-70 Ci/mmol)
Final ligand concentration—[2.0 nM]
Non-specific Determinant: 5-Carboxamidotryptamine (5-CT)—[1.0 µM]
Reference Compound: 5-Carboxamidotryptamine (5-CT)
Positive Control: 5-Carboxamidotryptamine (5-CT)
Incubation Conditions: Reactions are carried out in 50 mM TRIS-HCl (pH 7.7) containing 4 mM $CaCl_2$, 100 nM 8-OH-DPAT, 100 nM Mesulergine, 10 uM Pargyline and 0.1% ascorbic acid at 250 C. for 60 minutes. The reaction is terminated by rapid vacuum filtration onto glass fiber filters. Radioactivity trapped onto the filters is determined and compared to control values in order to ascertain any interactions of test compound with the cloned $5HT_{1D}$ binding site.

Literature Reference:
Waeber C., Schoeffter, Palacios J. M. and Hoyer D. Molecular Pharmacology of the $5-HT_{1D}$ Recognition Sites: Radioligand Binding Studies in Human, Pig, and Calf Brain Membranes. Naunyn-Schmiedeberg's Arch. Pharmacol. 337: 595-601 (1988) with modifications.

Assay: $5HT_{2A}$
Materials and Methods:
Receptor Source: Human Cortex
Radioligand: [$^3$H] Ketanserin (60-90 Ci/mmol)
Final ligand concentration—[2.0 nM]
Non-specific Determinant: Ketanserin—[3.0 µM]
Reference Compound: Ketanserin
Positive Control: Ketanserin
Incubation Conditions: Reactions are carried out in 50 mM TRIS-HCl (pH 7.5) at room temperature for 90 minutes. The reaction is terminated by rapid vacuum filtration onto glass fiber filters. Radioactivity trapped onto the filters is determined and compared to control values in order to ascertain any interactions of test compound with the $5HT_{2A}$ binding site.

Literature Reference:
Leysen J. E., Niemegeers C. J., Van Nueten J. M. and Laduron P. M. [$^3$H]Ketanserin: A Selective Tritiated Ligand for Serotonin$_2$ Receptor Binding Sites. Mol. Pharmacol. 21: 301-314 (1982) with modifications.
Martin, G. R. and Humphrey, P. P. A. Classification Review: Receptors for 5-HT: Current Perspectives on Classification and Nomenclature. Neuropharmacol. 33(3/4): 261-273 (1994).

Assay: $5HT_{2C}$
Materials and Methods:
Receptor Source: Pig choroid plexus membranes
Radioligand: [$^3$H] Mesulergine (50-60 Ci/mmol)
Final ligand concentration—[1.0 nM]
Non-specific Determinant: Serotonin—[100 µM]
Reference Compound: Mianserin
Positive Control: Mianserin
Incubation Conditions: Reactions are carried out in 50 mM TRIS-HCl (pH 7.7) containing 4 mM $CaCl_2$ and 0.1% ascorbic acid at 37° C. for 60 minutes. The reaction is terminated by rapid vacuum filtration onto glass fiber filters. Radioactivity trapped onto the filters is determined and compared to control values in order to ascertain any interactions of test compound with the $5HT_{2C}$ binding site.

Literature Reference:
A. Pazos, D. Hoyer, and J. Palacios. The Binding of Serotonergic Ligands to the Porcine Choroid Plexus: Characterization of a New Type of Serotonin Recognition Site. Eur. Jml. Pharmacol. 106: 539-546 (1985) with modifications.
Hoyer, D., Engel, G., et al. Molecular Pharmacology of $5HT_1$ and $5-HT_2$ Recognition Sites in Rat and Pig Brain Membranes: Radioligand Binding Studies with [3H]-5HT, [3H]-8-OH-DPAT, [$^{125}$I]-Iodocyanopindolol, [3H]-Mesulergine and [3H]-Ketanserin. Eur. Jml. Pharmacol. 118: 13-23 (1985) with modifications.

Assay: $5HT_3$
Materials and Methods:
Receptor Source: N1E-115 cells
Radioligand:[$^3$H]-GR 65630 (30-70 Ci/mmol)
Final ligand concentration—[0.35 nM]

Non-specific Determinant MDL-72222—[1.0 µM]
Reference Compound: MDL-72222
Positive Control: MDL-72222

Incubation Conditions: Reactions are carried out in 20 mM HEPES (pH 7.4) containing 150 mM NaCl at 25° C. for 60 minutes. The reaction is terminated by rapid vacuum filtration onto glass fiber filters. Radioactivity trapped onto the filters is determined and compared to control values in order to ascertain any interactions of test compound with the $5HT_3$ binding site.

Literature Reference:
Lummis S. C. R., Kilpatrick G. J. Characterization of $5HT_3$ Receptors in Intact N1E-115 Neuroblastoma Cells. Eur. Jml. Pharmacol. 189: 223-227 (1990) with modifications.
Hoyer D. and Neijt H. C. Identification of Serotonin 5-$HT_3$ Recognition Sites in Membranes of N1E-115 Neuroblastoma Cells by Radioligand Binding. Mol. Pharmacol. 33: 303 (1988).
Tyers M. B. 5-$HT_3$ Receptors and the Therapeutic Potential of $5HT_3$ Receptor Antagonists. Therapie. 46: 431435 (1991).

Assay: $5HT_4$
Materials and Methods:
Receptor Source: Guinea pig striatal membranes
Radioligand: [$^3$H] GR-113808 (30-70 Ci/mmol)
Final ligand concentration—[0.2 nM]
Non-specific Determinant: Serotonin (5-HT)—[30 µM]
Reference Compound: Serotonin (5-HT)
Positive Control: Serotonin (5-HT)

Incubation Conditions: Reactions are carried out in 50 mM HEPES (pH 7.4) at 370 C. for 60 minutes. The reaction is terminated by rapid vacuum filtration onto glass fiber filters. Radioactivity trapped onto the filters is determined and compared to control values in order to ascertain any interactions of test compound with the $5HT_4$ binding site.

Literature Reference:
Grossman Kilpatrick, C., et al. Development of a Radioligand Binding Assay for $5HT_4$ Receptors in Guinea Pig and Rat Brain. Brit Jml. Phamacol. 109: 618-624 (1993).

Assay: $5HT_{5A}$
Materials and Methods:
Receptor Source: Human recombinant expressed in HEK 293 cells
Radioligand: [$^3$H] LSD (60-87 Ci/mmol)
Final ligand concentration—[1.0 nM]
Non-specific Determinant: Methiothepin mesylate—[1.0 µM]
Reference Compound: Methiothepin mesylate
Positive Control: Methiothepin mesylate Incubation Conditions: Reactions are carried out in 50 mM TRIS-HCl (pH 7.4) containing 10 mM $MgSO_4$ and 0.5 mM EDTA at 37° C. for 60 minutes. The reaction is terminated by rapid vacuum filtration onto glass fiber filters. Radioactivity trapped onto the filters is determined and compared to control values in order to ascertain any interactions of test compound with the cloned $5HT_{5A}$ binding site.

Literature Reference:
Rees S., et al. FEBS Letters, 355: 242-246 (1994) with modifications Assay: $5HT_6$
Materials and Methods:
Receptor Source: Human recombinant expressed in HEK293 cells
Radioligand: [$^3$H]LSD (60-80 Ci/mmol)
Final ligand concentration—[1.5 nM]
Non-specific Determinant: Methiothepin mesylate—[0.1 µM]
Reference Compound: Methiothepin mesylate
Positive Control: Methiothepin mesylate Incubation Conditions: Reactions are carried out in 50 mM TRIS-HCl (pH 7.4) containing 10 mM $MgCl_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound (s) with the cloned serotonin—$5HT_6$ binding site.

Literature Reference:
Monsma F. J. Jr., et al., Molecular Cloning and Expression of Novel Serotonin Receptor with High Affinity for Tricyclic Psychotropic Drugs. Mol. Pharmacol. (43): 320-327 (1993).

Assay: $5-HT_7$
Materials and Methods:
Receptor Source: Human recombinant expressed in CHO cells
Radioligand: [$^3$H]LSD (60-80 Ci/mmol)
Final ligand concentration—[2.5 nM]
Non-specific Determinant: 5-carboxamidotryptamine (5-CT)—[0.1 µM]
Reference Compound: 5-carboxamidotryptamine
Positive Control: 5-carboxamidotryptamine Incubation Conditions: Reactions are carried out in 50 mM TRIS-HCl (pH 7.4) containing 10 mM $MgCl_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound (s) with the cloned serotonin—$5HT_7$ binding site.

Literature Reference:
Y. Shen, E. Monsma, M. Metcalf, P. Jose, M Hamblin, D. Sibley, Molecular Cloning and Expression of a 5-hydroxytryptamine7 Serotonin Receptor Subtype. J. Biol. Chem. 268:18200-18204.

The following examples illustrate the preparation of the compounds of the present invention. These are provided by the way of illustration only and therefore should not be construed to limit the scope of the invention. Commercial reagents were utilized without further purification. Room temperature refers to 25-30° C. Melting points are uncorrected. IR spectra were taken using KBr and in solid state. Unless otherwise stated, all mass spectra were carried out using ESI conditions. $^1$H NMR spectra were recorded at 200 MHz on a Bruker instrument. Deuterated chloroform (99.8% D) was used as solvent. TMS was used as internal reference standard. Chemical shift values are expressed in are reported in parts per million (δ)-values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet NMR, mass were corrected for background peaks. Specific rotations were measured at room temperature using the sodium D (589 nm). Chromatography refers to column chromatography performed using 60-120 mesh silica gel and executed under nitrogen pressure (flash chromatography) conditions.

Description 1

1-Benzenesulfonyl-1H-indole-3-carboxaldehyde

A stirred solution of 1H-indole-3-carboxaldehyde (1 g, 6.89 mmol), in DMF (25 mL) was treated with sodium hydride (0.357 g, 60% in mineral oil, 8.95 mmol) under nitrogen at room temperature, stirred for 30 minutes, treated with benzene sulfonyl chloride (1.09 mL, 8.25 mmol), stirred at room temperature for 3-5 hrs. After the completion of reaction (T. L. C.), the reaction mixture was quenched with 25 mL ice-cold water and diluted with 25 mL ethyl acetate. The organic phase was separated, washed sequentially with water and brine, dried over anhydrous $MgSO_4$ and concentrated in vacuo. The resultant residue was purified by flash chromatography (silica gel, EtOAc/Hexane, 2/8) to afford the title compound as an off-white foam, which was latter identified by IR, NMR and mass spectral data.

Description 2-48 (D2-D50)

Using essentially the same procedure described in description 1 hereinabove, the compounds given in the list 1 below were obtained by employing either an appropriate indole-3-carboxaldehyde or 3-acetylindole and substituted arylsulfonylchloride. The compounds obtained were identified by IR, NMR and mass spectral data.

List-1

| | Description | Mass Ion $(M + H)^+$ |
|---|---|---|
| D1 | 1-Benzenesulfonyl-1H-indole-3-carboxaldehyde | 286 |
| D2 | 1-Benzenesulfonyl-5-bromo-1H-indole-3-carboxaldehyde | 364 |
| D3 | 1-Benzenesulfonyl-5-chloro-1H-indole-3-carboxaldehyde | 320 |
| D4 | 1-Benzenesulfonyl-5-methoxy-1H-indole-3-carboxaldehyde | 316 |
| D5 | 1-Benzenesulfonyl-5-nitro-1H-indole-3-carboxaldehyde | 331 |
| D6 | 1-(4-Methylbenzenesulfonyl)-1H-indole-3-carboxaldehyde | 300 |
| D7 | 5-Bromo-1-(4-methylbenzenesulfonyl)-1H-indole-3-carboxaldehyde | 378 |
| D8 | 5-Chloro-1-(4-methylbenzenesulfonyl)-1H-indole-3-carboxaldehyde | 334 |
| D9 | 1-(4-Methylbenzenesulfonyl)-5-methoxy-1H-indole-3-carboxaldehyde | 330 |
| D10 | 1-(4-Methylbenzenesulfonyl)-5-nitro-1H-indole-3-carboxaldehyde | 345 |
| D11 | 1-(4-Methoxybenzenesulfonyl)-1H-indole-3-carboxaldehyde | 316 |
| D12 | 5-Bromo-1-(4-methoxybenzenesulfonyl)-1H-indole-3-carboxaldehyde | 394 |
| D13 | 5-Chloro1-(4-methoxybenzenesulfonyl)-1H-indole-3-carboxaldehyde | 350 |
| D14 | 1-(4-Methoxybenzenesulfonyl)-5-methoxy-1H-indole-3-carboxaldehyde | 346 |
| D15 | 1-(4-Methoxybenzenesulfonyl)-5-nitro-1H-indole-3-carboxaldehyde | 361 |
| D16 | 1-(4-Fluorobenzenesulfonyl)-1H-indole-3-carboxaldehyde | 304 |
| D17 | 5-Bromo-1-(4-fluorobenzenesulfonyl)-1H-indole-3-carboxaldehyde | 382 |
| D18 | 5-Chloro-1-(4-fluorobenzenesulfonyl)-1H-indole-3-carboxaldehyde | 338 |
| D19 | 1-(4-Fluorobenzenesulfonyl)-5-methoxy-1H-indole-3-carboxaldehyde | 334 |
| D20 | 1-(4-Fluorobenzenesulfonyl)-5-nitro-1H-indole-3-carboxaldehyde | 349 |
| D21 | 1-(4-Bromobenzenesulfonyl)-1H-indole-3-carboxaldehyde | 364 |
| D22 | 5-Bromo-1-(4-bromobenzenesulfonyl)-1H-indole-3-carboxaldehyde | 442 |
| D23 | 1-(4-Bromobenzenesulfonyl)-5-chloro-1H-indole-3-carboxaldehyde | 398 |
| D24 | 1-(4-Bromobenzenesulfonyl)-5-methoxy-1H-indole-3-carboxaldehyde | 394 |
| D25 | 1-(4-Bromobenzenesulfonyl)-5-nitro-1H-indole-3-carboxaldehyde | 409 |
| D26 | 1-(4-Isopropylbenzenesulfonyl)-1H-indole-3-carboxaldehyde | 328 |
| D27 | 5-Bromo-1-(4-isopropylbenzenesulfonyl)-1H-indole-3-carboxaldehyde | 406 |
| D28 | 5-Chloro-1-(4-isopropylbenzenesulfonyl)-1H-indole-3-carboxaldehyde | 362 |
| D29 | 1-(4-Isopropylbenzenesulfonyl)-5-methoxy-1H-indole-3-carboxaldehyde | 358 |
| D30 | 1-(4-Isopropylbenzenesulfonyl)-5-nitro-1H-indole-3-carboxaldehyde | 373 |
| D31 | 1-(2-Bromobenzenesulfonyl)-1H-indole-3-carboxaldehyde | 364 |
| D32 | 5-Bromo-1-(2-bromobenzenesulfonyl)-1H-indole-3-carboxaldehyde | 442 |
| D33 | 1-(2-Bromobenzenesulfonyl)-5-chloro-1H-indole-3-carboxaldehyde | 398 |
| D34 | 1-(2-Bromobenzenesulfonyl)-5-methoxy-1H-indole-3-carboxaldehyde | 394 |
| D35 | 1-(2-Bromobenzenesulfonyl)-5-nitro-1H-indole-3-carboxaldehyde | 409 |
| D36 | 1-(2-Bromo-4-methoxybenzenesulfonyl)-1H-indole-3-carboxaldehyde | 394 |
| D37 | 5-Bromo-1-(2-bromo-4-methoxybenzenesulfonyl)-1H-indole-3-carboxaldehyde | 472 |
| D38 | 1-(2-Bromo-4-methoxybenzenesulfonyl)-5-chloro-1H-indole-3-carboxaldehyde | 428 |
| D39 | 1-(2-Bromo-4-methoxybenzenesulfonyl)-5-methoxy-1H-indole-3-carboxaldehyde | 424 |
| D40 | 1-(2-Bromo-4-methoxybenzenesulfonyl)-5-nitro-1H-indole-3-carboxaldehyde | 439 |

-continued

List-1

| | Description | Mass Ion (M + H)+ |
|---|---|---|
| D41 | 1-(3,5-Dimethyl-3H-isoxazole-2-sulfonyl)-1H-indole-3-carbaldehyde | 305 |
| D42 | 5-Bromo-1-(3,5-dimethyl-3H-isoxazole-2-sulfonyl)-1H-indole-3-carboxaldehyde | 382 |
| D43 | 5-Chloro-1-(3,5-dimethylisoxazole-4-sulfonyl)-1H-indole-3-carboxaldehyde | 339 |
| D44 | 1-(3,5-Dimethylisoxazole-4-sulfonyl)-5-methoxy-1H-indole-3-carboxaldehyde | 335 |
| D45 | 1-(3,5-Dimethylisoxazole-4-sulfonyl)-5-nitro-1H-indole-3-carboxaldehyde | 350 |
| D46 | 1-(1-Benzenesulfonyl-1H-indol-3-yl)ethanone | 300 |
| D47 | 1-(5-Bromo-1-benzenesulfonyl-1H-indol-3-yl)ethanone | 378 |
| D48 | 1-(1-(4-Methylbenzenesulfonyl)-1H-indol-3-yl)ethanone | 330 |
| D49 | 1-(1-(4-Methoxybenzenesulfonyl)-1H-indol-3-yl)ethanone | 330 |
| D50 | 1-(1-(4-Isopropylbenzenesulfonyl)-1H-indol-3-yl)ethanone | 342 |

Description 51

1-Benzenesulfonyl-1H-indol-3-ylmethanol (D 51)

In a three necked round bottom flask equipped with pressure equalizing funnel, 1-Benzenesulfonyl-1H-indole-3-carboxaldehyde (D1, 2.86 g, 0.01 mole) and dichloromethane (8 mL) were taken. Sodiumborohydride (0.005-0.01 mole) was added slowly at room temperature and the reaction mixture was stirred well for next 3-4 hours. After the completion of reaction (TLC, 3-5 hours), the product was isolated by distillation under reduced pressure. The residue was extracted with ethyl acetate (2×25 mL). The combined organic extracts were washed with water, followed by brine, dried over anhydrous sodium sulfate. The organic layer was evaporated under vacuum. The residue was generally an oily liquid, which was isolated and purified by flash chromatography (silica gel, EtOAc/Hexane, 2/8) to afford the title compound, which was identified by IR, NMR and mass spectral analyses.

Description 52-100 (D52-D100)

Using essentially the same procedure described in description 51 hereinabove and employing an appropriate arylsulfonylindolyl-3-carboxaldehyde (D2-D50) along with sodium hydride other derivatives were prepared and identified by IR, NMR and mass spectral analyses. The compounds, thus prepared, are given in the list 2 below.

List-2

| | Description | Mass Ion (M − H)− |
|---|---|---|
| D51 | 1-Benzenesulfonyl-1H-indol-3-ylmethanol | 286 |
| D52 | 1-Benzenesulfonyl-5-bromo-1H-indole-3-ylmethanol | 364 |
| D53 | 1-Benzenesulfonyl-5-chloro-1H-indole-3-ylmethanol | 320 |
| D54 | 1-Benzenesulfonyl-5-methoxy-1H-indole-3-ylmethanol | 316 |
| D55 | 1-Benzenesulfonyl-5-nitro-1H-indole-3-ylmethanol | 331 |
| D56 | 1-(4-Methylbenzenesulfonyl)-1H-indole-3-ylmethanol | 300 |
| D57 | 5-Bromo-1-(4-methylbenzenesulfonyl)-1H-indole-3-ylmethanol | 378 |
| D58 | 5-Chloro-1-(4-methylbenzenesulfonyl)-1H-indole-3-ylmethanol | 334 |
| D59 | 1-(4-Methylbenzenesulfonyl)-5-methoxy-1H-indole-3-ylmethanol | 330 |
| D60 | 1-(4-Methylbenzenesulfonyl)-5-nitro-1H-indole-3-ylmethanol | 345 |
| D61 | 1-(4-Methoxybenzenesulfonyl)-1H-indole-3-ylmethanol | 316 |
| D62 | 5-Bromo-1-(4-methoxybenzenesulfonyl)-1H-indole-3-ylmethanol | 394 |
| D63 | 5-Chloro1-(4-methoxybenzenesulfonyl)-1H-indole-3-ylmethanol | 350 |
| D64 | 1-(4-Methoxybenzenesulfonyl)-5-methoxy-1H-indole-3-ylmethanol | 346 |
| D65 | 1-(4-Methoxybenzenesulfonyl)-5-nitro-1H-indole-3-ylmethanol | 361 |
| D66 | 1-(4-Fluorobenzenesulfonyl)-1H-indole-3-ylmethanol | 304 |
| D67 | 5-Bromo-1-(4-fluorobenzenesulfonyl)-1H-indole-3-ylmethanol | 382 |
| D68 | 5-Chloro-1-(4-fluorobenzenesulfonyl)-1H-indole-3-ylmethanol | 338 |
| D69 | 1-(4-Fluorobenzenesulfonyl)-5-methoxy-1H-indole-3-ylmethanol | 334 |
| D70 | 1-(4-fluorobenzenesulfonyl)-5-nitro-1H-indole-3-ylmethanol | 349 |
| D71 | 1-(4-Bromobenzenesulfonyl)-1H-indole-3-ylmethanol | 364 |
| D72 | 5-Bromo-1-(4-bromobenzenesulfonyl)-1H-indole-3-ylmethanol | 442 |
| D73 | 1-(4-Bromobenzenesulfonyl)-5-chloro-1H-indole-3-ylmethanol | 398 |
| D74 | 1-(4-Bromobenzenesulfonyl)-5-methoxy-1H-indole-3-ylmethanol | 363 |
| D75 | 1-(4-Bromobenzenesulfonyl)-5-nitro-1H-indole-3-ylmethanol | 409 |
| D76 | 1-(4-Isopropylbenzenesulfonyl)-1H-indole-3-ylmethanol | 328 |
| D77 | 5-Bromo-1-(4-isopropylbenzenesulfonyl)-1H-indole-3-ylmethanol | 406 |
| D78 | 5-Chloro-1-(4-isopropylbenzenesulfonyl)-1H-indole-3-ylmethanol | 362 |
| D79 | 1-(4-Isopropylbenzenesulfonyl)-5-methoxy-1H-indole-3-ylmethanol | 368 |

-continued

List-2

| | Description | Mass Ion (M − H)⁻ |
|---|---|---|
| D80 | 1-(4-Isopropylbenzenesulfonyl)-5-nitro-1H-indole-3-ylmethanol | 373 |
| D81 | 1-(2-Bromobenzenesulfonyl)-1H-indole-3-ylmethanol | 364 |
| D82 | 5-Bromo-1-(2-bromobenzenesulfonyl)-1H-indole-3-ylmethanol | 442 |
| D83 | 1-(2-Bromobenzenesulfonyl)-5-chloro-1H-indole-3-ylmethanol | 398 |
| D84 | 1-(2-Bromobenzenesulfonyl)-5-methoxy-1H-indole-3-ylmethanol | 394 |
| D85 | 1-(2-Bromobenzenesulfonyl)-5-nitro-1H-indole-3-ylmethanol | 409 |
| D86 | 1-(2-Bromo-4-methoxybenzenesulfonyl)-1H-indole-3-ylmethanol | 393 |
| D87 | 5-Bromo-1-(2-bromo-4-methoxybenzenesulfonyl)-1H-indole-3-ylmethanol | 472 |
| D88 | 1-(2-Bromo-4-methoxybenzenesulfonyl)-5-chloro-1H-indole-3-ylmethanol | 428 |
| D89 | 1-(2-Bromo-4-methoxybenzenesulfonyl)-5-methoxy-1H-indole-3-ylmethanol | 424 |
| D90 | 1-(2-Bromo-4-methoxybenzenesulfonyl)-5-nitro-1H-indole-3-ylmethanol | 439 |
| D91 | 1-(3,5-dimethylisoxazole-4-sulfonyl)-1H-indole-3-ylmethanol | 305 |
| D92 | 5-Bromo-1-(3,5-dimethylisoxazole-4-sulfonyl)-1H-indole-3-ylmethanol | 382 |
| D93 | 5-Chloro-1-(3,5-dimethylisoxazole-4-sulfonyl)-1H-indole-3-ylmethanol | 339 |
| D94 | 1-(3,5-Dimethylisoxazole-4-sulfonyl)-5-methoxy-1H-indole-3-ylmethanol | 335 |
| D95 | 1-(3,5-Dimethylisoxazole-4-sulfonyl)-5-nitro-1H-indole-3-ylmethanol | 350 |
| D96 | (RS) 1-(1-Benzenesulfonyl-1H-indol-3-yl)ethan-1-ol** | 283* |
| D97 | (RS) 1-(5-Bromo-1-benzenesulfonyl-1H-indol-3-yl)ethan-1-ol** | 361* |
| D98 | (RS) 1-(1-(4-Methylbenzenesulfonyl)-1H-indol-3-yl)ethan-1-ol** | 297* |
| D99 | (RS) 1-(1-(4-Methoxybenzenesulfonyl)-1H-indol-3-yl)ethan-1-ol** | 313* |
| D100 | (RS) 1-(1-(4-Isopropylbenzenesulfonyl)-1H-indol-3-yl)ethan-1-ol** | 325* |

*Molecular ion obtained corresponded to (M-18).
**The chiral intermediates obtained herein, may be separated by using known procedures as described earlier.

Description 101 (D101)

1-Benzenesulfonyl-3-chloromethyl-1H-indole

In a three necked round bottom flask equipped with pressure equalizing funnel, substituted (1-Benzenesulfonyl-1H-indol-3-yl)methanol (D51, 2.87 g, 0.01 mole) and dichloromethane (8 mL) were taken. Thionyl chloride (1.584 g, 0.012 mole) was added slowly at room temperature and the reaction mixture was stirred well for one hour. After the completion of reaction (TLC), the product was isolated by distillation under reduced pressure. The residue was extracted with ethyl acetate (2×25 mL). The combined organic extracts were washed with water, followed by brine, dried over anhydrous sodium sulfate. The organic layer was evaporated under vacuum. The residue obtained was further triturated with n-hexane to afford a solid material, which was identified by IR, NMR and mass spectral analyses as the title compound.

Description 102-150 (D102-D150)

Using essentially the same procedure described in description 101 hereinabove and employing appropriately substituted arylsulfonylindolyl methanol (prepared as given in D51-D100), the corresponding chloro compounds were prepared, and are given in the list 3 below. These compounds were identified by IR, NMR and mass spectral analyses.

List-3

| | Description | Mass Ion (M + H)⁺ |
|---|---|---|
| D101 | 1-Benzenesulfonyl-3-chloromethyl-1H-indole | 306 |
| D102 | 1-Benzenesulfonyl-5-bromo-3-chloromethyl-1H-indole | 384 |
| D103 | 1-Benzenesulfonyl-5-chloro-3-chloromethyl-1H-indole | 340 |
| D104 | 1-Benzenesulfonyl-5-methoxy-3-chloromethyl-1H-indole | 336 |
| D105 | 1-Benzenesulfonyl-5-nitro-3-chloromethyl-1H-indole | 351 |
| D106 | 1-(4-Methylbenzenesulfonyl)-3-chloromethyl-1H-indole | 320 |
| D107 | 5-Bromo-1-(4-methylbenzenesulfonyl)-3-chloromethyl-1H-indole | 398 |
| D108 | 5-Chloro-1-(4-methylbenzenesulfonyl)-3-chloromethyl-1H-indole | 354 |
| D109 | 1-(4-Methylbenzenesulfonyl)-5-methoxy-3-chloromethyl-1H-indole | 350 |
| D110 | 1-(4-Methylbenzenesulfonyl)-5-nitro-3-chloromethyl-1H-indole | 365 |
| D111 | 1-(4-methoxybenzenesulfonyl)-3-chloromethyl-1H-indole | 336 |
| D112 | 5-Bromo-1-(4-methoxybenzenesulfonyl)-3-chlorormethyl-1H-indole | 414 |
| D113 | 5-Chloro1-(4-methoxybenzenesulfonyl)-3-chloromethyl-1H-indole | 370 |

-continued

List-3

| | Description | Mass Ion (M + H)+ |
|---|---|---|
| D114 | 1-(4-methoxybenzenesulfonyl)-5-methoxy-3-chloromethyl-1H-indole | 366 |
| D115 | 1-(4-methoxybenzenesulfonyl)-5-nitro-3-chloromethyl-1H-indole | 381 |
| D116 | 1-(4-Fluorobenzenesulfonyl)-3-chloromethyl-1H-indole | 324 |
| D117 | 5-Bromo-1-(4-fluorobenzenesulfonyl)-3-chloromethyl-1H-indole | 402 |
| D118 | 5-Chloro-1-(4-fluorobenzenesulfonyl)-3-chloromethyl-1H-indole | 358 |
| D119 | 1-(4-Fluorobenzenesulfonyl)-5-methoxy-3-chloromethyl-1H-indole | 354 |
| D120 | 1-(4-fluorobenzenesulfonyl)-5-nitro-3-chloromethyl-1H-indole | 369 |
| D121 | 1-(4-Bromobenzenesulfonyl)-3-chloromethyl-1H-indole | 384 |
| D122 | 5-Bromo-1-(4-bromobenzenesulfonyl)-3-chloromethyl-1H-indole | 462 |
| D123 | 1-(4-Bromobenzenesulfonyl)-5-chloro-3-chloromethyl-1H-indole | 418 |
| D124 | 1-(4-Bromobenzenesulfonyl)-5-methoxy-3-chloromethyl-1H-indole | 414 |
| D125 | 1-(4-Bromobenzenesulfonyl)-5-nitro-3-chloromethyl-1H-indole | 429 |
| D126 | 1-(4-Isopropylbenzenesulfonyl)-3-chloromethyl-1H-indole | 348 |
| D127 | 5-Bromo-1-(4-isopropylbenzenesulfonyl)-3-chloromethyl-1H-indole | 426 |
| D128 | 5-Chloro-1-(4-isopropylbenzenesulfonyl)-3-chloromethyl-1H-indole | 382 |
| D129 | 1-(4-Isopropylbenzenesulfonyl)-5-methoxy-3-chloromethyl-1H-indole | 388 |
| D130 | 1-(4-Isopropylbenzenesulfonyl)-5-nitro-3-chloromethyl-1H-indole | 393 |
| D131 | 1-(2-Bromobenzenesulfonyl)-3-chloromethyl-1H-indole | 384 |
| D132 | 5-Bromo-1-(2-bromobenzenesulfonyl)-3-chloromethyl-1H-indole | 462 |
| D133 | 1-(2-Bromobenzenesulfonyl)-5-chloro-3-chloromethyl-1H-indole | 418 |
| D134 | 1-(2-Bromobenzenesulfonyl)-5-methoxy-3-chloromethyl-1H-indole | 414 |
| D135 | 1-(2-Bromobenzenesulfonyl)-5-nitro-3-chloromethyl-1H-indole | 429 |
| D136 | 1-(2-Bromo-4-methoxybenzenesulfonyl)-3-chloromethyl-1H-indole | 414 |
| D137 | 5-Bromo-1-(2-bromo-4-methoxybenzenesulfonyl)-3-chloromethyl-1H-indole | 492 |
| D138 | 1-(2-Bromo-4-methoxybenzenesulfonyl)-5-chloro-3-chloromethyl-1H-indole | 448 |
| D139 | 1-(2-Bromo-4-methoxybenzenesulfonyl)-5-methoxy-3-chloromethyl-1H-indole | 444 |
| D140 | 1-(2-Bromo-4-methoxybenzenesulfonyl)-5-nitro-3-chloromethyl-1H-indole | 459 |
| D141 | 1-(3,5-dimethylisoxazole-4-sulfonyl)-3-(1-chloromethyl)-1H-indole | 325 |
| D142 | 5-Bromo-1-(3,5-dimethylisoxazole-4-sulfonyl)-3-(1-chloromethyl)-1H-indole | 402 |
| D143 | 5-Chloro-1-(3,5-dimethylisoxazole-4-sulfonyl)-3-(1-chloromethyl)-1H-indole | 359 |
| D144 | 1-(3,5-Dimethylisoxazole-4-sulfonyl)-5-methoxy-3-(1-chloromethyl)-1H-indole | 355 |
| D145 | 1-(3,5-Dimethylisoxazole-4-sulfonyl)-5-nitro-3-(1-chloromethyl)-1H-indole | 370 |
| D146 | (R,S) 1-Benzenesulfonyl-3-(1-chloroethyl)-1H-indole** | 320 |
| D147 | (R,S) 5-Bromo-1-benzenesulfonyl-3-(1-chloroethyl)-1H-indole** | 398 |
| D148 | (R,S) 1-(4-Methylbenzenesulfonyl)-3-(1-chloroethyl)-1H-indole** | 334 |
| D149 | (R,S) 1-(4-Methyoxybenzenesulfonyl)-3-(1-chloroethyl)-1H-indole** | 350 |
| D150 | (RS) 1-(4-Isopropylbenzenesulfonyl)-3-(1-chloroethyl)-1H-indole** | 362 |

**If desired, the chiral intermediates may be separated by using known procedures in the art as described earlier.

Description 151 (D151)

3-(4-Methylpiperazin-1-ylmethyl)-1H-indole

In a three necked round bottom flask equipped with pressure equalizing funnel, indole (1.17 g, 0.01 mole) and dichloromethane (8 mL) were taken. 1-Methylpiperazine (1.01 g, 0.011 moles) and formaldehyde (9 mL, 0.012 mole) was added slowly at room temperature and the reaction mixture was stirred well for one hour. After the completion of reaction (TLC), the product was isolated by distillation under reduced pressure. The residue was extracted with ethyl acetate (2×25 mL). The combined organic extracts were washed with water, followed by brine, dried over anhydrous sodium sulfate. The organic layer was evaporated under vacuum. The residue could either be an oily liquid or solid mass. The oily mass was triturated with n-hexane to obtain a solid material. The solid obtained was identified by IR, NMR and mass spectral analyses.

Description 152-173 (D152-D173)

Using essentially the same procedure described in description 151 hereinabove and employing appropriately substituted indole along with either of substituted alkyl piperazine, substituted aryl piperazine, N,N,N'-trimethylethylene-1,2-diamine or homopiperazine compounds given in the list 4 were prepared. The structure of compounds thus obtained were confirmed by IR, NMR and mass spectral analyses.

Similarly unsubstituted piperazine can be prepared which may be needed to be protected later prior to sulfonylation.

List-4

| | Description | Mass Ion (M + H)+ |
|---|---|---|
| D151 | 3-(4-Methylpiperazin-1-ylmethyl)-1H-indole | 230 |
| D152 | 5-Bromo-3-(4-methylpiperazin-1-ylmethyl)-1H-indole | 308 |
| D153 | 5-Chloro-3-(4-methylpiperazin-1-ylmethyl)-1H-indole | 264 |
| D154 | 5-Methoxy-3-(4-methylpiperazin-1-ylmethyl)-1H-indole | 260 |
| D155 | 5-Nitro-3-(4-methylpiperazin-1-ylmethyl)-1H-indole | 273 |
| D156 | 3-(4H-Piperazin-1-ylmethyl)-1H-indole | 216 |
| D157 | 3-(4-(1-Methoxyphen-2-yl)piperazin-1-ylmethyl)-1H-indole | 322 |
| D158 | 5-Bromo-3-(4-(1-methoxyphen-2-yl)piperazin-1-ylmethyl)-1H-indole | 408 |
| D159 | 5-Methoxy-3-(4-(1-methoxyphen-2-yl)piperazin-1-ylmethyl)-1H-indole | 352 |
| D160 | 3-(4-(Pyridin-2-yl)piperazin-1-ylmethyl)-1H-indole | 293 |
| D161 | 5-Bromo-3-(4-(pyridin-2-yl)piperazin-1-ylmethyl)-1H-indole | 371 |
| D162 | 5-Methoxy-3-(4-(pyridin-2-yl)piperazin-1-ylmethyl)-1H-indole | 323 |
| D163 | 5-Chloro-2-methyl-3-(4-methylpiperazin-1-ylmethyl)-1H-indole | 327 |
| D164 | N-(1H-Indol-3-ylmethyl)-N,N',N'-trimethylethylene-1,2-diamine | 232 |
| D165 | 5-Bromo-N-(1H-indol-3-ylmethyl)-N,N',N'-trimethylethylene-1,2-diamine | 310 |
| D166 | 5-Nitro-N-(1H-indol-3-ylmethyl)-N,N',N'-trimethylethylene-1,2-diamine | 275 |
| D167 | 3-(4-Methylpiperazin-1-ylmethyl)-2-methyl-1H-indole | 244 |
| D168 | 5-Fluoro-3-(4-methylpiperazin-1-ylmethyl)-2-methyl-1H-indole | 262 |
| D169 | 5-Chloro-3-(4-methylpiperazin-1-ylmethyl)-2-methyl-1H-indole | 278 |
| D170 | 3-(4-Methylpiperazin-1-ylmethyl)-2-phenyl-1H-indole | 306 |
| D171 | 5-Fluoro-3-(4-methylpiperazin-1-ylmethyl)-2-phenyl-1H-indole | 324 |
| D172 | 5-Chloro-3-(4-methylpiperazin-1-ylmethyl)-2-phenyl-1H-indole | 340 |
| D173 | 3-[1,4]Diazepan-1-ylmethyl-1H-indole | |

Description 174

(R,S) α-(1H-indol-3-yl)-α-(4-methylpiperazin-1-yl)acetonitrile

To indole-3-carboxaldehyde (2 g, 0.0137 moles), sodium bisulfite (1.5 g, 0.015 moles) dissolved in 20 mL water was added and stirred for 1 hr. N-methylpiperazine (1.015 g, 0.015 moles) and sodium cyanide (0.54 g, 0.014 moles) was added at room temperature and the reaction mixture was stirred well for next 12 hrs. After the completion of reaction (TLC), the product was isolated by filtration. The filtrate was extracted with ethyl acetate (2×25 mL); The combined organic extracts were washed with water, followed by brine, dried over anhydrous sodium sulfate. The organic layer was evaporated under vacuum. The residue obtained was further purified by flash chromatography (silica gel, EtOAc/Hexane, 1/1) to afford a solid material, which was identified by IR, NMR and mass spectral analyses as the title compound.

Description 175-178 (D175-D178)

Using essentially the same procedure described in description 174 hereinabove and employing appropriately substituted indole along with either of substituted/unsubstituted piperazine or N,N,N'-trimethyl ethylene-1,2-diamine, compounds given in the list 5 were prepared. The structure of compounds were confirmed latter by IR, NMR and mass spectral analyses.

List-5

| | Description | Mass Ion (M + H)+ |
|---|---|---|
| D174 | (R,S) α-(1H-indol-3-yl)-α-(4-methylpiperazin-1-yl)acetonitrile | 255 |
| D175 | (R,S) α-(5-Bromo-1H-indol-3-yl)-α-(4-methylpiperazin-1-yl)acetonitrile | 333 |
| D176 | (R,S) α-(5-Chloro-1H-indol-3-yl)-α-(4-methylpiperazin-1-yl)acetonitrile | 289 |
| D177 | (R,S) α-(5-Methoxy-1H-indol-3-yl)-α-(4-methylpiperazin-1-yl)acetonitrile | 285 |
| D178 | (R,S) α-(5-Nitro-1H-indol-3-yl)-α-(4-methylpiperazin-1-yl)acetonitrile | 300 |

Description 179-183 (D179-D183)

In order to prepare various derivatives of aryl sulfonylindoles, compounds from D106 to D110 which are essentially tosyl derivatives of differently substituted indol-3-ylmethyl-enechloride are first deprotected using the known procedures in the art. 1-(4-Methylbenzenesulfonyl)-3-chloromethyl-1H-indole (3.19 g, 0.01 moles) was refluxed in 10% NaOH in ethanol for 5-15 hours. After the completion of reaction (TLC, 3-5 hours), water was added and the residue was extracted with ethyl acetate (2×25 mL). The combined organic extracts were washed with water, followed by brine, dried over anhydrous sodium sulfate. The organic layer was evaporated under vacuum. The residue, if needed was purified by flash chromatography (silica gel, EtOAc/Hexane, 2/8) to afford the title compound, which was identified by IR, NMR and mass spectral analyses.

| List-6 | | |
|---|---|---|
| | Description | Mass Ion (M + H)+ |
| D179 | 3-Chloromethyl-1H-indole | 166 |
| D180 | 5-Bromo-3-chloromethyl-1H-indole | 244 |
| D181 | 5-Chloro-3-chloromethyl-1H-indole | 200 |
| D182 | 5-Methoxy-3-chloromethyl-1H-indole | 196 |
| D183 | 5-Nitro-3-chloromethyl-1H-indole | 211 |

Description 184

3-(4-(Benzyloxycarbonyl)piperazin-1-ylmethyl)-1H-indole

Piperazinyl nitrogen in compound (D156) was selectively protected using BOC, according to the procedures known to the art. List -7

| Mass Ion | | Description (M + H)+ |
|---|---|---|
| D 184 | 3-(4-(Benzyloxycarbonyl)piperazin-1-ylmethyl)-1H-indole | 350 |

Description 185 (D185)

(1H-Indol-3-yl)-(4-methylpiperazin-1-yl)methanone

1H-Indole-3-carboxylic acid (1.61 g, 0.01 moles) was stirred with oxalyl chloride (0.99 g, 0.011 moles) in 20 mL dichloromethane at 0 to 25° C. for 3-4 hours. After completion of the reaction (TLC), volatile substances were distilled off under the reduced pressure. The residue was taken in 20 mL dichloroethane and to this stirred solution, was added N-methylpiperazine (1.1 g, 0.011 moles). The reaction mixture was further stirred for next 3-5 hours, till the reaction completes (TLC). Reaction mixture was diluted with dichloromethane 20 mL), washed with water, brine and saturated solution of sodium bicarbonate. The organic layer was dried over sodium sulfate and the organic solvents were evaporated under vacuo. The product was purified using column chromatography on silica gel G stationary phase and suitable combinations of ethyl acetate and methanol in increasing gradient, as the mobile phase.

Description 186-187 (D186-D187)

Using essentially the same procedure described in description 185 hereinabove and employing appropriately substituted indole-3-carboxylic acid with substituted alkyl piperazine or N,N,N'-trimethyl ethylene-1,2-diamine, compounds given in the list 8 were prepared. The structures of compounds, thus obtained, were confirmed by IR, NMR and mass spectral analyses.

List—8

| | Description | Mass Ion (M + H)+ |
|---|---|---|
| D185 | (1H-Indol-3-yl)-(4-methylpiperazin-1-yl)methanone | 244 |
| D186 | (5-Nitro-1H-indol-3-yl)-(4-methylpiperazin-1-yl)methanone | 289 |
| D187 | 1H-Indole-3-carboxylic aciDN-(N',N'-dimethylaminoethyl)-N-methylamide | 246 |

Description 188 (D188)

3-(4-Methylpiperazin-1-ylmethyl)-1H-indole (also, D151)

(1H-Indol-3-yl)-(4-methylpiperazin-1-yl)methanone (2.44 g, 0.01 moles) in THF was treated with cooled and stirred suspension of Lithium aluminum hydride (g, 0.011 moles in THF slowly over the period of 2 to 5 hours, the reaction mixture was heated to reflux for 2-4 hours, after the completion of reaction, the reaction mixture was poured on to the ice and the compound was extracted in ethyl acetate. The residue obtained was purified by flash chromatography (silica gel, EtOAc/Hexanes, 2/8) to afford the compound, which was identified by IR, NMR and mass spectral analyses as the title compound.

Description 189-190 (D189-D190)

Using essentially the same procedure described in description 187 the compounds obtained in Description 184-186 were reduced to the corresponding derivatives. The list of compounds, thus obtained, is given below. The structure of compounds, thus obtained, were confirmed by IR, NMR and mass spectral analyses.

| | List-9 | |
|---|---|---|
| | Description | Mass Ion (M + H)+ |
| D188 | 3-(4-Methylpiperazin-1-ylmethyl)-1H-indole | 230 |
| D189 | 3-(4-Methylpiperazin-1-ylmethyl)-5-nitro-1H-indole | 275 |
| D190 | N-(1H-Indol-3-ylmethyl)-N,N',N'-trimethyl-ethylene-1,2-diamine | 232 |

EXAMPLE-1

1-Benzenesulfonyl-3-(4-methylpiperazin-1-ylmethyl)-5-nitro-1H-indole

1-Benzenesulfonyl-3-chloromethyl-5-nitro-1H-indole (3.5 g, 0.01 mole) and triethylamine (1.11 g, 0.011 moles) in dichloromethane (25 mL) was stirred at 25° C. The reaction mixture was cooled and N-Methylpiperazine (1.1 g, 0.011 moles) was added slowly to this well stirred reaction mixture. The reaction was stirred for 2-4 hours at 25° C. and after the completion of reaction (TLC), mixture was diluted further with 25 mL of dichloromethane and the organic reaction mixture was washed with water and brine. The dichloromethane extract was dried over sodium sulfate and the volatile substances were removed under reduced pressure to obtain the crude intermediate. The residue obtained was purified by flash chromatography (silica gel, EtOAc/Hexanes, 2/8) to afford the compound, which was identified by IR, NMR and mass spectral analyses as the title compound.

The above example can also be prepared according to the procedure given for example—40, and followed by reduction as given in example—53. Melting range (°C.): 107-115; IR spectra (cm$^{-1}$): 1120, 1176, 1378, 1447; Mass (m/z): 414 (M+H)$^+$; $^1$H-NMR (δ ppm) : 2.26 (3H, s), 2.28 (8H, bs), 3.64 (2H, s), 7.44-7.61 (4H, m), 7.88-7.92 (2H, m), 8.04-8.08 (1H, m), 8.18-8.24 (1H, dd, J=2.2 Hz, 9.2 Hz), 8.65-8.66 (1H, d, J=2.2 Hz).

EXAMPLE-2

1-(4-Methylbenzenesulfonyl)-3-(4-methylpiperazin-1-ylmethyl)-5-nitro-1H-indole

Using essentially the same procedure described in example 1, the above derivative was prepared. Melting range (°C.): 134-139; IR spectra (cm$^{-1}$): 1115, 1174, 1375, 1445; Mass (m/z): 428 (M+H)$^+$; $^1$H-NMR (δ ppm): 2.26 (3H, s), 2.30 (3H, s), 2.37 (8H, bs), 3.64 (2H, s), 7.26-7.29 (2H, d), 7.60 (1H, s), 7.76-7.80 (2H, d, J=8.0), 8.02-8.07 (1H, d, J=7.2 Hz), 8.17-8.23 (1H, dd, J=2.2 Hz, 9.1 Hz), 8.63-8.34 (1H, d, J=2.4).

EXAMPLE-3

1-(4-Bromobenzenesulfonyl)-3-(4-methylpiperazin-1-ylmethyl)-5-nitro-1H-indole

Using essentially the same procedure described in example 1, the above derivative was prepared. IR spectra (cm$^{-1}$): 1176, 1287, 1329, 1370, 1507; Mass (m/z): 461(M+H)$^+$, 463 (M+H)$^+$

EXAMPLE-4

1-(4-Fluorobenzenesulfonyl)-3-(4-methylpiperazin-1-ylmethyl)-5-nitro-1H-indole

Using essentially the same procedure described in example 1, the above derivative was prepared. IR spectra (cm$^{-1}$): 1261, 1334, 1372, 1515; Mass (m/z): 433 (M+H)$^+$

EXAMPLE-5

1-(4-Methoxybenzenesulfonyl)-3-(4-methylpiperazin-1-ylmethyl)-5-nitro-1H-indole hydrochloride salt To a 4.45 g of 1-(4-Methoxybenzenesulfonyl)-3-(4-methylpiperazin-1-ylmethyl)-5-nitro-1H-indole (example-124), was added the saturated solution of hydrochloric acid in isopropyl alcohol and stirred at room temperature till crystalline compound separates out. The compound was isolated by filtration, washed with n-hexane, ethylacetate and dried under vacuum. IR spectra (cm$^{-1}$): 1159, 1263, 1337, 1372; Mass (m/z): 445 M+H)$^+$

EXAMPLE-6

1-(4-isopropylbenzenesulfonyl)-3-(4-methylpiperazin-1-ylmethyl)-5-nitro-1H-indole Using essentially the same procedure described in example 1, the above derivative was prepared. IR spectra (cm$^{-1}$): 1121, 1181, 1341, 1376, 1520; Mass (m/z): 457 (M+H)$^+$; $^1$H-NMR (δ ppm): 1.18-1.22 (6H, d, J=7 Hz), 2.28 (3H, s), 2.46 (8H, bs), 2.88-2.92 (1H, h, J=7 Hz) 3.64-3.65 (2H, d, J=0.8 Hz), 7.26-8.66 (8H, m).

EXAMPLE-7

1-(2-Bromobenzenesulfonyl)-3-(4-methylpiperazin-1-ylmethyl)-5-nitro-1H-indole

Using essentially the same procedure described in example 1, the above derivative was prepared. Mass (m/z): 461(M+H)$^+$, 463 (M+H)$^+$

EXAMPLE-8

1-(2-Bromobenzenesulfonyl)-3-(4-methylpiperazin-1-ylmethyl)-5-nitro-1H-indole hydrochloride salt Using essentially the same procedure described in example 5, hydrochloride salt of example 7 was prepared. Melting Range (°C.): 228-224; IR spectra (cm$^{-1}$): 1121, 1175, 1286, 1330; 1370, 1508; Mass (m/z): 461(M+H)$^+$, 463 (M+3)$^+$; $^1$H-NMR (δ ppm): 2.33 (3H, s), 2.53 (8H, bs), 3.70 (2H, s), 7.26-7.75 (4H, m), 7.80 (1H, s), 8.10-8.16 (1H, dd, J=2.2 Hz, 9.1 Hz), 8.28-8.32 (1H, dd, J=1.8 Hz, 7.8 Hz), 8.68-8.70 (1H, d, J=2.6 Hz).

EXAMPLE-9

1-(2-Bromo-4-methoxybenzenesulfonyl)-3-(4-methylpiperazin-1-ylmethyl)-5-nitro-1H-indole Using essentially the same procedure described in example 1, the above derivative was prepared. Melting range (°C.): 136-138; IR spectra (cm$^-$): 1127, 1173, 1346, 1370, 1588; Mass (m/z): 523 (M+H)$^+$, 525 (M+H)$^+$; $^1$H-NMR (δ ppm): 2.29 (3H, s), 2.47 (8H, bs), 3.68-3.70 (2H, d, J=3 Hz), 3.85 (3H, s), 7.02-8.69 (7H, m).

EXAMPLE-10

4,5,6-Trichloro-1-benzenesulfonyl-3-(4-methylpiperazin-1-ylmethyl)-1H-indole

Using essentially the same procedure described in example 1, the above derivative was prepared. IR spectra (cm$^{-1}$): 1124, 1172, 1373; Mass (m/z): 472 (M+H)$^+$; $^1$H-NMR (δ ppm): 2.31 (3H, s), 2.49 (8H, bs), 3.61 (2H, s), 7.47-7.62 (4H, m), 7.77-7.84 (3H, m).

EXAMPLE-11

4,5,6-Trichloro-1-(4-methylbenzenesulfonyl)-3-(4-methylpiperazin-1-ylmethyl)-1H-indole Using essentially the same procedure described in example 1, the above derivative was prepared. Mass (m/z): 487 (M+H)$^+$

EXAMPLE-12

1-(4-Bromobenzenesulfonyl)-4,5,6-trichloro-3-(4-methylpiperazin-1-ylmethyl)-1H-indole Using essentially the same procedure described in example 1, the above derivative was prepared. Mass (m/z): 551 (M+H)$^+$, 553 (M+H)$^+$

EXAMPLE-13

4,5,6-Trichloro-1-(4-isopropylbenzenesulfonyl)-3-(4-methyl piperazin-1-ylmethyl)-1H-indole Using essentially the same procedure described in example 1, the above derivative was prepared. Mass (m/z): 515 (M+H)$^+$

EXAMPLE-14

1-(2-Bromobenzenesulfonyl)-4,5,6-trichloro-3-(4-methyl piperazin-1-ylmethyl)-1H-indole Using essentially the same procedure described in example 1, the above derivative was prepared. IR spectra (cm$^{-1}$): 1140, 1174, 1160, 1373, 1397; Mass (m/z): 551 (M+H)$^+$, 552 (M+H)$^+$; $^1$H-NMR (δ ppm): 2.30 (3H, s), 2.48 (8H, bs), 3.61 (2H, s), 7.40-7.56 (2H, m), 7.68-7.73 (1H, dd), 7.86 (1H, s), 7.92 (1H, s), 8.26-8.31 (1H, dd).

EXAMPLE-15

1-(2-Bromo-4-methoxybenzenesulfonyl)-4,5,6-trichloro-3-(4-methylpiperazin-1-ylmethyl)-1H-indole Using essentially the same procedure described in example 1, the above derivative was prepared. Mass (m/z): 546 (M+H)$^+$, 548 (M+H)$^+$

EXAMPLE-16

1-Benzenesulfonyl-5-methoxy-3-(4-methylpiperazin-1-ylmethyl)-1H-indole 5-methoxy-3-(4-methylpiperazin-1-ylmethyl)-1H-indole (2.59 g, 0.01 moles) in DMF (30 mL) was added slowly to a suspension of sodium hydride (0.26 g, 0.011 moles) in DMF (10 mL) maintaining the temperature below 10° C. The mixture was stirred for 1 hr at 25° C. and benzene sulfonyl chloride (1.76 g, 0.01 moles) was added at 10° C. drop-wise to the reaction mixture. The reaction mixture was further stirred for 1 hr at 25° C. After the completion of reaction (TLC), the reaction mixture was poured onto a ice-water mixture and extracted with ethyl acetate (20 mL×2). The combined organic extracts were washed with water and brine and dried over sodium sulfate. Volatile impurities were distilled off under reduced pressure to obtain the crude residue. The residue obtained was purified by flash chromatography (silica gel, EtOAc/TEA, 9.9/0.1) to afford the compound, which was identified by IR, NMR and mass spectral analyses as the title compound. Melting range (°C.): 120-123; IR spectra (cm$^{-1}$): 1145, 1162, 1366, 1344; Mass (m/z): 400 (M+H)$^+$; $^1$H-NMR (δ ppm): 2.25 (3H, s), 2.41 (8H, bs), 3.53 (2H, s), 3.80 (3H, s), 6.85-6.90 (1H, dd, J=2.6 Hz, 9 Hz), 7.07-7.08 (1H, d, J=2.2 Hz), 7.36-7.50 (4H, m), 7.79-7.85 (2H, m).

EXAMPLE-17

1-(4-Methylbenzenesulfonyl)-5-methoxy-3-(4-methyl piperazin-1-ylmethyl)-1H-indole Using essentially the same procedure described in example 16, the above derivative was prepared. Melting range (°C.): 111-117; IR spectra (cm$^{-1}$): 1146, 1172, 1369, 1450; Mass (m/z): 414 (M+H)$^+$; $^1$H-NMR (δ ppm): 2.27 (3H, s), 2.22 (3H, S)2.44 (8H, bs), 3.60-3.60 (2H, d, J=0.6 (Gem coupling)), 3.78 (3H, s), 6.84-6.88 (2H, m), 7.21-7.46 (2H, m), 7.46 (1H, s), 7.65-7.69 (1H, m), 7.78-7.98 (2H, m)

EXAMPLE-18

1-(4-Bromobenzenesulfonyl)-5-methoxy-3-(4-methyl piperazin-1-ylmethyl)-1H-indole Using essentially the same procedure described in example 16, the above derivative was prepared. IR spectra (cm$^{-1}$): 1147, 1162, 1365, 1451; Mass (m/z): 479, 481 (M+H)$^+$; $^1$H-NMR (δ ppm): 2.28 (3H, s), 2.44 (8H, bs), 3.55-3.56 (2H, d, J=1.0 Hz (Gem coupling)), 3.82 (3H, s), 6.89-6.95 (1H, dd, J=2.8 Hz, 9.0 Hz), 7.13-7.15 (1H, d, J=2.6 Hz), 7.37 (1H, s), 7.51-7.70 (4H, m), 7.81-7.85 (1H, d, J=9.1 Hz).

EXAMPLE-19

1-(4-Isopropylbenzenesulfonyl)-5-methoxy-3-(4-methyl piperazin-1-ylmethyl)-1H-indole Using essentially the same procedure described in example 16, the above derivative was prepared. Melting range (°C.): 115-120; IR spectra (cm$^{-1}$): 1146, 1174, 1370, 1387, 1476; Mass (m/z): 442 (M+H)$^+$; $^1$H-NMR (δ ppm): 1.18-1.22 (6H, d, J=6.6 Hz), 2.29 (3H, s), 2.45 (8H, bs), 2.82-2.92 (1H, h), 3.58 (2H, s), 3.84 (3H, s), 6.91-6.97 (1H, dd, J=2.6 Hz, 9.0 Hz), 7.15-7.16 (1H, d, J=2.4 Hz), 7.24-7.28 (2H, m), 7.44 (1H, s), 7.74-7.78 (2H, m), 7.86-7.91 (1H, d, J=8.8 Hz).

EXAMPLE-20

1-(2-Bromobenzenesulfonyl)-5-methoxy-3-(4-methylpiperazin-1-ylmethyl)-1H-indole

Using essentially the same procedure described in example 16, the above derivative was prepared. Melting range (°C.): 110-116; IR spectra (cm$^{-1}$) 1147, 1178, 1371, 1386, 1449; Mass (m/z): 479, 481 (M+H)$^+$; $^1$H-NMR (δ ppm): 2.28 (3H, s), 2.45 (8H, bs), 3.62-3.625 (2H, d, J=0.8 Hz), 3.82 (3H, s), 6.81-6.87 (1H, dd, J=2.6 Hz, 8.4 Hz), 7.19-7.20 (1H, d, J=2.6 Hz), 7.34-7.68 (6H, m), 8.01-8.06 (1H, dd, J=1.8 Hz, 7.8 Hz).

EXAMPLE-21

1-(2-Bromo-4-methoxybenzenesulfonyl)-5-methoxy?-3-(4-methylpiperazin-1-ylmethyl)-1H-indole Using essentially the same procedure described in example 16, the above derivative was prepared. Mass (m/z): 510, 512 (M+H)$^+$.

EXAMPLE-22

1-(2-Bromo-4-methoxybenzenesulfonyl)-5-methoxy-3-(4-methylpiperazin-1-ylmethyl)-1H-indole hydrochloride salt Using essentially the same procedure described in example 5, hydrochloride salt of example-21 was prepared. IR spectra (cm$^{-1}$): 1147, 1174, 1368, 1471; Mass (m/z): 510, 512 (M+H)$^+$.

EXAMPLE-23

1-(4-methoxybenzenesulfonyl)-5-methoxy-3-(4-methylpiperazin-1-ylmethyl)-1H-indole Using essentially the same procedure described in example 16, the above derivative was prepared. Melting range (°C.): 108-110; IR spectra (cm$^{-1}$): 1120, 1165, 1368, 1454; Mass (m/z): 330 (M+H)$^+$; $^1$H-NMR (δ ppm): 2.27 (3H, s), 2.44 (8H, bs), 3.55-3.56 (2H, d, J=0.6 Hz), 3.78 (3H, s), 3.82 (3H, s), 6.83-6.94 (3H, m), 7.12-7.13 (1H, d, J=2.4 Hz), 7.40 (1H, s), 7.74-7.87 (3H, m).

EXAMPLE-24

1-(4-Fluorobenzenesulfonyl)-5-methoxy-3-(4-methylpiperazin-1-ylmethyl)-1H-indole Using essentially the same procedure described in example 16, the above derivative was prepared. Melting range (°C.): 96-98; IR spectra (cm$^{-1}$): 1177, 1163, 1366, 1448; Mass (m/z): 418 (M+H)$^+$; $^1$H-NMR (δ ppm): 2.22 (3H, s), 2.41 (8H, bs), 3.54 (2H, s), 3.81 (3H, s), 6.88-7.13 (4H, m), 7.37(1H, s), 7.80-7.87 (3H, m).

EXAMPLE-25

5-Bromo-1-(4-fluorobenzenesulfonyl)-3-(4-methylpiperazin-1-ylmethyl)-1H-indole

Using essentially the same procedure described in example 1, the above derivative was prepared. IR spectra (cm$^{-1}$): 1148, 1182, 1352, 1377; Mass (m/z): 466 (M+H)$^+$, 468 (M+H)$^+$.

EXAMPLE-26

5-Bromo-1-4-fluorobenzenesulfonyl)-3-(4-methylpiperazin-1-ylmethyl)-1H-indole hydrochloride salt Using essentially the same procedure described in example 5, hydrochloride salt of example 25 was prepared. IR spectra (cm$^{-1}$): 1181, 1381, 1297, 1181; Mass (m/z): 466 (M+H)$^+$, 468 (M+H)$^+$.

EXAMPLE-27

5-Bromo-1-(4-fluorobenzenesulfonyl)-3-(4-methylpiperazin-1-ylmethyl)-1H-indole maleate salt To the saturated solution of 5-Bromo-1-(4-fluorobenzenesulfonyl)-3-(4-methylpiperazin-1-ylmethyl)-1H-indole (2.3 g) in diethyl ether, the saturated solution of maleic acid in diethyl ether was added slowly under cooling and stirring. The mass was stirred till solid separates out. The crystalline solid was isolated by filtration, washed with hexane, ethyl acetate and dried quickly under vacuum over phosphorous pentoxide. IR spectra (cm$^{-1}$): 1157, 1182, 1384, 1572, 1622, 1692; Mass (m/z): 466 (M+H)$^+$, 468 (M+H)$^+$.

EXAMPLE-28

5-Bromo-1-(4-fluorobenzenesulfonyl)-3-(4-methylpiperazin-1-ylmethyl)-1H-indole citrate salt To the saturated solution of 5-Bromo-1-(4-fluorobenzenesulfonyl)-3-(4-methylpiperazin-1-ylmethyl)-1H-indole (2.3 g) in diethyl ether, the saturated solution of citric acid in diethyl ether was added slowly under cooling and stirring. The mass was stirred till solid separates out. The crystalline solid was isolated by filtration, washed with hexane, ethyl acetate and dried quickly under vacuum over phosphorous pentoxide. IR spectra (cm$^{-1}$): 1159, 1182, 1376, 1590, 1723; Mass (m/z): 466 (M+H)$^+$, 468 (M+H)$^+$.

EXAMPLE-29

5-Bromo-1-(4-methoxybenzenesulfonyl)-3-(4-methylpiperazin-1-ylmethyl)-1H-indole

Using essentially the same procedure described in example 1, the above derivative was prepared. IR spectra (cm$^-$): 1122, 1180, 1373, 1438, 1456; Mass (m/z): 478,480 (M+H)$^+$

EXAMPLE-30

5-Bromo-1-(benzenesulfonyl)-3-(4-methylpiperazin-1-ylmethyl)-1H-indole

Using essentially the same procedure described in example 1, the above derivative was prepared. Melting range (°C.): 133-135; IR spectra (cm$^{-1}$) 1123, 1176, 1366, 1446; Mass (m/z): 449 (M+H)$^+$, 451 (M+H)$^+$; $^1$H-NMR (δ ppm): 2.41 (3H, s), 2.59 (8H, bs), 3.58 (2H, s), 7.38-7.60 (5H, m), 7.80-7.87 (4H, m).

EXAMPLE-31

5-Bromo-1-(4-methylbenzenesulfonyl)-3-(4-methylpiperazin-1-ylmethyl)-1H-indole

Using essentially the same procedure described in example 1, the above derivative was prepared. IR spectra (cm$^{-1}$): 1123, 1176, 1338, 1386; Mass (m/z): 463 (M+H)$^+$, 465 (M+H)$^+$; $^1$H-NMR (δ ppm): 2.29 (3H, s), 2.35 (3H, s), 2.44 (8H, bs), 3.54 (2H, s), 7.20-7.44 (4H, m), 7.70-7.85 (4H, m).

EXAMPLE-32

5-Bromo-1-(4-bromobenzenesulfonyl)-3-(4-methylpiperazin-1-ylmethyl)-1H-indole

Using essentially the same procedure described in example 1, the above derivative was prepared. IR spectra (cm$^{-1}$): 1120, 1250, 1373, 1454; Mass (m/z): 528, 530 (M+H)$^+$.

EXAMPLE-33

5-Bromo-1-(4-isopropylbenzenesulfonyl)-3-(4-methylpiperazin-1-ylmethyl)-1H-indole Using essentially the same procedure described in example 1, the above derivative was prepared. Melting range (°C): 157-159; IR spectra (cm$^-$): 1121, 1179, 1371, 1438, 1456; Mass (m/z): 490, 492 (M+H)$^+$, 390 (M-pip)$^+$; $^1$H-NMR (δ ppm): 1.17-1.21 (6H, d, J=6.8 Hz), 2.28 (3H, s), 2.44 (8H, bs), 2.82-2.92 (1H, h), 3.54-3.55 (2H, d, J=0.8 Hz), 7.25-7.45 (4H, m), 7.73-7.87 (4H, m).

EXAMPLE-34

5-Bromo-1-(2-bromobenzenesulfonyl)-3-4-methylpiperazin-1-ylmethyl)-1H-indole

Using essentially the same procedure described in example 1, the above derivative was prepared. IR spectra (cm$^{-1}$):1128, 1179, 1373, 1446; Mass (m/z): 528, 530 (M+H)$^+$.

EXAMPLE-35

5-Bromo-1-(2-bromobenzenesulfonyl)-3-(4-methylpiperazin-1-ylmethyl)-1H-indole hydrochloride salt Using essentially the same procedure described in example 5, hydrochloride salt of example 34 was prepared. Melting range (°C.): 245-250; IR spectra (cm$^{-1}$): 1128, 1179, 1373, 1446; Mass (m/z): 528, 530 (M+H)$^+$; $^1$H-NMR (δ ppm): 2.94 (3H, s), 2.36-2.52 (8H, bs), 4.44 (2H, s), 7.43-8.44 (8H, m).

EXAMPLE-36

5-Bromo-1-(2-bromo-4-methoxybenzenesulfonyl)-3-(4-methylpiperazin-1-ylmethyl)-1H-indole Using essentially the same procedure described in example 1, the above derivative was prepared. IR spectra (cm$^{-1}$): 1178, 1373, 1446; Mass (m/z): 558, 560 (M+H)$^+$.

EXAMPLE-37

4-Bromo-1-(4-fluorobenzenesulfonyl)-3-(4-methylpiperazin-1-ylmethyl)-1H-indole

Using essentially the same procedure described in example 1, the above derivative was prepared. IR spectra (cm$^{-1}$): 1165, 1228, 1369, 1670; Mass (m/z): 466, 468 (M+H)$^+$.

EXAMPLE-38

4-Bromo-1-(4-methoxybenzenesulfonyl)-3-(4-methylpiperazin-1-ylmethyl)-1H-indole

Using essentially the same procedure described in example 1, the above derivative was prepared. IR spectra (cm$^{-1}$):1166, 1263, 1372, 1673; Mass (m/z): 478, 480 (M+H)$^+$.

EXAMPLE-39

4-Bromo-1-(4-isopropylbenzenesulfonyl)-3-(4-methylpiperazin-1-ylmethyl)-1H-indole Using essentially the same procedure described in example 1, the above derivative was prepared. IR spectra (cm$^{-1}$): 1160, 1250, 1378, 1666; Mass (m/z): 490, 492 (M+H)$^+$.

EXAMPLE-40

(1-Benzenesulfonyl-1H-indol-3-yl)-(4-methylpiperazin-1-yl)methanone

1-Benzenesulfonylindole-3-carboxylic acid (3.01 g, 0.01 moles) was stirred with oxalyl chloride (1.309 g, 0.011 moles) in 20 mL dichloromethane at 0 to 25° C. for 3-4 hours. After completion of the reaction (T.L.C.), volatile substances were distilled off under the reduced pressure. The residue was taken in 20 mL dichloroethane and to this stirred solution, was added N-methylpiperazine (1.1 g, 0.011 moles). The reaction mixture was further stirred for next 3-5 hours till the reaction completes (TLC). Reaction mixture was diluted with dichloromethane 20 mL), washed with water, brine and saturated solution of sodium bicarbonate. The organic layer was dried over sodium sulfate and the organic solvents were evaporated under vacuo. The product was purified using column chromatography on silica gel G stationary phase and suitable combinations of ethyl acetate and methanol in increasing gradient as the mobile phase. IR spectra (cm$^{-1}$) 3140, 1621, 1552, 1451; Mass (m/z): 484 (M+H)$^+$

EXAMPLE-41

[1-(4-Methylbenzenesulfonyl)-1H-indol-3-yl]-(4-methylpiperazin-1-yl)methanone

Using essentially the same procedure described in the example 40, above analog was prepared. IR spectra (cm-1): 3131, 1633, 1553, 1446; Mass (m/z): 498 (M+H)$^+$; $^1$H-NMR (δ ppm): 2.32 (3H, s), 2.35 (3H, s), 2.50 (4H, s), 3.7 (4H, s), 7.223-7.99 (9H, m).

EXAMPLE-42

[1-(4-isopropylbenzenesulfonyl)-1H-indol-3-yl]-(4-methylpiperazin-1-yl)methanone Using essentially the same procedure described in the example 40, above analog was prepared. IR spectra (cm$^{-1}$): 3066, 1630, 1553, 1446; Mass (m/z): 426 (M+H)$^+$; $^1$H-NMR (δ ppm): 1.19-1.23 (6H, d), 2.34 (3H, s), 2.46 (4H, s), 2.8-2.95 (1H, m), 3.71 (4H, s), 7.28-8.05 (9H, m).

EXAMPLE-43

[1-(2-Bromobenzenesulfonyl)-1H-indol-3-yl]-(4-methylpiperazin-1-yl)methanone

Using essentially the same procedure described in the example 40, above analog was prepared. IR spectra (cm$^{-1}$): 3142, 1623, 1550, 1450; Mass (m/z): 462, 464(M+H)$^+$; $^1$H-NMR (δ ppm): 2.34 (3H, s), 2.46 (4H, s), 3.74 (4H, s), 7.25-8.27 (9H, m).

EXAMPLE-44

[1-(2-Bromo-4-methoxybenzenesulfonyl)-1H-indol-3-yl]-(4-methylpiperazin-1-yl)methanone Using essentially the same procedure described in the example 40, above analog was prepared. Mass (m/z): 492 (M+H)$^+$, 494 (M+H)$^+$; $^1$H-NMR (δ ppm): 2.33 (3H, s), 2.47 (4H, s), 3.73 (4H, s), 3.84 (3H, s), 7.01-8.30 (8H, m).

EXAMPLE-45

(1-Benzenesulfonyl-5-nitro-1H-indol-3-yl)-(4-methylpiperazin-1-yl)methanone

Using essentially the same procedure described in the example 40, above analog was prepared. Melting range (°C.): 158-160; IR spectra (cm$^{-1}$): 3133, 1620, 1556, 1447; Mass (m/z): 429 (M+H)$^+$; $^1$H-NMR (δ ppm): 2.37 (3H, s), 2.50 (4H, bs), 3.74 (4H, bs), 7.52-8.63 (8H, m).

EXAMPLE-46

[1-(4-Methylbenzenesulfonyl)-5-nitro-1H-indol-3-yl]-(4-methylpiperazin-1-yl)methanone Using essentially the same procedure described in the example 40, above analog was prepared. Melting range (°C.): 188-190; IR spectra (cm$^{-1}$): 3116, 1626, 1514, 1442; Mass (m/z): 443 (M+H)$^+$; $^1$H-NMR (δ ppm): 2.35 (3H, s), 2.39 (3H, s), 2.48 (4H, s), 3.73 (4H, s), 7.83-8.62 (8H, m).

EXAMPLE-47

[1-(4-Fluorobenzenesulfonyl)-5-nitro-1H-indol-3-yl]-(4-methylpiperazin-1-yl)methanone Using essentially the same procedure described in the example 40, above analog was prepared. Melting range (°C.): 180-184; IR spectra (cm$^{-1}$): 3096, 1629, 1556, 1465; Mass (m/z): 447 (M+H)$^+$; $^1$H-NMR (δ ppm): 2.36 (3H, s), 2.49 (4H, bs), 3.74 (4H, bs), 7.22-8.63 (8H, m).

EXAMPLE-48

[1-(4-Bromobenzenesulfonyl)-5-nitro-1H-indol-3-yl]-(4-methylpiperazin-1-yl)methanone Using essentially the same procedure described in the example 40, above analog was prepared. Mass (m/z): 507, 509 (M+H)$^+$; $^1$H-NMR (δ ppm): 2.36 (3H, s), 2.48 (4H, bs), 3.73 (4H, bs), 7.63-8.63 (8H, m).

EXAMPLE-49

[1-(4-Isopropylbenzenesulfonyl)-5-nitro-1H-indol-3-yl]-(4-methylpiperazin-1-yl)methanone Using essentially the same procedure described in the example 40, above analog was prepared. Melting range (°C.): 170-172; IR spectra (cm$^{-1}$): 3125, 1631, 1557, 1441; Mass (m/z): 471 (M+H)$^+$; $^1$H-NMR (δ ppm): 1.19-1.22 (6H, d), 2.41 (3H, s), 2.57 (4H, bs), 2.82-2.92 (1H, h), 3.80 (4H, b), 7.26-8.63 (8H, m).

EXAMPLE-50

[1-(2-Bromobenzenesulfonyl)-5-nitro-1H-indol-3-yl]-(4-methylpiperazin-1-yl)methanone Using essentially the same procedure described in the example 40, above analog was prepared. Melting range (°C.): 148-150; IR spectra (cm$^{-1}$): 3150, 1620, 1549, 1441; Mass (m/z): 507 (M+H)$^+$, 509 (M+H)$^+$; $^1$H-NMR (δ ppm): 2.35 (3H, s), 2.489 (4H, bs), 3.76 (4H, bs), 7.78-8.68 (8H, m).

EXAMPLE-51

[1-(4-Methoxybenzenesulfonyl)-5-nitro-1H-indol-3-yl]-(4-methylpiperazin-1-yl)methanone Using essentially the same procedure described in the example 40, above analog was prepared. Melting range (°C.): 146-148; IR spectra (cm$^{-1}$): 3122, 1625, 1587, 1441; Mass (m/z): 459 (M+H)$^+$; $^1$H-NMR (δ ppm): 2.35 (3H, s), 2.47 (4H, bs), 3.73 (4H, bs), 3.83 (3H, s), 6.91-8.63 (8H, m).

EXAMPLE-52

[1-(2-Bromo-4-methoxybenzenesulfonyl)-5-nitro-1H-indol-3-yl]-(4-methylpiperazin-1-yl)methanone Using essentially the same procedure described in the example 40, above analog was prepared. IR spectra (cm$^{-1}$): 3097, 1629, 1522, 1440; Mass (m/z): 554, 556 (M+NH$_4$)$^+$; $^1$H-NMR (δ ppm): 2.35 (3H, s), 2.48 (4H, bs), 3.74 (4H, b), 3.87 (3H, s), 7.26-8.68 (7H, m).

EXAMPLE-53

1-Benzenesulfonyl-3-(4-methylpiperazin-1-ylmethyl)-1H-indole (1-Benzenesulfonyl-1H-indol-3-yl)-(4-methylpiperazin-1-yl)methanone (0.8 g, 0.002 moles) in THF (10 mL) was treated with cooled and stirred suspension of LAH (0.04 g, 0.001 moles) in THF (10 mL) slowly over the period of 2 to 5 hours, the reaction mixture was heated to reflux for 2-4 hours, after the completion of reaction, the reaction mixture was poured on to the ice and the compound was extracted with ethyl acetate.

The residue obtained was purified by flash chromatography (silica gel, EtOAc/Hexanes, 2/8) to afford the compound, which was identified by IR, NMR and mass spectral analyses as the title compound. Alternatively the above compound may also be prepared as followed in example 1, and example 16, IR spectra (cm$^{-1}$): 1143, 1174, 1367, 1447; Mass (m/z): 370 (M+H)$^+$; $^1$H-NMR (δ ppm): 2.26 (3H, s), 2.43 (8H, bs), 3.59 (2H, s), 7.18-7.98 (10H, m).

EXAMPLE-54

1-(4-Methylbenzenesulfonyl)-3-(4-methylpiperazin-1-ylmethyl)-1H-indole

Using essentially the same procedure as described in example 53, the above derivative was prepared. Melting range (°C.): 109-110; IR spectra (cm$^{-1}$): 1125, 1177, 1358, 1449; Mass (m/z): 384 (M+H)$^+$; $^1$H-NMR (δ ppm): 2.27 (3H, s), 2.33 (3H, s), 2.45 (8H, bs), 3.59 (2H, s), 7.18-7.31 (4H, m), 7.46 (1H, s), 7.65-7.69 (3H, m) 7.73-7.97 (1H, m).

EXAMPLE-55

1-(4-Fluorobenzenesulfonyl)-3-(4-methylpiperazin-1-ylmethyl)-1H-indole

Using essentially the same procedure as described in example 53, the above derivative was prepared. Melting range (°C.) 107-108; IR spectra (cm$^{-1}$): 1126, 1178, 1372, 1450, 1492; Mass (m/z): 388 (M+H)$^+$; $^1$H-NMR (δ ppm): 2.27 (3H, s), 2.44 (8H, bs), 3.60 (2H, s), 7.05-7.36 (5H, m), 7.44 (1H, s), 7.66-7.67 (1H, m), 7.70-7.97 (2H, m).

EXAMPLE-56

1-(4-Bromobenzenesulfonyl)-3-(4-methylpiperazin-1-ylmethyl)-1H-indole

Using essentially the same procedure as described in example 53, the above derivative was prepared. IR spectra (cm$^{-1}$): 1145, 1178, 1372, 1380; Mass (m/z): 448, 450 (M+H)$^+$; $^1$H-NMR (δ ppm): 2.27 (3H, s), 2.43 (8H, bs), 3.58-3.59 (1H, d, J=0.6 Hz), 7.20-7.33 (2H, m), 7.40 (1H, s), 7.51-7.55 (1H, dd), 7.64-7.68 (3H, m), 7.70-7.93 (1H, dd).

EXAMPLE-57

1-(4-Isopropylbenzenesulfonyl)-3-(4-methylpiperazin-1-ylmethyl)-1H-indole

Using essentially the same procedure as described in example 53, the above derivative was prepared. IR spectra (cm$^{-1}$): 1121, 1144, 1190, 1371; Mass (m/z): 411 (M+H)$^+$; $^1$H-NMR (δ ppm): 1.17-1.18 (3H, d) 1.20-1.26 (3H, d), 2.22 (3H, s), 2.46 (8H, bs), 2.82-2.92 (1H, h), 3.61 (2H, s), 7.19-7.36 (4H, m), 7.48 (1H, m), 7.66-7.81 (3H, m), 7.97-8.00 (1H, d).

EXAMPLE-58

1-(2-Bromobenzenesulfonyl)-3-(4-methylpiperazin-1-ylmethyl)-1-H-indole

Using essentially the same procedure as described in example 53, the above derivative was prepared. IR spectra (cm$^{-1}$): 1123, 1179, 1373, 1447; Mass (m/z): 448, 430 (M+H)$^+$; $^1$H-NMR (δ ppm): 2.28 (3H, s), 2.45 (8H, bs), 3.66 (2H, s), 7.18-7.75 (8H, m), 8.10-8.15 (1H, dd, J=2.0 Hz, 7.8 Hz).

EXAMPLE-59

1-(2-Bromobenzenesulfonyl)-3-(4-methylpiperazin-1-ylmethyl)-1H-indole hydrochloride salt Using essentially the same procedure as described in example 5 and using example 58 the above derivative was prepared. Melting range (°C.): 242-244; IR spectra (cm$^{-1}$): 1123, 1179, 1373, 1447; Mass (m/z): 448, 450 (M+H)$^+$; $^1$H-NMR (δ ppm) : 3.02 (3H, s), 3.66 (8H, bs), 4.67 (2H, s), 7.33-7.94 (7H, m), 8.34 (1H, s), 8.43-8.48 (1H, dd, J=2.2Hz, 8.0 Hz).

EXAMPLE-60

1-(2-Bromo-4-methoxybenzenesulfonyl)-3-(4-methylpiperazin-1-ylmethyl)-1H-indole

Using essentially the same procedure as described in example 53, above derivative was prepared. Mass (m/z): 479 (M+H)$^+$, 481 (M+H)$^+$

EXAMPLE-61

1-2-Bromo-4-methoxybenzenesulfonyl)-3-(4-methylpiperazin-1-ylmethyl)-1H-indole Hydrochloride salt Using essentially the same procedure as described in example 5 and using example 60 the above derivative was prepared. Mass (m/z): 479, 481 (M+H)$^+$(base)

EXAMPLE-62

1-(4-methoxybenzenesulfonyl)-3-(4-methylpiperazin-1-ylmethyl)-1 H-indole

Using essentially the same procedure as described in example 53, above derivative was prepared. Melting range (C): 115-117; IR spectra (cm~1): 1125, 1170, 1358, 1451; Mass (m/z): 400 (M+H)$^+$, 300 (M-piperazine)$^+$; $^1$H-NMR (ppm): 2.27 (3H, s), 2.44 (8H, bs), 3.60 (2H, s), 3.78 (3h, s), 6.84-6.88 (2H, m), 7.21-7.31 (2H, m), 7.46 (1H, s), 7.65-7.69 (1H, dd), 7.78-7.83 (2H, m), 7.93-7.97 (1H, d, J=7.6 Hz).

EXAMPLE 63

1-(2-Bromo-4-methoxybenzenesulfonyl)-5-chloro-2-methyl-3-(4-methylpiperazin-1-ylmethyl)-1H-indole Using essentially the same procedure as described in example 16, and D169, above derivative was prepared. Mass (m/z): 526 (M+H)$^+$, 528 (M+H)$^+$

EXAMPLE-64

5-Chloro-1-(4-fluorobenzenesulfonyl)-2-methyl-3-(4-methylpiperazin-1-ylmethyl)-1H-indole Using essentially the same procedure as described in example 16, above derivative was prepared. Mass (m/z): 436 (M+H)$^+$

EXAMPLE-65

1-(4-Bromobenzenesulfonyl)-5-chloro-2-methyl-3-(4-methylpiperazin-1-ylmethyl)-1H-indole Using essentially the same procedure as described in example 16, above derivative was prepared. Mass (m/z): 496 (M+H)$^+$, 498 (M+H)$^+$

EXAMPLE-66

5-Chloro-1-(4-Isopropylbenzenesulfonyl)-2-methyl-3-(4-methylpiperazin-1-ylmethyl)-1H-indole Using essentially the same procedure as described in example 16, above derivative was prepared. Mass (m/z): 460 (M+H)$^+$

EXAMPLE-67

1-Benzenesulfonyl-5-chloro-2-phenyl-3-(4-methylpiperazin-1-ylmethyl)-1H-indole

A solution of 5-Chloro-3-(4-methylpiperazin-1-ylmethyl)-2-phenyl-1H-indole (D172, 2.63 g, 0.01 moles) in THF (25 mL) was cooled to −78° C. To this well-stirred solution, n-butyl lithium (0.7 g, 0.011 moles, 4.4 mL of 2.5 M solution in hexanes) was added slowly maintaining the temperature below −70° C. The reaction mixture was stirred for 30 minutes, and benzenesulfonyl chloride (1.94 g, 0.011 moles) was added slowly maintaining the temperature below −70° C. over 10 minutes. The reaction mixture was stirred for another 1 hour, after which the reaction was allowed to come to 25° C. gradually and stirred for 1 hour. After the completion of reaction (TLC), the reaction mixture was quenched using ice-cold water (100 mL) and extracted with ethyl acetate (20 mL×3). The combined organic extracts were washed with water and brine and dried over sodium sulfate. Volatile impurities were distilled off under reduced pressure to obtain the crude residue. The residue obtained was purified by flash chromatography (silica gel, EtOAc/TEA, 9.9/0.1) to afford the compound, which was identified by IR, NMR and mass spectral analyses as the title compound. Mass (m/z): 480 (M+H)$^+$; $^1$H-NMR (δ ppm): 2.24-2.31 (11H, bs), 3.28 (2H, s), 7.25-8.26 (13H, m).

EXAMPLE-68

5-Chloro-1-(4-methylbenzenesulfonyl)-2-phenyl-3-(4-methylpiperazin-1-ylmethyl)-1H-indole Using essentially the same procedure as described in example 67, above derivative was prepared. IR spectra (cm$^{-1}$): 1124, 1182, 1220, 1380; Mass (m/z): 494 (M+H)$^+$

EXAMPLE-69

1-(Benzenesulfonyl)-5-fluoro-2-phenyl-3-(4-methylpiperazin-1-ylmethyl)-1H-indole Using essentially the same procedure as described in example 67, above derivative was prepared. IR spectra (cm$^{-1}$): 1123, 1183, 1221, 1378, 1461; Mass (m/z) 464 (M+H)$^+$; $^1$H-NMR (δ ppm): 2.23-2.27 (11H, bs), 3.27 (2H, s), 7.24-8.25 (13H, m).

EXAMPLE-70

5-Fluoro-1-(4-methylbenzenesulfonyl)-2-phenyl-3-(4-methylpiperazin-1-ylmethyl)-1H-indole Using essentially the same procedure as described in example 67, above derivative was prepared. IR spectra (cm$^{-1}$): 1182, 1274, 1320, 1350, 1459; Mass (m/z) 478 (M+H)$^+$

EXAMPLE-71

1-(4-Bromobenzenesulfonyl)-5-chloro-2-phenyl-3-(4-methylpiperazin-1-ylmethyl)-1H-indole Using essentially the same procedure as described in example 67, above derivative was prepared. IR spectra (cm$^{-1}$): 1160, 1272, 1320, 1355; Mass (m/z): 559, 561 (M+H)$^+$

EXAMPLE-72

1-(2-Bromobenzenesulfonyl)-5-cyano-3-(4-methylpiperazin-1-ylmethyl)-1H-indole hydrochloride salt Using essentially the same procedure as described in example 5, the salt of base was prepared. IR spectra (cm$^{-1}$): 1136, 1279, 1377, 1449; Mass (m/z): 473 (M+H)$^+$, 475 (M+H)$^+$.

EXAMPLE-73

5-Cyano-1-(4-methoxybenzenesulfonyl)-3-(4-methylpiperazin-1-ylmethyl)-1H-indole

Using essentially the same procedure as described in example 1, above derivative was prepared. IR spectra (cm$^{-1}$): 1174, 1287, 1371, 1455, 2213; Mass (m/z): 425 (M+H)$^+$.

EXAMPLE-74

5-Cyano-1-(4-fluorobenzenesulfonyl)-3-(4-methylpiperazin-1-ylmethyl)-1H-indole

Using essentially the same procedure as described in example 1, above derivative was prepared. IR spectra (cm$^{-1}$): 1175, 1286, 1370, 1455, 2215; Mass (m/z): 413 (M+H)$^+$

EXAMPLE-75

1-(4-Bromobenzenesulfonyl)-5-cyano-3-(4-methylpiperazin-1-ylmethyl)-1H-indole

Using essentially the same procedure as described in example 1, above derivative was prepared. IR spectra (cm$^{-1}$): 1174, 1284, 1372, 1456, 2217; Mass (m/z): 473, 475 (M+H)$^+$

EXAMPLE-76

5-Cyano-1-(4-Isopropylbenzenesulfonyl)-3-(4-methylpiperazin-1-ylmethyl)-1H-indole Using essentially the same procedure as described in example 1, above derivative was prepared. IR spectra (cm$^{-1}$): 1177, 1299, 1350, 1456, 2227; Mass (m/z): 437 (M+H)$^+$.

EXAMPLE-77

N-(1-(4-Fluorobenzenesulfonyl)-1H-indol-3-yl)methyl-N,N',N'-trimethylethylene-1,2-diamine Using essentially the same procedure as described in example 1, above derivative was prepared. IR spectra (cm$^{-1}$): 1179, 1252, 1373, 1442; Mass (m/z): 390 (M+H)$^+$; $^1$H-NMR (δ ppm): 2.22 (6H, s), 2.46-2.5 (4H, m), 3.61 (2H, s), 2.5-2.55 (4H, q), 3.65 (2H, s), 7.04-7.97 (9H, m).

EXAMPLE-78

N-(1-(4-Fluorobenzenesulfonyl)-1H-indol-3-yl)methyl-N,N',N'-trimethylethylene-1,2-diamine Hydrochloride salt Using essentially the same procedure as described in example 5, above derivative was prepared. IR spectra (cm$^{-1}$): 1180, 1254, 1370, 1450; Mass (m/z): 390 (M+H)$^+$.

EXAMPLE-79

N-(1-(4-Bromobenzenesulfonyl)-5-bromo-1H-indol-3-yl)methyl-N,N', N'-trimethylethylene-1,2-diamine Using essentially the same procedure as described in example 1, above derivative was prepared. IR spectra (cm$^{-1}$): 1175, 1252, 1369, 1448; Mass (m/z): 530 (M+H)$^+$, 532 (M+H)$^+$

EXAMPLE-80

N-(1-(4-Bromobenzenesulfonyl)-5-bromo-1H-indol-3-yl)methyl-N,N',N'-trimethylethylene-1,2-diamine Hydrochloride salt Using essentially the same procedure as described in example 5, above derivative was prepared. IR spectra (cm$^{-1}$): 1176, 1254, 1370, 1450; Mass (m/z): 530 (M+H)$^+$, 532 (M+H)$^+$

EXAMPLE-81

N-(5-Bromo-1-(4-methoxybenzenesulfonyl)-1H-indol-3-yl)methyl-N,N',N'-trimethylethylene-1,2-diamine Using essentially the same procedure as described in example 1, above derivative was prepared. IR spectra (cm$^{-1}$): 1172, 1260, 1375, 1455; Mass (m/z): 482, 484 (M+H)$^+$; $^1$H-NMR (δ ppm): 2.19 (3H, s), 2.22 (6H, s), 2.45-2.49 (4H, q), 3.55 (2H, s), 3.79 (3H, s), 6.84-7.85 (8H, m).

EXAMPLE-82

N-(1-(4-Methoxybenzenesulfonyl)-5-nitro-1H-indol-3-yl)methyl-N,N',N'-trimethylethylene-1,2-diamine Using essentially the same procedure as described in example 1, above derivative was prepared. IR spectra (cm$^{-1}$): 1176, 1262, 1376, 1450; Mass (m/z): 447.3 (M+H)$^+$; $^1$H-NMR (δ ppm): 2.20 (3H, s), 2.264 (6H, s), 3.881 (2H, s), 2.5-2.55 (4H, q), 3.65 (2H, s), 6.80-8.69 (8H, m).

EXAMPLE-83

N-(1-(4-Methoxybenzenesulfonyl)-5-nitro-1H-indol-3-yl)methyl-N,N',N'-trimethylethylene-1,2-diamine Hydrochloride salt Using essentially the same procedure as described in example 5, above derivative was prepared. IR spectra (cm$^{-1}$): 1170, 1260, 1365, 1448; Mass (m/z): 447 (M+H)$^+$

EXAMPLE-84

N-(1-(2-Bromobenzenesulfonyl)-5-bromo-1H-indol-3-yl)methyl-N,N',N'-trimethylethylene-1,2-diamine Using essentially the same procedure as described in example 1, above derivative was prepared. IR spectra (cm$^{-1}$): 1462, 1373, 1172, 1126; Mass (m/z): 528 (M+H)$^+$, 530 (M+H)$^+$.

EXAMPLE-85

1-(2-Bromobenzenesulfonyl)-3-(4-(3-chlorobenzene-1-yl)piperazin-1-ylmethyl)-1H-indole Using essentially the same procedure as described in example 1, above derivative was prepared. Melting range (°C.): 133-140; IR spectra (cm$^{-1}$): 1594, 1369, 1235, 1177; Mass (m/z): 544 (M+H)$^+$, 546 (M+H)$^+$.

EXAMPLE-86

1-(4-Methoxybenzenesulfonyl)-3-(4-(2-methoxybenzene-1-yl)piperazin-1-ylmethyl)-1H-indole Using essentially the same procedure as described in example 1, above derivative was prepared. Melting range (°C.): 148-152; IR spectra (cm$^{-1}$): 1595, 1360, 1264, 1168; Mass (m/z): 492 (M+H)$^+$.

EXAMPLE-87

1-(2-Bromo-4-methoxybenzenesulfonyl)-3-(4-(2-methoxybenzene-1-yl)piperazin-1-ylmethyl)-1H-indole Using essentially the same procedure as described in example 1, above derivative was prepared. IR spectra (cm$^{-1}$): 1587, 1369, 1238, 1175; Mass (m/z): 570, 572 (M+H)$^+$

EXAMPLE-88

1-(4-Isopropylbenzenesulfonyl)-3-(4-(2-methoxybenzene-1-yl)piperazin-1-ylmethyl)-1H-indole Using essentially the same procedure as described in example 1, above derivative was prepared. IR spectra (cm$^{-1}$): 1595, 1374, 1238, 1180; Mass (m/z): 504 (M+H)$^+$; $^1$H-NMR (δ ppm): 1.16-1.20 (6H, d), 2.66-2.70 (4H, bs), 2.80-3.00 (1H, h), 3.07-3.21 (4H, bs), 3.69 (2H, s), 3.85 (3H, s), 6.86-7.97 (13H, m).

EXAMPLE-89

5-Bromo-1-(4-fluorobenzenesulfonyl)3-(4-(2-methoxybenzene-1-yl)piperazin-1-ylmethyl)-1H-indole Using essentially the same procedure as described in example 1, above derivative was prepared. Melting Range (°C.): 179-186; IR spectra (cm$^{-1}$): 1591, 1374, 1238, 1180; Mass (m/z): 558 (M+H)$^+$, 560 (M+H)$^+$.

EXAMPLE-90

5-Bromo-1-(4-methoxybenzenesulfonyl)-3-(4-(2-methoxybenzene-1-yl)piperazin-1-ylmethyl)-1H-indole Using essentially the same procedure as described in example 1, above derivative was prepared. Melting range (°C.): 173-175; IR spectra (cm$^{-1}$): 1591, 1375, 1267, 1167; Mass (m/z): 567, 569 (M+H)$^+$.

EXAMPLE-91

5-Bromo-1-(4-isopropylbenzenesulfonyl)-3-(4-(2-methoxybenzene-1-yl)piperazin-1-ylmethyl)-1-H-indole Using essentially the same procedure as described in example 1, above derivative was prepared. IR spectra (cm$^{-1}$): 1595, 1374, 1240, 1174; Mass (m/z): 582, 584 (M+H)$^+$; $^1$H-NMR (δ ppm): 1.17-1.21 (6H, d), 2.63-2.65 (4H, bs), 2.80-3.00 (1H, h), 3.07-3.10 (4H, bs), 3.63 (2H, s), 3.85 (3H, s), 6.87-7.88 (12H, m).

EXAMPLE-92

1-(4-Fluorobenzenesulfonyl)-5-methoxy-3-(4-(2-methoxybenzene-1-yl)piperazin-1-ylmethyl)-1H-indole Using essentially the same procedure as described in example 1, above derivative was prepared. Mass (m/z): 510 (M+H)$^+$; $^1$H-NMR (δ ppm): 2.65-2.71 (4H, dd), 3.07-3.2 (4H, dd), 3.64 (2H, s), 3.65 (2H, s), 3.83 (3H, s), 3.85 (3H, s), 6.83-7.90 (12H, m)

EXAMPLE-93

1-(4-Fluorobenzenesulfonyl)-5-methoxy-3-(4-(2-methoxybenzene-1-yl)piperazin-1-ylmethyl)-1H-indole Hydrochloride salt Using essentially the same procedure as described in example 5, and using example 92 the above derivative was prepared. IR spectra (cm$^{-1}$): 1590, 1371, 1241, 1181; Mass (m/z): 510 (M+H)$^+$.

EXAMPLE-94

1-(4-Methoxybenzenesulfonyl)-5-methoxy-3-(4-(2-methoxybenzene-1-yl)piperazin-1-ylmethyl)-1H-indole Using essentially the same procedure as described in example 1, above derivative was prepared. Melting Range (°C.): 188-190; IR spectra (cm$^{-1}$): 1594, 1367, 1237, 1165; Mass (m/z): 522 (M+H)$^+$; $^1$H-NMR (δ ppm): 2.64-2.66 (4H, dd), 3.06-3.2 (4H, dd), 3.64 (2H, s), 3.78 (3H, s), 3.82 (3H, s), 3.85 (3H, s), 6.83-7.88 (12H, m).

EXAMPLE-95

1-(4-Isopropylbenzenesulfonyl)-5-methoxy-3-(4-(2-methoxybenzene-1-yl)piperazin-1-ylmethyl)-1H-indole Using essentially the same procedure as described in example 1, above derivative was prepared. Melting Range (°C.): 121-122; IR spectra (cm$^{-1}$): 1594, 1372, 1238, 1174; Mass (m/z): 534 (M+H)$^+$; $^1$H-NMR (δ ppm): 1.16-1.20 (6H, d), 2.60-2.67 (4H, bs), 2.80-3.00 (1H, h), 3.10-3.21 (4H, bs), 3.64 (2H, s), 3.83 (3H, s), 3.85 (3H, s), 3.85 (3H, s), 6.83-7.90 (12H, m).

EXAMPLE-96

1-(4-Fluorobenzenesulfonyl)-3-(4-(pyridin-2-yl)piperazin-1-ylmethyl)-1H-indole

Using essentially the same procedure as described in example 1, above derivative was prepared. IR spectra (cm$^{-1}$): 1593, 1374, 1234, 1179; Mass (m/z): 451 (M+H)$^+$.

EXAMPLE-97

1-(4-Methoxybenzenesulfonyl)-3-(4-(pyridin-2-yl)piperazin-1-ylmethyl)-1H-indole

Using essentially the same procedure as described in example 1, above derivative was prepared. Melting range (°C.): 120-122; IR spectra (cm$^-$): 1025, 1118, 1372, 1596; Mass (m/z): 463 (M+H)$^+$; $^1$H-NMR (δ ppm): 2.52-2.57 (4H, dd), 3.49-3.54 (4H, dd), 3.65-3.65 (2H, d), 3.79 (3H, s), 6.57-8.19 (13H, m).

EXAMPLE-98

1-(4-Isopropylbenzenesulfonyl)-3-(4-(pyridin-2-yl)piperazin-1-ylmethyl)-1H-indole Using essentially the same procedure as described in example 1, above derivative was prepared. IR spectra (cm$^{-1}$): 1595, 1371, 1246, 1174; Mass (m/z): 475 (M+H)$^+$.

EXAMPLE-99

1-(2-Bromobenzenesulfonyl)-3-(4-(pyridin-2-yl)piperazin-1-ylmethyl)-1H-indole

Using essentially the same procedure as described in example 1, above derivative was prepared. IR spectra (cm$^{-1}$): 1595, 1373, 1232, 1178; Mass (m/z): 511, 513 (M+H)$^+$; $^1$H-NMR (δ ppm): 2.53-2.55 (4H, dd), 3.55-3.60 (4H, dd), 6.59-8.20 (12H, m)

EXAMPLE-100

1-(2-Bromo-4-methoxybenzenesulfonyl)-3-(4-(pyridin-2-yl)piperazin-1-ylmethyl)-1H-indole Using essentially the same procedure as described in example 1, above derivative was prepared. IR spectra (cm$^{-1}$): 1590, 1361, 1234, 1175; Mass (m/z): 541 (M+H)$^+$, 543 (M+H)$^+$

EXAMPLE-101

5-Bromo-1-(4-fluorobenzenesulfonyl)-3-(4-(pyridin-2-yl)piperazin-1-ylmethyl)-1H-indole Using essentially the same procedure as described in example 1, above derivative was prepared. Melting Range (°C.): 134-136; IR spectra (cm$^{-1}$): 1593, 1378, 1240, 1179; Mass (m/z): 529, 531 (M+H)$^+$; $^1$H-NMR (δ ppm): 2.53-2.55 (4H, dd), 3.50-3.53 (4H, dd), 3.55 (2H, s), 3.60 (3H, s), 6.59-8.20 (12H, m).

EXAMPLE-102

5-Bromo-1-(4-methoxybenzenesulfonyl)-3-(4-(pyridin-2-yl)piperazin-1-ylmethyl)-1H-indole Using essentially the same procedure as described in example 1, above derivative was prepared. Melting Range (°C.): 134-136; IR spectra (cm$^{-1}$): 1595, 1371, 1262, 1164; Mass (m/z): 541, 543 (M+H)$^+$; $^1$H-NMR (δ ppm): 2.50-2.55 (4H, dd), 3.50-3.55 (4H, dd), 3.60 (2H, s), 3.80 (3H, s), 6.58-8.19 (12H, m).

EXAMPLE-103

5-Bromo-1-(4-isopropylbenzenesulfonyl)-3-(4-(pyridin-2-yl)piperazin-1-ylmethyl)-1H-indole Using essentially the same procedure as described in example 1, above derivative was prepared. Melting Range (°C.): 148-150; IR spectra (cm$^{-1}$): 1593, 1375, 1250, 1169; Mass (m/z): 553, 355 (M+H)$^+$; $^1$H-NMR (δ ppm): 1.18-1.22 (6H, s), 2.51-2.56 (4H, dd), 2.91-2.94 (1H, h), 3.50-3.55 (4H, dd), 3.56-3.61 (2H, d), 6.59-8.20 (12H, m).

EXAMPLE-104

1-(4-Fluorobenzenesulfonyl)-5-methoxy-3-(4-(pyridin-2-yl)piperazin-1-ylmethyl)-1H-indole Using essentially the same procedure as described in example 1, above derivative was prepared. IR spectra (cm$^{-1}$): 1592, 1373, 1270, 1177; Mass (m/z): 481 (M+H)$^+$; $^1$H-NMR (δ ppm): 2.51-2.56 (4H, dd), 3.49-3.54 (4H, dd), 3.61 (2H, s), 3.81 (3H, s), 6.58-8.20 (12H, m).

EXAMPLE-105

1-(4-Methoxybenzenesulfonyl)-5-methoxy-3-(4-(pyridin-2-yl)piperazin-1-ylmethyl)-1H-indole Using essentially the same procedure as described in example 1, above derivative was prepared. Melting Range (°C.): 140-143; IR spectra (cm$^{-1}$): 1595, 1364, 1263, 1166; Mass (m/z): 493 (M+H)$^+$; $^1$H-NMR (δ ppm): 2.53-2.56 (4H, dd), 3.49-3.54 (4H, dd), 3.615-3.169 (2H, d), 3.791 (3H, s), 3.815 (3H, s), 6.582-8.189 (12H, m).

EXAMPLE-106

1-(4-Isopropylbenzenesulfonyl)-5-methoxy-3-(4-(pyridin-2-yl)piperazin-1-ylmethyl)-1H-indole Using essentially the same procedure as described in example 1, above derivative was prepared. Melting Range (°C.): 108-110; IR spectra (cm$^{-1}$): 1594, 1374, 1232, 1137; Mass (m/z): 505 (M+H)$^+$; $^1$H-NMR (δ ppm): 1.17-1.20 (6H, s), 2.52-2.57 (4H, dd), 2.85-2.89 (1H, h), 3.49-3.54 (4H, dd), 3.62 (2H, s), 3.81 (3H, s), 6.58-8.20 (12H, m).

EXAMPLE-107

1-(4-Isopropylbenzenesulfonyl)-5-methoxy-3-(4-(benzyl)piperazin-1-ylmethyl)-1H-indole Using essentially the same procedure as described in example 1, above derivative was prepared. IR spectra (cm$^{-1}$): 1596, 1372, 1275, 1174; Mass (m/z): 518 (M+H)$^+$; $^1$H-NMR (δ ppm): 1.15-1.25 (6H, s, J=20.7 Hz), 2.38-2.58 (8H, bs), 2.85-2.89 (1H, h), 3.51 (2H, 1s), 3.57 (2H, s), 3.81 (3H, s), 6.80-7.80 (13H, m).

EXAMPLE-108

1-(4-Methoxybenzenesulfonyl)-5-methoxy-3-(4-(benzyl)piperazin-1-ylmethyl)-1H-indole Using essentially the same procedure as described in example 1, above derivative was prepared. IR spectra (cm$^{-1}$): 1585, 1371, 1227, 1166; Mass (m/z): 506 (M+H)$^+$; $^1$H-NMR (δ ppm): 2.45-2.88 (8H, bs), 3.50 (2H, s), 3.56 (2H, s), 3.76 (3H, s), 3.81 (3H, s), 6.8-7.86 (13H, m).

EXAMPLE-109

1-(4-Isopropylbenzenesulfonyl)-3-(4-(benzyl)piperazin-1-ylmethyl)-1H-indole

Using essentially the same procedure as described in example 1, above derivative was prepared. Mass (m/z): 488 (M+H)$^+$; $^1$H-NMR (δ ppm): 1.15-1.19 (6H, s, J=6.8 Hz), 2.46 (8H, bs), 2.87 (1H, s), 3.49 (2H, s), 3.61 (2H, s), 7.18-7.99 (14H,m).

EXAMPLE-110

1-(4-Methoxybenzenesulfonyl)-3-(4-(benzyl)piperazin-1-ylmethyl)-1H-indole

Using essentially the same procedure as described in example 1, above derivative was prepared. IR spectra (cm$^{-1}$): 1164, 1260, 1361, 1592; Mass (m/z): 476 (M+H)$^+$; $^1$H-NMR (δ ppm): 2.46 (8H, bs), 3.49 (2H, s), 3.61 (2H, s), 3.78 (3H, s), 6.83-7.97 (14H, m).

EXAMPLE-111

1-(2-Bromo-4-methoxybenzenesulfonyl)-3-(4-(benzyl)piperazin-1-ylmethyl)-1H-indole Using essentially the same procedure as described in example 1, above derivative was prepared. IR spectra (cm$^{-1}$): 1176, 1224, 1366, 1586; Mass (m/z): 555, 557 (M+H)$^+$; $^1$H-NMR (δ ppm): 2.49 (8H, bs), 3.65 (2H, s), 3.66 (2H, s), 3.81 (3H, s), 6.96-8.20 (13H,m).

EXAMPLE-112

1-(Benzenesulfonyl)-3-(4-(benzyl)piperazin-1ylmethyl)-1H-indole

Using essentially the same procedure as described in example 1, above derivative was prepared. IR spectra (cm$^{-1}$): 1174, 1226, 1370, 1584; Mass (m/z): 356 (M+H)$^+$.

EXAMPLE-113

1-[[1-(4-Methoxybenzenesulfonyl)-indol-3-yl]methyl][1,4]diazepane

Using essentially the same procedure as described in example 1, above derivative was prepared. IR spectra (cm$^{-1}$): 1170, 1228, 1372, 1586; Mass (m/z): 400 (M+H)$^+$.

EXAMPLE-114

(R,S) 1-(1-Benzenesulfonyl-indol-3-yl)-1-(4-methylpiperazin-1-yl)ethane

Using essentially the same procedure as described in example 1, above derivative was prepared. IR spectra (cm$^{-1}$): 2966, 2931, 1446, 1370, 1167; Mass (m/z): 384 (M+H)$^+$; $^1$H-NMR (δ ppm): 1.42 (3H, s), 2.24 (3H, s), 2.39-2.46 (8H, bs), 3.78-3.81 (1H, q), 7.20-7.98 (10H, m).

EXAMPLE-115

(R,S) 1-[1-(4-Methylbenzenesulfonyl)indol-3-yl]-1-(4-methylpiperazin-1-yl)ethane Using essentially the same procedure as described in example 1, above derivative was prepared. IR spectra (cm$^{-1}$): 1170, 1368, 1442, 2931, 2966; Mass (m/z): 399 (M+H)$^+$.

EXAMPLE-116

(R,S) 1-[1-(4-Methoxylbenzenesulfonyl)indol-3-yl]-1-(4-methylpiperazin-1-yl)ethane Using essentially the same procedure as described in example 1, above derivative was prepared. IR spectra (cm$^{-1}$): 1150, 1172, 1372, 2935, 2965; Mass (m/z): 414 (M+H)$^+$.

EXAMPLE-117

(R,S) 1-[1-(4-Isopropylbenzenesulfonyl)indol-3-yl]-1-(4-methylpiperazin-1-yl)-ethane Using essentially the same procedure as described in example 1, above derivative was prepared. IR spectra (cm$^{-1}$): 2967, 2934, 1445, 1362, 1178; Mass (m/z): 426 (M+H)$^+$.

EXAMPLE-118

1-(4-Fluorobenzenesulfonyl)-1H-indole-3-carboxylic acid N-(N,N-dimethylaminoethyl)-N-methylamide Using essentially the same procedure as described in example 16, compound in description 186 and was reacted with 4-Fluorobenzenesulfonyl chloride to obtain the above derivative. Mass (m/z): 404 (M+H)$^+$.

EXAMPLE-119

1-(4-Methoxybenzenesulfonyl)-1H-indole-3-carboxylic acid N-(N,N-dimethylaminoethyl)-N-methylamide Using essentially the same procedure as described in example 16, compound in description 186 and was reacted with 4-Methoxybenzenesulfonyl chloride to obtain the above derivative. Mass (m/z): 416 (M+H)$^+$.

EXAMPLE-120

1-(4-Isopropylbenzenesulfonyl)-1H-indole-3-carboxylic acid N-(N,N-dimethylaminoethyl)-N-methylamide Using essentially the same procedure as described in example 16, compound in description 186 and was reacted with 4-Isopropylbenzenesulfonyl chloride to obtain the above derivative. Mass (m/z): 428 (M+H)$^+$.

EXAMPLE-121

(R,S) α-[1-(Benzenesulfonyl)-1H-indol-3-yl]-α-(4-methyl piperazin-1-yl)acetonitrile In a three necked round bottom flask sodium bisulfite (0.26 g, 0.055 moles) was dissolved in 20 mL water. To the above solution 1-Benzenesulfonylindole-3-carboxaldehyde (D1, 1 g, 0.0035 moles) was added and stirred for 1 hr. N-methylpiperazine and sodium cyanide was added at room temperature and the reaction mixture was stirred well for next 12 hrs. After the completion of reaction (TL C), the product was isolated by filtration. The residue was extracted with ethyl acetate (2×25 mL). The combined organic extracts were washed with water, followed by brine, dried over anhydrous sodium sulfate. The organic layer was evaporated under vacuum. The residue obtained was further purified by flash chromatography (silica gel, EtOAc/Hexane, 1/1) to afford a solid material, which was identified by IR, NMR and mass spectral analyses as the title compound. Mass (m/z): 395 (M+H)$^+$.

EXAMPLE-122

(R,S) α-[1-(4-Isopropylbenzenesulfonyl)-1H-indol-3yl]-α-(4-methyl piperazin-1-yl)-acetonitrile Using essentially the same procedure as described in example 121, above derivative was prepared. Mass (m/z): 437 (M+H)$^+$.

EXAMPLE-123

(R,S) α-[1-(4-Methoxybenzenesulfonyl)-1H-indol-3-yl]-α-(4-methyl piperazin-1-yl)acetonitrile Using essentially the same procedure as described in example 121, above derivative was prepared. $^1$H-NMR (δ ppm) 2.27 (3H, s), 2.44 (4H, bs), 2.62 (4H, bs), 3.81 (3H, s), 4.96 (1 H, s), 6.88-8.01 (9H, m); Mass (m/z): 425 (M+H)$^+$

EXAMPLE-124

1-(4-Methoxybenzenesulfonyl)-3-(4-methylpiperazin-1-ylmethyl)-5-nitro-1H-indole

Using essentially the same procedure as described in example 1, above derivative was prepared. Mass IR spectra (cm$^{-1}$): 1116, 1170, 1374, 1450 (m/z): 445 (M+H)$^+$

EXAMPLE-125

1-(Benzenesulfonyl)-3-(4-(benzyloxycarbonyl)-piperazin-1-ylmethyl)-1H-indole

The compound in Description 183 was treated benzensulfonyl chloride according to the procedure given in example 16. Further the protecting group was removed according to the known procedures in the art. Mass (m/z): 490 (M+H)$^+$

EXAMPLE-126

1-(Benzenesulfonyl)-3-(4H-piperazin-1-ylmethyl)-1H-indole

The protecting group in example 125 was removed according to the known procedures in the art. Mass (m/z): 356 (M+H)$^+$.

EXAMPLE-127

1-(4-Methoxybenzenesulfonyl)-3-(4H-piperazin-1-ylmethyl)-1H-indole

A solution of 1-(4-Methoxybenzenesulfonyl)-3-chloromethyl-1H-indole (0.01 mole) in dichloromethane (25 mL) was added slowly over 20-30 minutes to the well stirred and cooled solution of piperazine (0.021 moles) at 5° C. The reaction mixture was further stirred for 30 minutes and then gradually brought to 20 5° C. After completion of the reaction (3-4 hours, TLC), the reaction mixture was further diluted with dichloromethane and washed repeatedly with water and brine. The dichloromethane extract was dried over sodium sulfate and the volatile substances were removed under reduced pressure to obtain the crude intermediate. The residue obtained was purified by flash chromatography (silica gel, EtOAc/MeOH then, MeOH/Triethylamine) to afford the compound, which was identified by IR, NMR and mass spectral analyses as the title compound. The above example can also be prepared according to the procedure given for example 40, and followed by reduction as given in example 53. Mass (m/z): 386 (M+H)$^+$

EXAMPLE-128

1-(4-Isopropylbenzenesulfonyl)-3-(4H-piperazin-1-ylmethyl)-1H-indole

Using essentially the same procedure as described in example 127, 1-(4-Isopropylbenzenesulfonyl)-3-chloromethyl-1H-indole was reacted with piperazine to obtain the above derivative.

Mass (m/z): 398 (M+H)$^+$.

EXAMPLE-129

1-(2-Bromo-4-methoxybenzenesulfonyl)-3-(4H-piperazin-1-ylmethyl)-1H-indole

Using essentially the same procedure as described in example 127, 1-(2-Bromo-4-methoxybenzenesulfonyl)-3-chloromethyl-1H-indole was reacted with piperazine to obtain the above derivative.

Mass (m/z): 464 (M+H)$^+$, 466 (M+3)$^+$;

EXAMPLE-130

5-Bromo-1-(benzenesulfonyl)-3-(4H-piperazin-1-ylmethyl)-1H-indole

Using essentially the same procedure as described in example 127, 5-Bromo-1-Benzenesulfonyl)-3-chloromethyl-1H-indole was reacted with piperazine to obtain the above derivative.

Mass (m/z): 434 (M+H)$^+$, 436 (M+3)$^+$;

EXAMPLE-131

5-Bromo-1-(4-methoxybenzenesulfonyl)-3-(4H-piperazin-1-ylmethyl)-1H-indole

Using essentially the same procedure as described in example 127, 5-Bromo-1-(4-methoxybenzenesulfonyl)-3-chloromethyl-1H-indole was reacted with piperazine to obtain the above derivative.

Mass (m/z): 464 (M+H)$^+$, 466 (M+3)$^+$;

EXAMPLE-132

5-Bromo-1-(4-isopropylbenzenesulfonyl)-3-(4H-piperazin-1-ylmethyl)-1H-indole Using essentially the same procedure as described in example 127, 5-Bromo-1-(4-isopropylbenzenesulfonyl)-3-chloromethyl-1H-indole was reacted with piperazine to obtain the above derivative.

Mass (m/z): 576 (M+H)$^+$, 578 (M+3)$^+$;

EXAMPLE-133

5-Bromo-1-(2-bromo-4-methoxybenzenesulfonyl)-3-(4H-piperazin-1-ylmethyl)-1H-indole Using essentially the same procedure as described in example 127, 5-Bromo-1-(2-bromo-4-methoxybenzenesulfonyl)-3-chloromethyl-1H-indole was reacted with piperazine to obtain the above derivative.

Mass (m/z): 542 (M+H)$^+$, 543 (M+3)$^+$

EXAMPLE-134

1-[[1-(4-Isopropylbenzenesulfonyl)-indol-3-yl]methyl][1,4]diazepane

Using essentially the same procedure as described in example 127, 1-(4-isopropylbenzenesulfonyl)-3-chloromethyl-1H-indole was reacted with homopiperazine to obtain the above derivative.

Mass (m/z): 412 (M+H)$^+$.

EXAMPLE-135

1-[[1-(2-Bromo-4-methoxybenzenesulfonyl)-indol-3-yl]methyl][1,4]diazepane

Using essentially the same procedure as described in example 127, 1-(2-Bromo-4-methoxybenzenesulfonyl)-3-chloromethyl-1H-indole was reacted with homopiperazine to obtain the above derivative.

Mass (m/z): 478 (M+H)$^+$, 480 (M+3)$^+$

EXAMPLE-136

1-[[1-(4-methylbenzenesulfonyl)-indol-3-yl]methyl][1,4]diazepane

Using essentially the same procedure as described in example 127, 1-(4-methylbenzenesulfonyl)-3-chloromethyl-1H-indole was reacted with homopiperazine to obtain the above derivative.

Mass (m/z): 484 (M+H)$^+$.

EXAMPLE-137

1-[[5-Bromo-1-(4-Methoxybenzenesulfonyl)-indol-3-yl]methyl][1,4]diazepane

Using essentially the same procedure as described in example 127, 5-Bromo-1-(4-methoxybenzenesulfonyl)-3-chloromethyl-1H-indole was reacted with homopiperazine to obtain the above derivative.

Mass (m/z): 478 (M+H)$^+$, 480 (M+3)$^+$

EXAMPLE-138

1-[[5-Bromo-1-(4-Isopropylbenzenesulfonyl)-indol-3-yl]methyl][1,4]diazepane

Using essentially the same procedure as described in example 127, 5-Bromo-1-(4-isopropylbenzenesulfonyl)-3-chloromethyl-1H-indole was reacted with homopiperazine to obtain the above derivative.

Mass (m/z): 490 (M+H)$^+$, 492 (M+3)$^+$

EXAMPLE-139

1-[[5-Bromo-1-(2-Bromo-4-methoxybenzenesulfonyl)-indol-3-yl]methyl][1,4]diazepane Using essentially the same procedure as described in example 127, 5-Bromo-1-(2-Bromo-4-methoxybenzenesulfonyl)-3-chloromethyl-1H-indole was reacted with homopiperazine to obtain the above derivative.

Mass (m/z): 556 (M+H)$^+$, 558 (M+3)$^+$

EXAMPLE-140

1-[[5-Bromo-1-(4-methylbenzenesulfonyl)-indol-3-yl]methyl][1,4]diazepane

Using essentially the same procedure as described in example 127, 5-Bromo-1-(4-methylbenzenesulfonyl)-3-chloromethyl-1H-indole was reacted with homopiperazine to obtain the above derivative.

Mass (m/z): 462 (M+H)$^+$, 463 (M+3)$^+$

The invention claimed is:
1. A compound of the general formula (I),

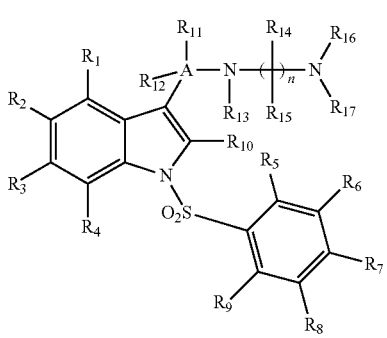

General Formula (I)

its tautomeric form, its stereoisomer, its geometric form, or its pharmaceutically acceptable salt, wherein A is Carbon;

wherein $R_1$, $R_2$, $R_3$, $R_4$, $R_5$, $R_6$, $R_7$, $R_8$, $R_9$, $R_{10}$, $R_{11}$, $R_{12}$, $R_{14}$ and $R_{15}$ may be same or different and each independently represent hydrogen, halogen, oxo, thio, perhaloalkyl, hydroxy, amino, nitro, cyano, formyl, amidino, guanidino, substituted or unsubstituted groups selected from linear or branched $(C_1\text{-}C_{12})$alkyl, $(C_2\text{-}C_{12})$alkenyl, $(C_2\text{-}C_{12})$alkynyl, $(C_3\text{-}C_7)$cycloalkyl, $(C_3\text{-}C_7)$cycloalkenyl, bicycloalkyl, bicycloalkenyl, $(C_1\text{-}C_{12})$alkoxy, cyclo$(C_3\text{-}C_7)$alkoxy, aryl, aryloxy, aralkyl, aralkoxy, heterocyclylalkyloxy, acyl, acyloxy, acylamino, monoalkylamino, dialkylamino, arylamino, diarylamino, aralkylamino, alkoxycarbonyl, hydroxyalkyl, aminoalkyl, monoalkylaminoalkyl, dialkylaminoalkyl, alkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, carboxylic acid, sulfonic acids;

$R_{16}$ and $R_{17}$ may be same or different and each independently represents Hydrogen, substituted or unsubstituted groups selected from linear or branched $(C_1\text{-}C_{12})$ alkyl, $(C_2\text{-}C_{12})$alkenyl, $(C_2\text{-}C_{12})$alkynyl, $(C_3\text{-}C_7)$cycloalkyl, $(C_3\text{-}C_7)$cycloalkenyl, bicycloalkyl, bicycloalkenyl, aryl, aralkyl, heteroaryl or heterocyclylalkyl;

$R_{13}$ along with either $R_{16}$ or $R_{17}$ and the two nitrogen atoms may form a piperazine or diazepine ring, which may be further substituted with $R_{14}$ and $R_{15}$; and n=1.

2. The compound according to claim 1 which is selected from:

1-Benzenesulfonyl-3-(4-methylpiperazin-1-ylmethyl)-5-nitro-1 H-indole;
1-(4-Methylbenzenesulfonyl)-3-(4-methylpiperazin-1-ylmethyl)-5-nitro-1 H-indole;
1-(4-Bromobenzenesulfonyl)-3-(4-methylpiperazin-1-ylmethyl)-5-nitro-1 H-indole;
1-(4-Fluorobenzenesulfonyl)-3-(4-methylpiperazin-1-ylmethyl)-5-nitro-1H-indole;
1-(4-Methoxybenzenesulfonyl)-3-(4-methylpiperazin-1-ylmethyl)-5-nitro-1 H-indole;
1-(4-Isopropylbenzenesulfonyl)-3-(4-methylpiperazin-1-ylmethyl)-5-nitro-1 H-indole;
1-(2-Bromobenzenesulfonyl)-3-(4-methylpiperazin-1-ylmethyl)-5-nitro-1 H-indole;
1-(2-Bromobenzenesulfonyl)-3-(4-methylpiperazin-1-ylmethyl)-5-nitro-1 H-indole hydrochloride salt;
1-(2-Bromo-4-methoxybenzenesulfonyl)-3-(4-methylpiperazin-1-ylmethyl)-5-nitro-1 H -indole;
4,5,6-Trichloro-1-benzenesulfonyl-3-(4-methylpiperazin-1-ylmethyl)-1 H-indole;
4,5,6-Trichloro-1-(4-methylbenzenesulfonyl)-3-(4-methylpiperazin-1-ylmethyl)-1 H -indole;
1-(4-Bromobenzenesulfonyl)-4, 5, 6-trichloro-3-(4-methylpiperazin-1-ylmethyl)-1 H -indole;
4,5, 6-Trichloro-1-(4-isopropylbenzenesulfonyl)-3-(4-methylpiperazin-1-ylmethyl)-1H -indole;
1-(2-Bromobenzenesulfonyl)-4, 5, 6-trichloro-3-(4-methylpiperazin-1-ylmethyl)-1 H -indole;
1-(2-Bromo-4-methoxybenzenesulfonyl)-4, 5, 6-trichloro-3-(4-methylpiperazin-1-ylmethyl)-1 H-indole;
1-Benzenesulfonyl-5-methoxy-3-(4-methylpiperazin-1-ylmethyl)-1H-indole;
1-(4-Methylbenzenesulfonyl)-5-methoxy-3-(4-methylpiperazin-1-ylmethyl)-1 H-indole;
1-(4-Bromobenzenesulfonyl)-5-methoxy-3-(4-methylpiperazin-1-ylmethyl)-1 H-indole;
1-(4-Isopropylbenzenesulfonyl)-5-methoxy-3-(4-methylpiperazin-1-ylmethyl)-1 H-indole;
1-(2-Bromobenzenesulfonyl)-5-methoxy-3-(4-methylpiperazin-1-ylmethyl)-1 H-indole;
1-(2-Bromo-4-methoxybenzenesulfonyl)-5-methoxy-3-(4-methylpiperazin-1-ylmethyl) -1 H-indole;
1-(2-Bromo-4-methoxybenzenesulfonyl)-5-methoxy-3-(4-methylpiperazin-1-ylmethyl)-1 H-indole hydrochloride salt;
1-(4-methoxybenzenesulfonyl)-5-methoxy-3-(4-methylpiperazin-1-ylmethyl)-1 H-indole;
1-(4-Fluorobenzenesulfonyl)-5-methoxy-3-(4-methylpiperazin-1-ylmethyl)-1 H-indole;
5-Bromo1-(4-fluorobenzenesulfonyl)-3-(4-methylpiperazin-1-ylmethyl)-1H-indole;
5-Bromo-1-(4-fluorobenzenesulfonyl)-3-(4-methylpiperazin-1-ylmethyl)-1 H-indole hydrochloride salt;
5-Bromo-1-(4-fluorobenzenesulfonyl)-3-(4-methylpiperazin-1-ylmethyl)-1 H-indole maleate salt;
5-Bromo-1-(4-fluorobenzenesulfonyl)-3-(4-methylpiperazin-1-ylmethyl)-1 H-indole citrate salt;
5-Bromo-1-(4-methoxybenzenesulfonyl)-3-(4-methylpiperazin-1-ylmethyl)-1H-indole;
5-Bromo-1-(benzenesulfonyl)-3-(4-methylpiperazin-1-ylmethyl)-1 H-indole;
5-Bromo-1-(4-methylbenzenesulfonyl)-3-(4-methylpiperazin-1-ylmethyl)-1 H-indole;
5-Bromo-1-(4-bromobenzenesulfonyl)-3-(4-methylpiperazin-1-ylmethyl)-1H-indole;
5-Bromo-1-(4-isopropylbenzenesulfonyl)-3-(4-methylpiperazin-1-ylmethyl)-1H-indole;
5-Bromo-1-(2-bromobenzenesulfonyl)-3-(4-methylpiperazin-1-ylmethyl)-1H-indole;
5-Bromo-1-(2-bromobenzenesulfonyl)-3-(4-methylpiperazin-1-ylmethyl)-1 H-indole hydrochloride salt;
5-Bromo-1-(2-bromo-4-methoxybenzenesulfonyl)-3-(4-methylpiperazin-1-ylmethyl)-1 H -indole;
4-Bromo-1-(4-fluorobenzenesulfonyl)-3-(4-methylpiperazin-1-ylmethyl)-1 H-indole;
4-Bromo-1-(4-methoxybenzenesulfonyl)-3-(4-methylpiperazin-1-ylmethyl)-1 H-indole;
4-Bromo-1-(4-Isopropylbenzenesulfonyl)-3-(4-methylpiperazin-1-ylmethyl)-1H-indole;

(1-Benzenesulfonyl-1 H-indol-3-yl)-(4-methylpiperazin-1-yl)methanone;
[1-(4-Methylbenzenesulfonyl)-1 H-indol-3-yl]-(4-methylpiperazin-1-yl) methanone;
[1-(4-Isopropylbenzenesulfonyl)-1 H-indol-3-yl]-(4-methylpiperazin-1-yl) methanone;
[1-(2-Bromobenzenesulfonyl)-1 H-indol-3-yl]-(4-methylpiperazin-1-yl) methanone;
[1-(2-Bromo-4-methoxybenzenesulfonyl)-1 H-indol-3-yl]-(4-methylpiperazin-1-yl) methanone;
(1-Benzenesulfonyl)-5-nitro-1-H-indol-3-yl)-(4-methylpiperazin-1-yl) methanone;
[1-(4-Methylbenzenesulfonyl)-5-nitro-1 H-indol-3-yl]-(4-methylpiperazin-1-yl) methanone;
[1-(4-Fluorobenzenesulfonyl)-5-nitro-1 H-indol-3-yl]-(4-methylpiperazin-1-yl) methanone;
[1-(4-Bromobenzenesulfonyl)-5-nitro-1H-indol-3-yl]-(4-methylpiperazin-1-yl) methanone;
[1-(4-Isopropylbenzenesulfonyl)-5-nitro-1 H-indol-3-yl]-(4-methylpiperazin-1-yl) methanone;
[1-(2-Bromobenzenesulfonyl)-5-nitro-1 H-indol-3-yl]-(4-methylpiperazin-1-yl) methanone;
[1-(4-Methoxybenzenesulfonyl)-5-nitro-1 H-indol-3-yl]-(4-methylpiperazin-1-yl) methanone;
[1-(2-Bromo-4-methoxybenzenesulfonyl)-5-nitro-1 H-indol-3-yl]-(4-methylpiperazin-1-yl) methanone;
1-Benzenesulfonyl-3-(4-methylpiperazin-1-ylmethyl)-1 H-indole;
1-(4-Methylbenzenesulfonyl)-3-(4-methylpiperazin-1-ylmethyl)-1 H-indole;
1-(4-Fluorobenzenesulfonyl)-3-(4-methylpiperazin-1-ylmethyl)-1H-indole;
1-(4-Bromobenzenesulfonyl)-3-(4-methylpiperazin-1-ylmethyl)-1 H-indole;
1-(4-Isopropylbenzenesulfonyl)-3-(4-methylpiperazin-1-ylmethyl)-1 H-indole;
1-(2-Bromobenzenesulfonyl)-3-(4-methylpiperazin-1-ylmethyl)-1 H-indole;
1-(2-Bromobenzenesulfonyl)-3-(4-methylpiperazin-1-ylmethyl)-1 H-indole hydrochloride salt;
1-(2-Bromo-4-methoxybenzenesulfonyl)-3-(4-methylpiperazin-1-ylmethyl)-1 H-indole;
1-(2-Bromo-4-methoxybenzenesulfonyl)-3-(4-methylpiperazin-1-ylmethyl)-1 H-indole hydrochloride salt;
1-(4-methoxybenzenesulfonyl)-3-(4-methylpiperazin-1-ylmethyl)-1H-indole;
1-(2-Bromo-4-methoxybenzenesulfonyl)-5-chloro-2-methyl-3- (4-methylpiperazin-1-ylmethyl)-1 H-indole;
5-Chloro-1-(4-fluorobenzenesulfonyl)-2-methyl-3-(4-methylpiperazin-1-ylmethyl)-1 H-indole;
1-(4-Bromobenzenesulfonyl)-5-chloro-2-methyl-3-(4-methylpiperazin-1-ylnnethyl)-1 H-indole;
5-Chloro-1-(4-Isopropylbenzenesulfonyl)-2-methyl-3-(4-methylpiperazin-1-ylmethyl)-1 H-indole;
1-Benzenesulfonyl-5-chloro-2-phenyl-3-(4-methylpiperazin-1-ylmethyl)-1 H-indole;
5-Chloro-1-(4-methylbenzenesulfonyl)-2-phenyl-3-(4-methylpiperazin-1-ylmethyl)-1 H-indole;
1-(Benzenesulfonyl)-5-fluoro-2-phenyl-3-(4-methylpiperazin-1-ylmethyl)-1 H-indole;
5-Fluoro-1 -(4-m ethylbenzenesulfonyl)-2-phenyl-3-(4-methylpiperazin-1 -ylmethyl)-1H-indole;
1 -(4-Bromobenzenesulfonyl)-5-chloro-2-phenyl-3-(4-methylpiperazin-1-ylmethyl)-1H-indole;
1-(2-Bromobenzenesulfonyl)-5-cyano-3-(4-methylpiperazin-1-ylmethyl)-1 H-indole;
5-Cyano-1-(4-methoxybenzenesulfonyl)-3-(4-methylpiperazin-1-ylmethyl)-1 H-indole;
5-Cyano-1-(4-fluorobenzenesulfonyl)-3-(4-methyl piperazin-1-ylmethyl)-1 H-indole;
1 -(4-Bromobenzenesulfonyl)-5-cyano-3-(4-methylpiperazin-1-ylmethyl)-1H-indole;
5-Cyano-1-(4-Isopropyl benzenesulfonyl)-3-(4-methylpiperazin-1-ylmethyl)-1H-indole;
N-(1-(4-Fluorobenzenesulfonyl)-1 H-indol-3-yl) methyl-N, N', N'-trimethylethylene-1,2-diamine;
N-(1-(4-Fluorobenzenesulfonyl)-1 H-indol-3-yl) methyl-N, N', N'-trimethylethylene-1,2-diamine hydrochloride salt;
N-(1-(4-Bromobenzenesulfonyl)-5-bromo-1 H-indol-3-yl) methyl-N, N', N'-trimethylethylene-1,2-diamine;
N-(1-(4-Bromobenzenesulfonyl)-5-bromo-1 H-indol-3-yl) methyl-N, N', N'-trimethylethylene-1,2-diamine hydrochloride salt;
N-(5-Bromo-1-(4-methoxybenzenesulfonyl)1H-indol1-3-yl)methyl-N, N', N'-trimethylethylene-1,2-diamine;
N-(1-(4-Methoxybenzenesulfonyl)-5-nitro-1H-indol1-3-yl)methyl-N, N', N'-trimethylethylene-1,2-diamine;
N-(1-(4-Methoxybenzenesulfonyl)-5-nitro-1 H-indol-3-yl) methyl-N, N', N'-trimethylethylene-1,2-diamine hydrochloride salt;
N-(1-(2-Bromobenzenesulfonyl)-5-bromo-1H-indol1-3-yl)methyl-N, N', N'-trimethylethylene-1,2-diamine;
1-(2-Bromobenzenesulfonyl)-3-(4-(3-chlorobenzene-1-yl) piperazin-1-ylmethyl)-1 H-indole;
1-(4-Methoxybenzenesulfonyl)-3-(4-(2-methoxybenzene-1-yl) piperazin-1-ylmethyl)-1 H-indole;
1-(2-Bromo-4-methoxybenzenesulfonyl)-3-(4-(2-methoxybenzene-1-yl)piperazin-1-ylmethyl)-1 H-indole;
1-(4-Isopropylbenzenesulfonyl)-3-(4-(2-methoxybenzene-1-yl) piperazin-1-ylmethyl)-1 H-indole;
5-Bromo-1-(4-fluorobenzenesulfonyl)3-(4-(2-methyoxybenzene-1-yl)piperazin-1-ylmethyl)-1 H-indole;
5-Bromo-1-(4-methoxybenzenesulfonyl)-3-(4-(2-methoxybenzene-1-yl) piperazin-1-ylmethyl)-1 H-indole;
5-Bromo-1-(4-isopropylbenzenesulfonyl)-3-(4-(2-methyoxybenzene-1-yl)piperazin-1-ylmethyl)-1 H-indole;
1-(4-Fluorobenzenesulfonyl)-5-methoxy-3-(4-(2-methoxybenzene-1-yl) piperazin-1-ylmethy))-1 H-indole;
1-(4-Fluorobenzenesulfonyl)-5-methoxy-3-(4-(2-methoxybenzene-1-yl) piperazin-1-ylmethyl)-1 H-indole hydrochloride salt;
1-(4-Methoxybenzenesulfonyl)-5-methoxy-3-(4-(2-methoxybenzene-1-yl) piperazin-1-ylmethyl)-1 H-indole;
1-(4-Isopropylbenzenesulfonyl)-5-methoxy-3-(4-(2-methoxybenzene-1-yl) piperazin-1-ylmethyl)-1H-indole;
1-(4-Fluorobenzenesulfonyl-3-(4-pyridin-2-yl)piperazin-1-ylmethyl)-1H-indole;
1-(4-Methoxybenzenesulfonyl)-3-(4-(pyridin-2-yl) piperazin-1-ylmethyl)-1 H-indole;
1-(4-Isopropylbenzenesulfonyl)-3-(4-(pyridin-2-yl)piperazin-1-ylmethyl)-1H-indole ;
1-(2-Bromobenzenesulfonyl)-3-(4-(pyridin-2-yl) piperazin-1-ylmethyl)-1 H-indole;
1-(2-Bromo-4-methoxybenzenesulfonyl)-3-(4-(pyridin-2-yl) piperazin-1-ylmethyl)-1 H-indole;
5-Bromo-1-(4-fluorobenzenesulfonyl)-3-(4-(pyridin-2-yl) piperazin-1-ylmethyl)-1 H-indole;
5-Bromo-1-(4-methoxybenzenesulfonyl)-3-(4-(pyridin-2-yl) piperazin-1-ylmethyl)-1 H-indole;
5-Bromo-1-(4-isopropylbenzenesulfonyl)-3-(4-(pyridin-2-yl) piperazin-1-ylmethyl)-1 H-indole;

1-(4-Fluorobenzenesulfonyl)-5-methoxy-3-(4-(pyridin-2-yl) piperazin-1-ylmethyl)-1 H-indole;
1-(4-Methoxybenzenesulfonyl)-5-methoxy-3-(4-(pyridin-2-yl) piperazin-1-ylmethyl)-1 H-indole;
1-(4-(Isopropylbenzenesulfonyl)-5-methoxy-3-(4-(pyridin-2-yl) piperazin-1-ylmethyl)-1 H-indole;
1-(4-(Isopropylbenzenesulfonyl)-5-methoxy-3-(4-(benzyl) piperazin-1-ylmethyl)-1 H-indole;
1-(4-Methoxybenzenesulfonyl)-5-methoxy-3-(4-(benzyl) piperazin-1-ylmethyl)-1 H-indole;
1-(4-Isopropylbenzenesulfonyl)-3-(4-(benzyl) piperazin-1-ylmethyl)-1 H-indole;
1-(4-Methoxybenzenesulfonyl)-3-(4-(benzyl) piperazin-1-ylmethyl)-1 H-indole;
1-(2-Bromo-4-methoxybenzenesulfonyl)-3-(4-(benzyl) piperazin-1-ylmethyl)-1 H-indole;
1 -(Benzenesulfonyl)-3-(4-(benzyl)piperazin-1-ylmethyl)-1H-indole;
1-(4-Methoxybenzenesulfonyl)-3-2-[1,4]Diazepan-1-ylmethyl-1 H-indole;
(R, S)1-(1-Benzenesulfonyl-indo1-3-yl)-1-(4-methylpiperazin-1-yl) ethane;
(R)1-(1-Benzenesulfonyl-indo1-3-yl)-1-(4-methylpiperazin-1-yl) ethane;
(S)1-(1-Benzenesulfonyl-indo1-3-yl)-1-(4-methylpiperazin-1-yl) ethane;
(R,S)1-[1-(4-Methylbenzenesulfonyl) indo1-3-yl]-1-(4-methylpiperazin-1-yl) ethane;
(R)1-[1-(4-Methylbenzenesulfonyl) indo1-3-yl]-1-(4-methylpiperazin-1-yl) ethane;
(S)1-[1-(4-Methylbenzenesulfonyl) indo1-3-yl]-1-(4-methylpiperazin-1-yl) ethane;
(R,S)1-[1-(4-Methoxybenzenesulfonyl) indo1-3-yl]-1-(4-methylpiperazin-1-yl) ethane;
(R)1-[1-(4-Methoxybenzenesulfonyl) indo1-3-yl]-1-(4-methylpiperazin-1-yl) ethane;
(S)1-[1-(4-Methoxylbenzenesulfonyl) indol-3-yl]-1-(4-methylpiperazin-1-yl) ethane;
(R,S)1-[1-(4-Isopropylbenzenesulfonyl) indo1-3-yl]-1-(4-methylpiperazin-1-yl) ethane;
(R)1-[1-(4-Isopropylbenzenesulfonyl) indo1-3-yl]-1-(4-methylpiperazin-1-yl) ethane;
(S)1-[1-(4-Isopropylbenzenesulfonyl) indo1-3-yl]-1-(4-methylpiperazin-1-yl) ethane;
1-(4-Flurobenzenesulfonyl)-1H-indole-3-carboxylic acid N-(N, N-dimethylaminoethyl)-N-methylamide;
1-(4-Methoxybenzenesulfonyl)-1H-indole-3-carboxylic acid N-(N, N -dimethylaminoethyl)-N-methylamide;
1-(4-Isopropylbenzenesulfonyl)-1 H-indole-3-carboxylic acid N-(N', N'-dimethylaminoethyl)-N-methylamide;
(R,S) α-[1-(4-Methoxybenzenesulfonyl)-1 H-indo1-3-yl]-α-(4-methylpiperazin-1-yl) acetonitrile;
(R)α-[1-(4-Methoxybenzenesulfonyl)-1H-indol1-3-yl]-α-(4-methylpiperazin-1-yl,) acetonitrile;
(S)α-[1-(4-Methoxybenzenesulfonyl)-1 H-indol1-3-yl]-α-(4-methylpiperazin-1-yl) acetonitrile;
(R, S)α-[1-(Benzenesulfonyl)-1 H-indol1-3-yl]-α-(4-methylpiperazin-1-yl) acetonitrile;
(R)α-[1-(Benzenesulfonyl)-1 H-indol1-3-yl]α-(4-methylpiperazin-1-yl) acetonitrile ;
(S)α-[1-(Benzenesulfonyl)-1 H-indol1-3-yl]α-(4-methylpiperazin-1-yl) acetonitrile;
(R,S)α-[1-(4-Isopropylbenzenesulfonyl)-1H-indol-3-yl]-α-(4-methylpiperazin-1-yl) -acetonitrile;
(R)α-[1-(4-Isopropylbenzenesulfonyl)-1 H-indol-3-yl]-α-(4-methylpiperazin-1-yl) -acetonitrile;
(S)α-[1-(4-Isopropylbenzenesulfonyl)-1H-indol-3-yl]-α-(4-methylpiperazin-1-yl) -acetonitrile;
1-(Benzenesulfonyl)-3-(4-(benzyloxycarbonyl)-piperazin-1-yl methyl)-1 H-indole;
1-(Benzenesulfonyl)-3-(4H-piperazin-1-ylmethyl)-1 H-indole;
1-(4-Methoxybenzenesulfonyl)-3-(4H-piperazin-1-ylmethyl)-1 H-indole
1-(4-Isopropylbenzenesulfonyl)-3-(4H-piperazin-1-ylmethyl)-1 H-indole
1-(2-Bromo-4-methoxybenzenesulfonyl)-3-(4H-piperazin-l-ylmethyl)-1 H-indole
5-Bromo-1-(benzenesulfonyl)-3-(4H-piperazin-1-ylmethyl)-1 H-indole;
5-Bromo-1-(4-methoxybenzenesulfonyl)-3-(4H-piperazin-l-ylmethyl)-1 H-indole
5-Bromo-1-(4-isopropylbenzenesulfonyl)-3-(4H-piperazin-1-ylmethyl)-1 H-indole
5-Bromo-1-(2-bromo-4-methoxybenzenesulfonyl)-3-(4H-piperazin-1-ylmethyl)-1H-indole
1-[[1-(4-Isopropylbenzenesulfonyl)-indol-3-yl]methyl][1,4]diazepane
1-[[1-(2-Bromo-4-methoxybenzenesulfonyl)-indoll-3-yl]methyl][1,4]diazepane
1-[(1-(4-methylbenzenesulfonyl)-indol-3-yl]methyl][1,4]diazepane
1-[[5-Bromo-1-(4-Methoxybenzenesulfonyl)-indol-3-yl]methyl][1,4]diazepane
1-[[5-Bromo-1-(4-Isopropylbenzenesulfonyl)-indol-3-yl]methyl][1,4]diazepane
1-[[5-Bromo-1-(2-Bromo-4-methoxybenzenesulfonyl)-indo1-3-yl]methyl][1,4]diazepane
1-([5-Bromo-1-(4-methylbenzenesulfonyl)-indol-3-yl]methyl][1,4]diazepane
and their pharmaceutically acceptable salts.

3. A pharmaceutical composition comprising either of a pharmaceutically acceptable carrier, a diluent, or excipients along with a therapeutically effective amount of a compound according to claim 1, its tautomeric forms, its sterioisomers, its geometric forms, or its pharmaceutically acceptable salts.

4. The pharmaceutical composition according to claim 3, in the form of a tablet, capsule, powder, syrup, injectable solution or suspension.

5. A process for the preparation of a compound of general formula (I) in accordance with claim 1 wherein A is Carbon; wherein $R_1$, $R_2$, $R_3$, $R_4$, $R_5$, $R_6$, $R_7$, $R_8$, $R_9$, $R_{10}$, $R_{11}$, $R_{12}$, $R_{14}$ and $R_{15}$ may be the same or different and each independently represent hydrogen, halogen, oxo, thio, perhaloalkyl, hydroxy, amino, nitro, cyano, formyl, amidino, guanidino, substituted or unsubstituted groups selected from linear or branched ($C_1$-$C_{12}$)alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$) alkoxy, cyclo($C_3$-$C_7$)alkoxy, aryl, aryloxy, aralkyl, aralkoxy, heterocyclylalkyloxy, acyl, acyloxy, acylamino, monoalkylamino, dialkylamino, arylamino, diarylamino, aralkylamino, alkoxycarbonyl, hydroxyalkyl, aminoalkyl, monoalkylaminoalkyl, dialkylaminoalkyl, alkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, carboxylic acid, sulfonic acids;

$R_{16}$ and $R_{17}$ may be the same or different and each independently represents Hydrogen, substituted or unsubstituted groups selected from linear or branched ($C_1$-$C_{12}$)

alkyl, $(C_2-C_{12})$alkenyl, $(C_2-C_{12})$alkynyl, $(C_3-C_7)$ cycloalkyl, $(C_3-C_7)$cycloalkenyl, bicycloalkyl, bicycloalkenyl, aryl, aralkyl, heteroaryl or heterocyclylalkyl;

$R_{13}$ along with either $R_{16}$ or $R_{17}$ and the two nitrogen atoms may form a piperazine or diazepine ring, which may be further substituted with $R_{14}$ and $R_{15}$; and n=1;

which comprises the step of reacting a compound of formula (IV) given below,

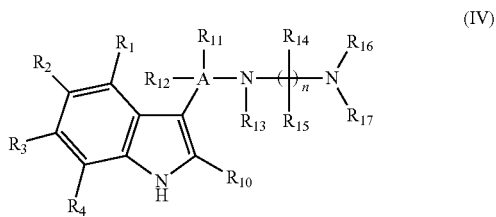
(IV)

wherein all the symbols are as defined earlier with a compound of formula (V),

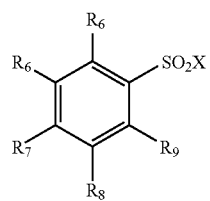
(V)

where all the symbols are as defined earlier; and X is halogen.

6. The process according to claim 5 comprising of carrying out one or more of the following optional steps: i) removing any protecting group; ii) resolving the racemic mixture into pure enantiomers by the known methods and iii) preparing a pharmaceutically acceptable salt of a compound of formula (I).

7. Novel compounds of general formula (IV) as defined below,

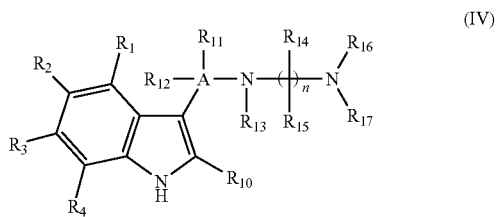
(IV)

wherein all symbols are as defined earlier.

8. A method for the treatment of Alzheimer's disease, comprising the step of administering to a patient in need thereof, an effective amount of a compound of general formula (I) as claimed in claim 1.

9. A method for the treatment of schizophrenia, comprising the step of administering to a patient in need thereof, an effective amount of a compound of general formula (I) as claimed in claim 1.

* * * * *